US012154244B2

(12) United States Patent
Cofar et al.

(10) Patent No.: US 12,154,244 B2
(45) Date of Patent: Nov. 26, 2024

(54) COMPUTER IMPLEMENTED METHODS FOR DENTAL DESIGN

(71) Applicant: SMILECLOUD SRL, Timisoara (RO)

(72) Inventors: Florin-Nicolae Cofar, Dumbravita (RO); Eric Van Dooren, Wilrijk (BE); Mihai Simonia, Timisoara (RO); Cristian Diaconescu, Timisoara (RO); Radu-Florin Sarghe, Timisoara (RO); Cristian-Florin Marta, Timisoara (RO)

(73) Assignee: SMILECLOUD SRL, Timisoara (RO)

( * ) Notice: Subject to any disclaimer, the term of this patent is extended or adjusted under 35 U.S.C. 154(b) by 0 days.

(21) Appl. No.: 17/879,617

(22) Filed: Aug. 2, 2022

(65) Prior Publication Data

US 2023/0051506 A1  Feb. 16, 2023

Related U.S. Application Data

(63) Continuation-in-part of application No. 17/400,378, filed on Aug. 12, 2021.

(51) Int. Cl.
G06T 19/20 (2011.01)
A61C 9/00 (2006.01)
A61C 13/34 (2006.01)

(52) U.S. Cl.
CPC ............ *G06T 19/20* (2013.01); *A61C 9/0053* (2013.01); *A61C 13/34* (2013.01);
(Continued)

(58) Field of Classification Search
CPC ....... A61C 9/0053; A61C 13/34; G06T 11/60; G06T 19/006; G06T 19/20
See application file for complete search history.

(56) References Cited

U.S. PATENT DOCUMENTS

2009/0148816 A1    6/2009   Marshall et al.
2013/0108988 A1    5/2013   Simoncic
(Continued)

FOREIGN PATENT DOCUMENTS

WO     2020161082 A1    8/2020

OTHER PUBLICATIONS

Zanjani et al., Mask-MCNet: Instance Segmentation in 3D Point Cloud of Intra-oral Scans, Medical Image Computing and Computer Assisted Intervention 2019, pp. 128-136 (Year: 2019).*
(Continued)

*Primary Examiner* — Charles Tseng
(74) *Attorney, Agent, or Firm* — Dinsmore & Shohl LLP

(57) ABSTRACT

Computer implemented method of generating a dental design, comprising: (a) capturing a facial image comprising a head of a patient and a smile; (b) displaying it as a first image; (c) capturing a 3D intraoral scan; (d) aligning the 3D scan to the head; (e) determining bounding boxes in the 3D scan, each comprising a single tooth; (f) showing a view of the 3D scan and the bounding boxes as a second image; (g) showing the bounding boxes as overlay on the first image; (i) allowing the bounding boxes to be resized/repositioned; (ii) defining a limited set of parameters to characterize the tooth inside the bounding box, and searching a number of candidate matching teeth from a 3D digital library of teeth, and proposing a candidate matching tooth; (iii) overlaying the first image with a digital representation of the proposed candidate matching tooth from the digital library.

15 Claims, 36 Drawing Sheets

(52) U.S. Cl.
CPC ...... *G06T 2200/24* (2013.01); *G06T 2210/12* (2013.01); *G06T 2219/2004* (2013.01); *G06T 2219/2016* (2013.01)

(56) References Cited

U.S. PATENT DOCUMENTS

2013/0282351 A1   10/2013  Tank
2018/0153649 A1*  6/2018  Wu ........................ G16H 40/67
2019/0350680 A1*  11/2019  Chekh .................... G06T 5/002

OTHER PUBLICATIONS

International Search Report, issued Apr. 15, 2020, pertaining to PCT/EP2020/052638, filed Feb. 3, 2020, 3 pages.
Written Opinion, issued Apr. 15, 2020, pertaining to PCT/EP2020/052638, filed Feb. 3, 2020, 8 pages.

* cited by examiner

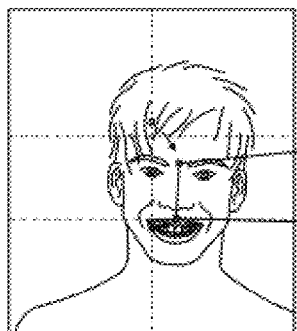
FIG. 4A Straighten face
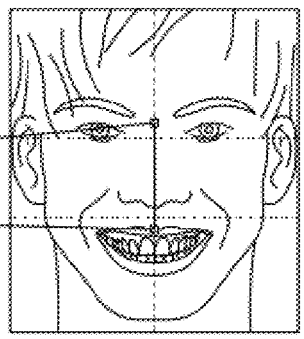
FIG. 4B
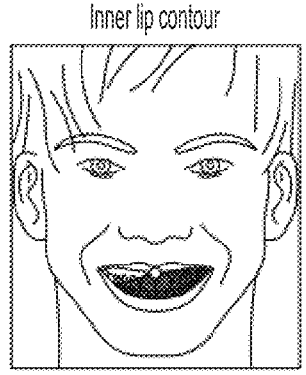
Inner lip contour
FIG. 4C
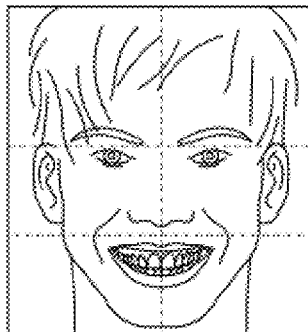
FIG. 4D
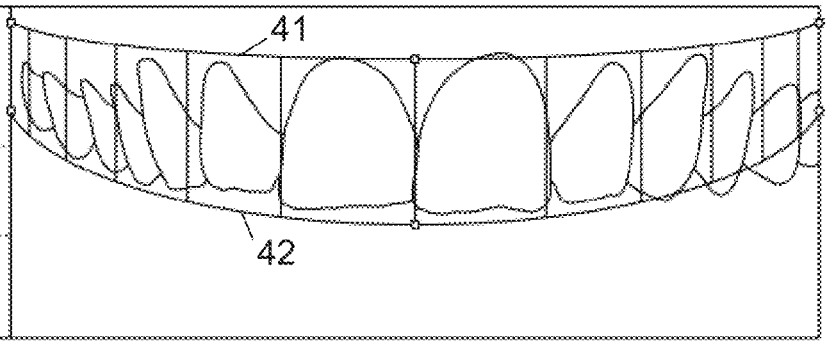
FIG. 4E Restorative space
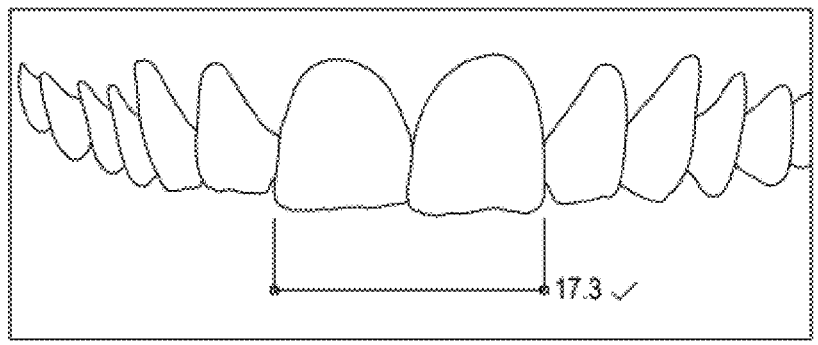
FIG. 4F Calibration
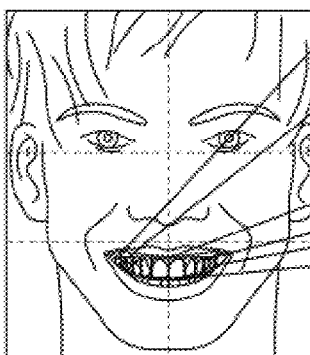
FIG. 4G
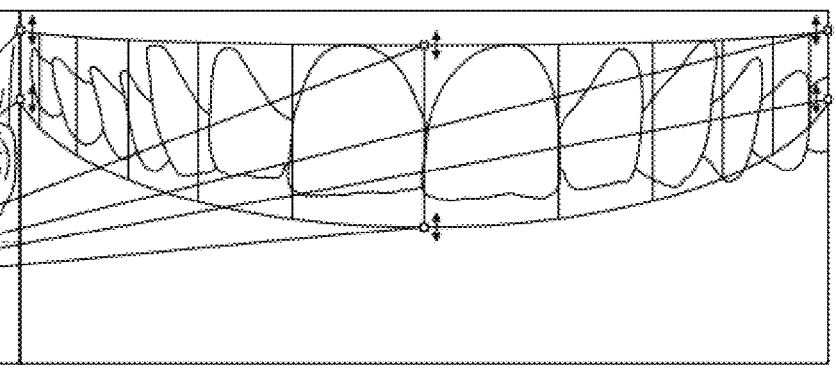
Gingiva and smile curve
FIG. 4H

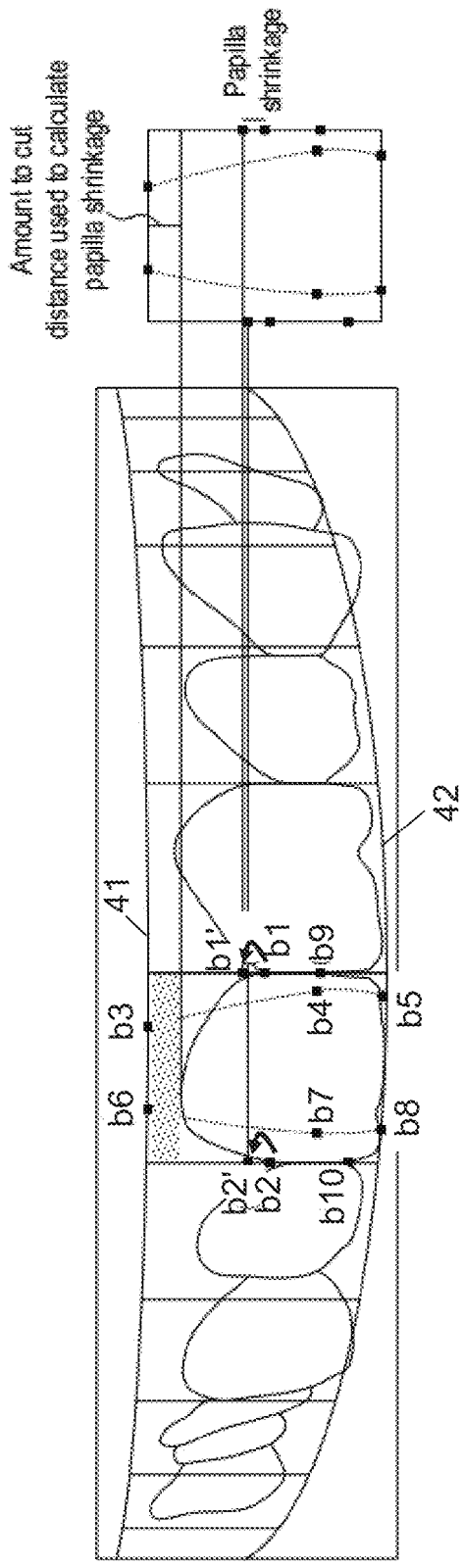
FIG. 6A
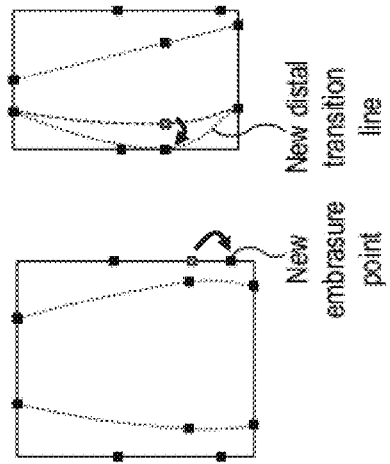
FIG. 6B
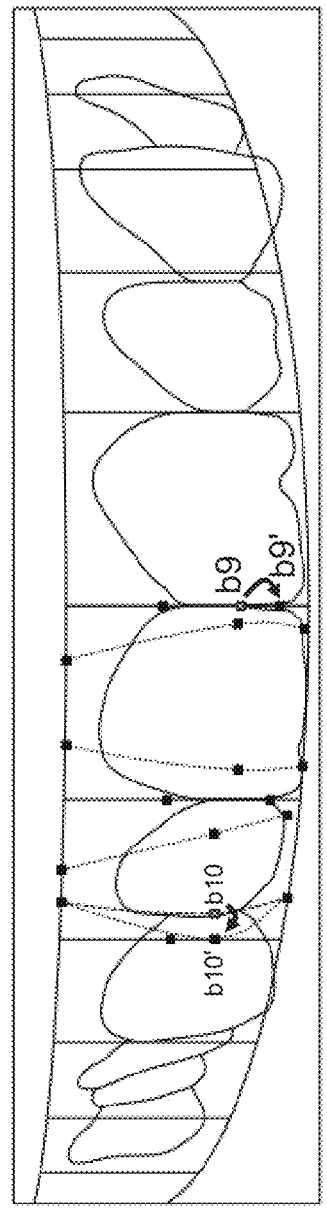
FIG. 6C
FIG. 6D  FIG. 6E

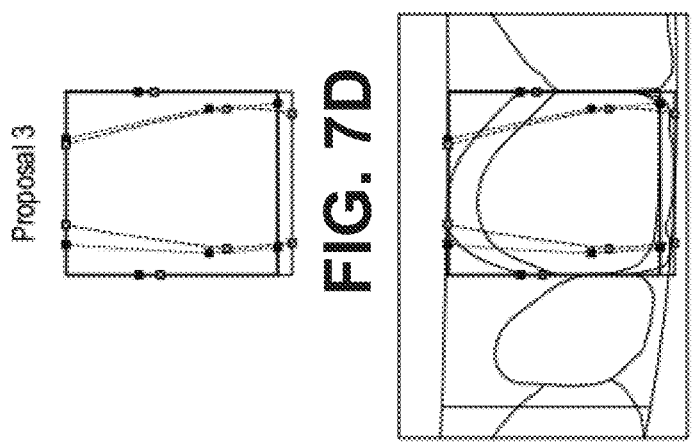
FIG. 7A  FIG. 7B  FIG. 7C  FIG. 7D
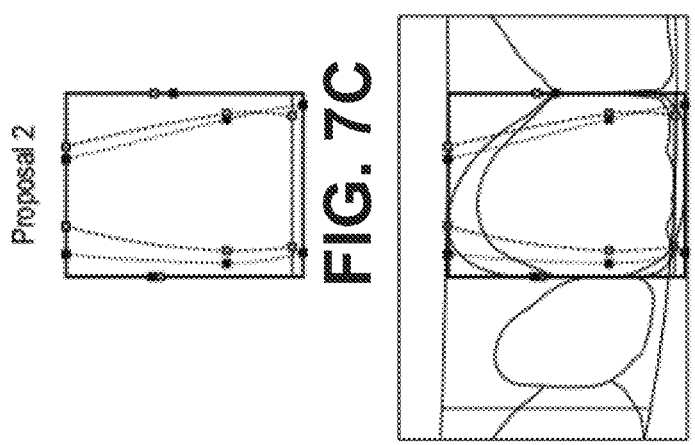
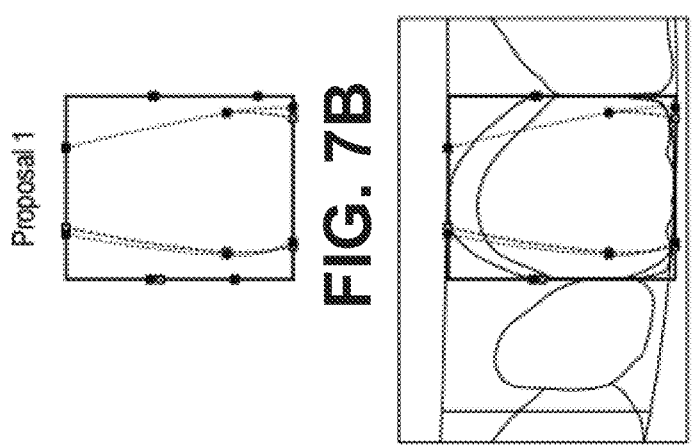
FIG. 7E  FIG. 7F  FIG. 7G

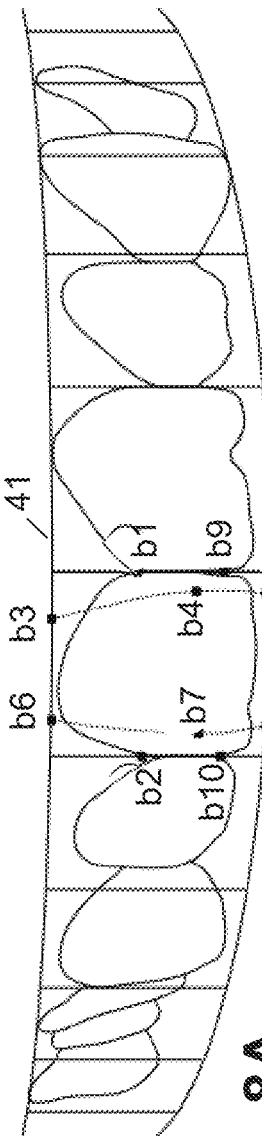
FIG. 8A
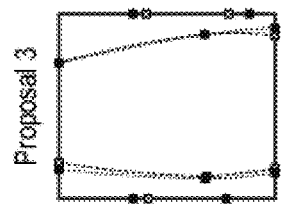
FIG. 8B
FIG. 8C / FIG. 8D / FIG. 8E / FIG. 8F
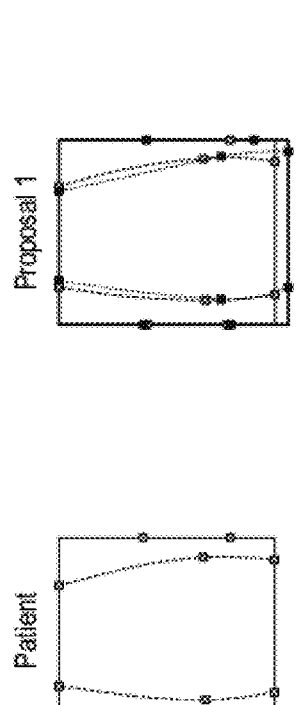
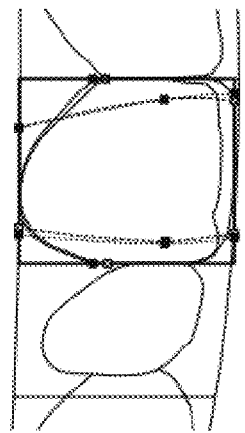
FIG. 8G
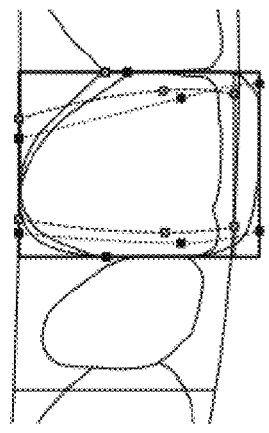
FIG. 8H
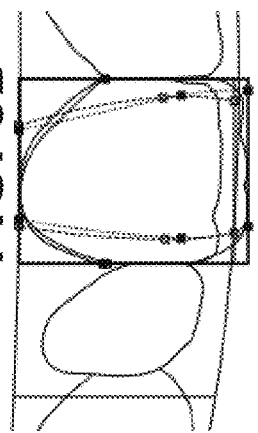
FIG. 8I

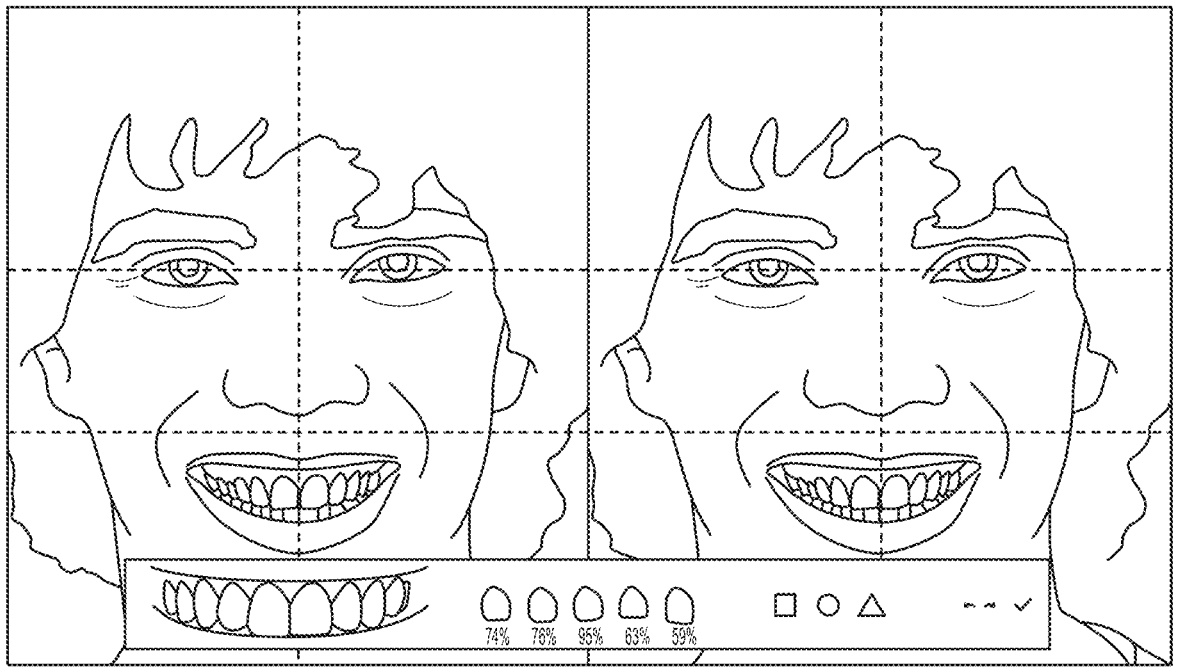
FIG. 16A  FIG. 16B
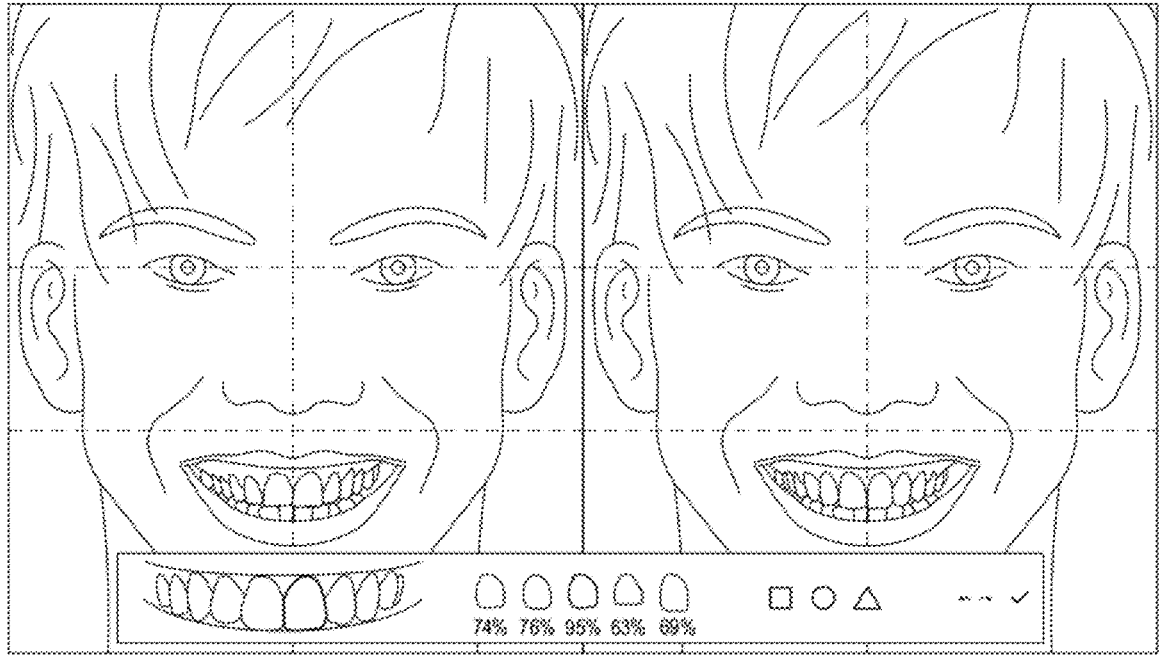
FIG. 16C  FIG. 16D

(H=10.14mm; MS of tooth X is 85.4%)

(H=10.56mm; MS of tooth X is 82%)

(H=10.14mm; MS of tooth X is 85.4%)

(H=10.56mm; MS of tooth X is 82%)

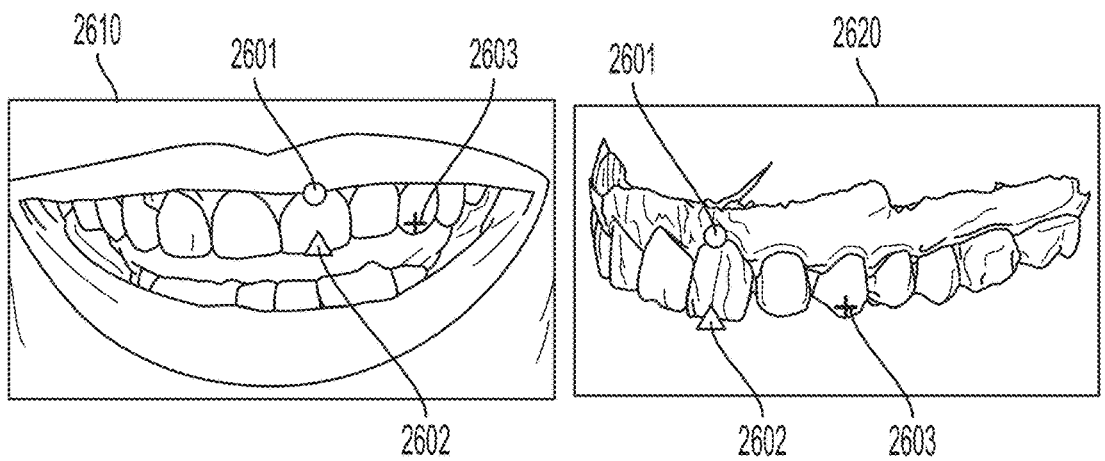
FIG. 26A  FIG. 26B
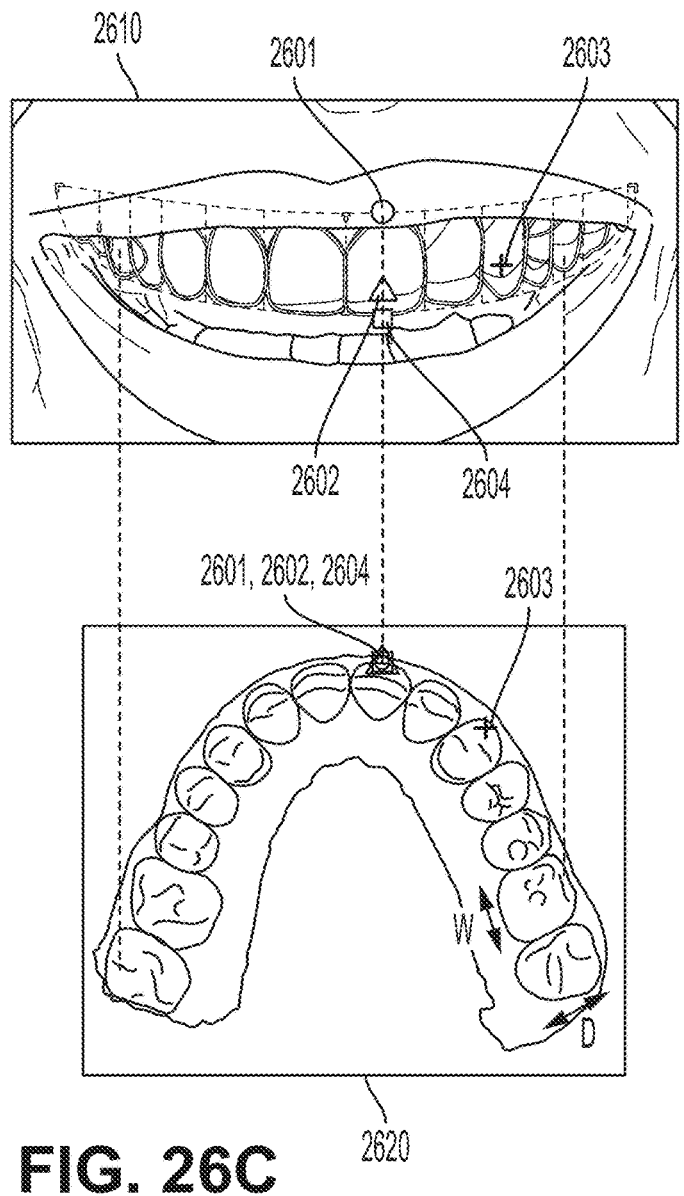
FIG. 26C

COMPUTER IMPLEMENTED METHODS FOR DENTAL DESIGN

CROSS-REFERENCES TO RELATED APPLICATIONS

This application is a continuation-in-part of U.S. patent application Ser. No. 17/400,378, filed Aug. 12, 2021, which is hereby incorporated by reference herein in its entirety.

TECHNICAL FIELD

The present disclosure relates in general to the field of dental design and dental restoration. More in particular, the present disclosure relates to computer implemented methods for characterising a tooth, computer implemented methods for building a digital database of teeth, computer implemented methods for searching said database to find a matching tooth, computer implemented methods for designing or defining a dental design or restoration, computer implemented methods for generating a physical object for dental restoration, and a method of dental treatment.

BACKGROUND

Techniques for designing and manufacturing dental restorations such as e.g. crowns, bridges, abutments, implants, veneers, etc. are known in the art.

In recent years, computer programs for designing and manufacturing dental restoration are rapidly expanding. A first step in typical computer aided manufacturing processes is to create a 3-dimensional model of the patient's teeth. This is traditionally done by 3D scanning one or both of the dental gypsum models. The 3-dimensional replicas of the teeth are imported into a CAD program, where the entire dental restoration is designed. The final restoration 3D design is then manufactured e.g. using a milling machine, 3D printer, rapid prototyping manufacturing or other manufacturing equipment.

While CAD programs can help to design and visualize virtual 3D objects, it remains a challenge to obtain good results (e.g. accurately fitting, visually appearing, esthetical, etc.) using such programs, moreover in a fast and efficient manner.

US2013/0060532 describes a computer implemented method for designing a high aesthetic composition starting from a high number of interrelated virtual teeth.

There is always room for improvements or alternatives.

SUMMARY

It is an object of embodiments of this disclosure to provide a computer implemented method for generating a dental design of a patient in a fast and efficient manner.

It is an object of embodiments of this disclosure to provide a computer implemented method for generating a dental design and/or producing a dental object that corresponds better with the intended (future) design.

It is a particular object of embodiments of this disclosure to provide a computer implemented method for generating a dental design and/or producing a dental object that takes into account, or takes into account in an improved manner, a possible tilt or inclination between the upper jaw of the patient and the head of the patient, e.g. as illustrated in FIG. 22A.

It is also an object of embodiments of this disclosure to provide a computer program product for performing such a method, and a storage medium comprising such a computer program product, and a computer system for performing such a method.

It is also an object of embodiments of this disclosure to provide a method of treatment of a patient using such a method.

These and other objects are accomplished by computer implemented methods, computer program products, and a method of treatment according to embodiments of this disclosure.

According to a first aspect, this disclosure provides a computer implemented method of generating a dental design, the method comprising the steps of: (a) capturing or obtaining a facial image of a patient, said facial image comprising a head of the patient and a smile comprising a plurality of upper teeth; (b) showing the facial image or an image derived therefrom on a display as a first image; (c) capturing or obtaining a 3D intraoral scan comprising said plurality of upper teeth; (d) aligning the 3D intraoral scan to the head of the patient; (e) determining a plurality of 3D bounding boxes in the 3D intraoral scan, each bounding box comprising a single tooth and determining a gingival margin curve of the tooth; (f) showing a view of said 3D intraoral scan and the 3D bounding boxes as a second image on said display, preferably simultaneously with the first image, and showing a plurality of characteristic points related to the gingival margin curve; (g) showing a representation of the 3D bounding boxes and a representation of the gingival margin curve as a graphical overlay on the first image on said display; (h) performing at least once step (i) to (iii), wherein (i) allowing a user to modify at least one dimension (e.g. With, Depth, Height) and optionally also a position and/or a rotation of at least one 3D bounding box in the first or second image, and/or allowing the user to modify one or more of the characteristic points related to the gingival margin curve, and detecting said modification; (ii) for each modification, defining a limited set of parameters to characterize the tooth inside the 3D bounding box, including a parameter indicative for the unique position of the tooth in a mouth, and dimensions of the 3D bounding box, and including positions of the plurality of characteristic points related to the gingival margin curve, and searching and retrieving a limited number of candidate matching teeth from an indexed digital library comprising a plurality of 3D digital teeth, the index being based on said limited set of parameters and being used to determine a matching score between a digital tooth from the library and the modified 3D bounding box and/or the modified representation of the gingival margin curve, and proposing a candidate matching tooth from said limited number of candidate matching teeth; (iii) overlaying the first image with a digital representation (e.g. a contour or a projection) of the proposed candidate matching tooth from the digital library.

The alignment of the 3D intraoral scan and the head of the patient using the facial image allows the facial image (or an image derived therefrom) to be accurately overlaid by a digital representation of one or more objects in the 3D intraoral scan using a transformation (e.g. a projection onto a plane perpendicular to the viewing angle from which the facial image was captured).

This method allows to digitize and characterize the teeth of a patient in relation to the head of the patient, which is different from merely digitizing the teeth using an intraoral scanner. This difference is important, for example, when the upper jaw of the patient is canted relative to the head, and because the length of the teeth is usually determined based on modifications performed on the facial image, e.g. by a dentist trying to create a "beautiful smile". Indeed, if the dental design would be based solely on the 3D intraoral scan, without taking into account the relative position of the jaw and the head, the resulting dental restoration will not correspond to the picture of the "future teeth" or "predicted dental restoration" shown to the patient, e.g. as an overlay of contours over the first image.

The alignment can be performed in known manners, e.g. by manually indicating the screen positions of a certain number of points in the first image and the second image.

This method allows for the creation of a digital design where any tooth of the patient, e.g. a damaged tooth, can be replaced by a suitable tooth from the digital library.

It is a major advantage of this method that it does not require a 2D digital library of teeth, but only requires a 3D digital library of individual teeth. Preferably this 3D digital library is indexed using a limited number of parameters, such that it can be searched efficiently.

It is a major advantage to also include a representation of the gingival margin curve (e.g. relative positions of a few characteristic points of the gingival margin curve) in the index file, and to use them also in the matching score. In this way, the system can search for matching teeth in the database, not only when the dentist changes dimensions of the bounding box (e.g. because the patient wants longer teeth), but also, when the dentist changes the position of the envisioned gingival margin curve (which is the case in a majority of the cases).

In an embodiment, the alignment is performed by indicating corresponding screen positions of a plurality of particular points in the facial image, and in a projection or a view of the 3D model. e.g. by automatically finding or manually indicating positions of a plurality of specific points in the facial image and in a projection or a view of the 3D digital model.

In an embodiment, the characteristic points related to the gingival margin curve are projections on at least one surface of the 3D bounding box, and the index file comprises positions (or coordinates) of these characteristic points on said 2D surface (e.g. as two percentage values).

In an embodiment, the method further comprises: saving the digital design as a digital file on a non-volatile memory (e.g. a USB stick or a flash card) or on a storage device (e.g. on a hard disk drive, a CD-ROM, a DVD-disk, a Blue-Ray disk, a network drive). The digital file may comprise one or more of: the first set of limited parameters, a position e.g. in the form of screen coordinates of the plurality of visual objects, a reference to said at least two teeth in the digital library.

In an embodiment, the method further comprises: providing a 3D-file of at least one candidate matching tooth from the digital library, optionally after scaling, rotation or digital grinding.

The 3D file may be suitable for printing by a 3D printer. It is an advantage of this embodiment that it generates a 3D-file which can be used to create a physical realisation of the one or more dental restoration. This 3D file may for example be used to build a wax-model.

In an embodiment, the method further comprises: producing at least one physical object based on said 3D file, e.g. in the form of a crown, a bridge, an abutment, an implant, a veneer.

The facial image may be a digital representation, e.g. a projection of a 3D facial scan, obtained from a facial scanner.

The facial image may be a 2D image obtained from a digital camera.

The facial image or 2D image may be a frontal picture, a lateral picture or a portrait picture.

The facial image or 2D image may be captured by a 2D digital camera, of the kind that typically saves the picture in a two-dimensional compressed file format, such as JPG.

Step (b) may further comprise: rotating the 2D image such that an imaginary line passing through the eyes of the patient is oriented substantially horizontally on the screen.

The 3D intraoral scan may be acquired by a so called "intraoral scanner". The 3D digital model may comprise a plurality of polygons having a certain position and orientation relative to a reference frame of the 3D digital model.

In an embodiment, the alignment of step d) comprises: aligning a reference frame of the 3D digital model to a reference frame of the head of the patient using the facial image or an image derived therefrom (e.g. after rotation, cropping, scaling). Each reference frame may comprise three orthogonal axes, but that is not absolutely required, and other coordinate systems may also be used. The alignment may comprise finding or indicating coordinates of a plurality of specific points in the first image and in the second image, e.g. as illustrated in FIGS. 26A and 26B.

In an embodiment, the bounding boxes have a beam shape or a cuboid shape or a prism shape.

In an embodiment, the method further comprises: displaying a U-shaped curve tangential or substantially tangential or substantially parallel to a line segment that is tangential to an outside surface of the (existing) teeth of the patient, and situated near incisal edges of the teeth. With "substantially tangential" is meant: defining an angle smaller than 15° or smaller than 10°, or smaller than 5°.

The U-shaped curve defined by the incisal edges of the existing (or original) teeth of the patient, is preferably planar, meaning it is preferably located in a virtual plane. In practice the incisal edges of some of the teeth may be located above this virtual plane, and some incisal edges may be located above this virtual plane.

In an embodiment, the virtual plane is chosen such that the sum of absolute distances between the incisal edges of the teeth and the plane is minimal, or is chosen such that the sum of the squares of the distances between the incisal edges of the teeth and the plane is minimal. It is noted that the exact location of the "original" plane is not crucial to the embodiments herein, since in a typical dental design, this curve will be moved anyway. And the exact location is not critical for the "alignment" between the 3D model and the head orientation either, because a parallel plane which is offset in a direction perpendicular to the "original plane" can also be used to align.

In an embodiment, a U-shaped curve is used for the alignment of the 3D model and the head of the patient, e.g. by indicating corresponding incisal edges of the teeth in the 3D model and on the projected U-shaped curve overlaid on the 2D-image, or by indicating corresponding zeniths of the teeth in the 3D model and on the projected U-shaped curve overlaid on the 2D-image.

In an embodiment, the bounding boxes have a plurality of rectangular surfaces including one surface being tangential or substantially tangential or substantially parallel to a surface that is tangential to said U-shaped curve, for example as illustrated in FIG. 27C.

In an embodiment, the bounding boxes have a plurality of ribs which form an angle smaller than 15° with a vertical axis of the head of the patient, preferably smaller than 10° or smaller than 5°.

Similar to what was described in the embodiments of FIGS. 1A through 20, the search algorithm may determine a matching score. The matching score is indicative for a degree of correspondence between parameters of an existing tooth or an envisioned tooth (also called "future tooth") and a tooth from the 3D digital library. The matching score may be calculated as a sum of absolute values of differences between parameters of the envisioned tooth and the tooth from the library, or a weighted sum of absolute values of said differences, or a sum of squares of said differences, or a weighted sum of squares of said differences.

In an embodiment, defining or determining a limited set of parameters to characterize the tooth inside the bounding box further comprises: determining at least one parameter (e.g. a1) for describing a first papilla height, and determining at least one parameter (e.g. a2) for describing a second papilla height.

When the matching score is determined as a weighted sum, the weight factor of the dimensions are preferably higher than the weighting factors of the papilla heights.

In an embodiment, the envisioned (e.g. desired) gingival margin curve is represented as a spline or as a "simple Bezier curve" passing through at least three characteristic points, shown as a projection on one of the surfaces of the 3D bounding box, preferably the surface tangential to the U-shaped curve, and facing outwardly (away from the patient).

The characteristic points preferably include at least three points: two extremes corresponding to the first papilla height and the second papilla height, and one additional point near the "top", e.g. furthest away from the incisal edge. Optionally also other characteristic points are shown, e.g. a characteristic point (not a real point of the curve, but a visual representation of an object, e.g. a small square, that can easily be dragged by the mouse) for modifying the slope of a virtual line tangential to the spline or Bezier curve at the extremes, and/or a characteristic point for modifying the curvature or smoothness (e.g. second order derivative) of the curve at the "top".

Experiments have shown that the shape and/or position of the spline or Bezier curve can easily and rapidly be modified by changing one or more of the following: (i) the positions of the characteristic points, (ii) the slopes of the extremes (left and right papilla height), and (iii) the curvature or smoothness of an intermediate point, e.g. of the "top" of the curve.

It is noted that the "physical gingival margin curve" is in reality a 3D curve in 3D space, and this curve is not easy to describe with only a few parameters. However, the inventors came to realize (i) that only a portion of the gingival margin curve is relevant for most dental restorations, namely the portion that is visible from the outside of the mouth, and (ii) they surprisingly found that it is technically feasible to approximate a projection of this portion onto a plane, e.g. onto one of the surfaces of the 3D bounding box, and to approximate this projected portion by means of a spline or a simple Bezier curve, requiring only a small number of parameters, and (iii) the 2D coordinates of the characteristic points can for example be specified as percentage values, relative to the dimensions of the bounding box.

The overall result is that the gingival margin curve can be efficiently codified in the index file by means of less than ten values, e.g. at most seven values, e.g. at most five values. The values may be percentage values (relative to the dimensions of the bounding box).

By adding these parameters to the index file, and using them also in the matching score, it is thus possible to quickly find a matching tooth from the digital library that not only fits inside the 3D bounding box, but moreover has a very similar gingival margin curve. It is an advantage that in this way the number of good matching candidates is further drastically reduced, thus saving a lot of time to the dentist.

In an embodiment, determining a limited set of parameters to characterize the tooth inside the bounding box further comprises: determining at least one parameter (e.g. a5, a9) for describing a first embrasure; and determining at least one parameter (e.g. a8, a10) for describing a second embrasure.

When the matching score is determined as a weighted sum, the weight factor of the dimensions are preferably higher than the weighting factors of the embrasures.

In an embodiment, determining a limited set of parameters to characterize the tooth inside the bounding box further comprises: determining a position of a geometric center, or a center of gravity of an existing tooth. It may be useful to store this information as one of the parameters in the index file. When determining a matching score between an existing tooth and a tooth from the 3D digital library, correspondence between their geometric centers or centers of gravity may be taken into account.

In an embodiment, step g) further comprises: allowing a user to select another matching tooth from the limited set of candidate matching teeth, and overlaying the first image with a digital representation (e.g. a contour or a projection) of the selected candidate matching tooth.

According to another aspect, this disclosure also provides a computer program product containing executable instructions which perform a method according to the first aspect, when being executed on a computer device having or being connected to a display, and having or being connected to a pointing device.

According to another aspect, this disclosure also provides a method of dental treatment of a patient, comprising: generating a digital dental design of the oral space using a method according to the first aspect; producing at least one physical object based on said digital dental design; mounting the physical object in an oral space of the patient.

According to another aspect, this disclosure also provides a storage medium comprising a file containing executable instructions which perform a method according to the first aspect, when being executed on a computer device having or being connected to a display, and having or being connected to a pointing device.

According to another aspect, this disclosure also provides a computer arrangement comprising: a computer device comprising at least one processor and a memory, the memory comprising an executable file; a display connectable to, or connected to, or embedded in said computer device, and configured for displaying said facial image; a pointing device connectable to, or connected to, or embedded in said computer device, and configured for receiving user input; wherein the executable file contains executable instructions which perform a method according to the first aspect, when being executed by said at least one processor.

Particular and preferred aspects are set out in the accompanying independent and dependent claims. Features from the dependent claims may be combined with features of the independent claims and with features of other dependent claims as appropriate and not merely as explicitly set out in the claims. These and other aspects will be apparent from and elucidated with reference to the embodiment(s) described hereinafter.

BRIEF DESCRIPTION OF THE DRAWINGS

FIGS. 4A, 4B, 4C, 4D, 4E, 4F, 4G, and 4H collectively show several steps which can be used in embodiments of this disclosure, for obtaining an image (e.g. a normalized image) of an intraoral space as digital input for planning or designing or defining a dental restoration.

FIGS. 6A and 6B collectively illustrate an important insight underlying some of the principles of this disclosure.

FIGS. 6C, 6D, and 6E collectively illustrate how future (or envisioned teeth) can easily and rapidly be designed or defined by merely shifting one or more of the characteristic points of the existing teeth.

FIGS. 7A, 7B, 7C, 7D, 7E, 7F, and 7G collectively illustrate how in embodiments of this disclosure, and based upon an image or scan of an existing tooth in its environment (e.g. in the oral cavity), automatically a limited number of matching teeth can be found in a digital library of teeth.

FIGS. 8A, 8B, 8C, 8D, 8E, 8F, 8G, 8H, and 8I collectively illustrate an example how in embodiments of this disclosure, and based upon an image or scan of one or more existing teeth, a new set of longer teeth can be easily and rapidly be defined, and how a limited number of matching teeth can be found in a digital library of teeth.

FIG. 16A shows a 2D picture or a 2D scan of a patient before dental treatment.

FIG. 16B shows a clinical realistic and photo-realistic 2D picture of how that patient will look like after dental treatment.

FIG. 16C is a line drawing for FIG. 16A.

FIG. 16D is a line drawing for FIG. 16B.

FIGS. 19A, 19C, and 19E are different representations of a first picture. FIGS. 19B, 19D, and 19F are different representations of a second picture.

FIGS. 26A, 26B, and 26C collectively illustrate how the reference frame of the 3D model can be aligned to the reference frame of the head, (albeit indirectly), using the rotated 2D picture of FIG. 23.

FIG. 26A shows illustrates the locations of two particular points in the 2D picture.

FIG. 26B shows the locations of these particular points in a projection of the 3D model.

FIG. 26C illustrates that the projections of three particular points in the 2D image may substantially coincide in a single position in a projection showing a bottom view of the 3D model.

FIG. 32A to FIG. 34C illustrate yet another aspect of this disclosure.

FIG. 32A to FIG. 32C shows a view where the width, the papilla height, the gingival margin curve, etc. of frontal teeth is very well visible, but not for teeth in the back.

FIG. 34C shows how the curvature of the projected curves can be modified by moving some control points.

Figures 1A, 1B:
FIG. 1A shows an example of a person before dental restoration
FIG. 1B shows an example of a person after dental restoration. The restorated teeth are longer than the original teeth.

The drawings are only schematic and are non-limiting. In the drawings, the size of some of the elements may be exaggerated and not drawn on scale for illustrative purposes. Any reference signs in the claims shall not be construed as limiting the scope. In the different drawings, the same reference signs refer to the same or analogous elements.

DETAILED DESCRIPTION

It should be understood that descriptions herein with respect to particular embodiments and with reference to certain drawings are not intended to limit the scope of the appended claims. The drawings described are only schematic and are non-limiting. In the drawings, the size of some of the elements may be exaggerated and not drawn on scale for illustrative purposes. The dimensions and the relative dimensions do not correspond to actual reductions to practice of any embodiment described herein.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to this disclosure, the only relevant components of the device are A and B.

Reference throughout this specification to "one embodiment" or "an embodiment" means that a particular feature, structure or characteristic described in connection with the embodiment is included in at least one embodiment of this disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the appended claims require more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment.

Furthermore, while some embodiments described herein include some but not other features included in other embodiments, combinations of features of different embodiments are meant to be within the scope of this disclosure, and form different embodiments, as would be understood by those in the art. For example, in the following claims, any of the claimed embodiments can be used in any combination.

In the description provided herein, numerous specific details are set forth. However, it is understood that embodiments herein may be practiced without these specific details. In other instances, well-known methods, structures and techniques have not been shown in detail in order not to obscure an understanding of this description.

In this document, the terms "digital database" and "digital library" are used as synonyms.

In this document, the terms "future teeth" or "desired teeth" or "designed teeth" or "newly defined teeth" or "envisioned teeth" or "target teeth" or the like, mean the same. In the context of this disclosure, such expressions may refer to a set of parameters, e.g. a set of points characterising an envisioned tooth, or to a 2D bitmap representation of a tooth found in a digital library corresponding to this set of parameters or points, or to a corresponding physical object (e.g. a veneer), depending on the context.

In this document, the term "transition lines" (of a tooth)" may refer to the upright, e.g. vertical transition from the labial surface of an anterior tooth to the interproximal surface, and may in this document also be referred to by "line angles" or by "reflection lines". Likewise the terms "transition curves" or "reflection curves" refers to such transition which is not linear.

In this document, the "upper teeth" refers to the teeth of the upper jaw, and the "lower teeth" refers to the teeth of the lower jaw of a person.

The "upper curve of the upper teeth" or the "upper curve of the teeth of the upper jaw" is situated near the zenith of these teeth.

The "upper curve of the lower teeth" or the "upper curve of the teeth of the lower jaw" is situated near the incisal edge of these teeth.

The "lower curve of the upper teeth" or the "lower curve of the teeth of the upper jaw" is situated near the incisal edge of these teeth.

The "lower curve of the lower teeth" or the "lower curve of the teeth of the lower jaw" is situated near the zenith of these teeth.

When reference is made to "the lower curve" without specifying which jaw, usually the lower curve of the upper teeth is referred to, unless clear from the context that something else was meant.

The expression "dragging a mouse" means "pressing a button of the mouse device and moving the mouse device while holding the button in a pressed position".

In this document, the term "smile" and "oral space" are used as synonyms, unless clear from the context that something else is meant. The term "smile" may be preferred for example when referring to a frontal image from the outside. The term "oral space" may be preferred for example when referring to adjacent teeth, or to the papilla near a tooth.

Unless otherwise mentioned, the expressions "3D digital scan" and "3D intraoral scan" mean the same.

This disclosure relates in general to methods and techniques and tools, e.g. computer aided techniques and tools for dental restoration, such as for example crowns, bridges, abutments, implants, or veneers. This disclosure relates in particular to computer implemented methods, and/or computer programs and/or software modules to perform one or more of the following:

- to automatically characterize a tooth in its environment, e.g. to characterize a shape and size of a tooth of a patient in an intraoral space, e.g. by means of a limited set of parameters, e.g. by means of a relatively small set of points (e.g. at most 20 points) in a 2D or 3D image,
- to allow a user (e.g. a dentist) to adjust one or more of these characteristics in a simple and efficient manner, e.g. by allowing the user to change one or more of these parameters, e.g. by shifting points in a 2D or 3D image, thereby specifying or defining characteristics of the future teeth (e.g. dentally restored teeth),
- to build a digital database of teeth (e.g. of natural teeth), which database is searchable in a fast and efficient manner,
- to determine a matching score between two teeth, for example an existing tooth in an intraoral space of a patient (on the one hand) and a virtual tooth in a digital database (on the other hand),
- to find a limited number (e.g. at most ten or at most five or at most three) virtual teeth in a digital database having a good match with a particular tooth of a patient, e.g. having a matching score higher than a predetermined value (e.g. higher than 85%, or higher than 90%, or higher than 95%), preferably in a fast and efficient manner,
- to provide a clinically realistic (e.g. what is clinically possible) and a photo-realistic (e.g. not robotic or cartoon-like) 2D picture or 2D image of how a face (or a portion thereof, in particular a smile) of a particular patient will look like after dental treatment, for example (but not limited) to cases where the gingiva will be cut,
- to define and/or generate a 3D-digital representation of one or more dental restorations for a patient, for manufacturing said dental restoration,
- to actually create a 3D physical object for dental restoration, e.g. a veneer or a crown or the like,
- and/or combinations hereof.

The present inventors have many years of experience as dentists, in particular for improving or restoring a "smile" of a patient, an example of which is shown in FIG. 1A and FIG. 1B.

FIG. 1A shows a picture of a person having relatively short teeth. FIG. 1B shows the same person after dental treatment, which in this particular case was a purely cosmetic treatment without surgery. Traditionally, such a treatment typically involves several steps, including:

(a) the design of artificial teeth or artificial teeth portions having a suitable size and shape,
(b) making or producing physical objects, e.g. veneers of about 1 mm thickness, comprising or consisting of ceramics or composite materials, e.g. by 3D printing,
(c) applying, e.g. bonding or gluing said physical objects to the existing teeth of the person.

This is known for many years, and as stated for example in the background section of US patent application US2013/0060532, can be partially supported by CAD programs, in particular step a).

While such CAD programs are very useful, some problems or challenges remain, and other problems arise.

(i) For example, a very important aspect when designing "a smile" is that the end result has to be visually attractive or beautiful or aesthetic. In fact, this is often the only reason why patients start the treatment, but CAD programs or computers in general are not aware of "beauty", and for inter alia this reason, there is a common believe that the choice of how the future teeth should look like, is purely subjective. Some CAD programs therefore allow the user (e.g. the dentist and/or the patient) to select a "nice looking" tooth from a catalogue of digital teeth, which is difficult enough to select from, and moreover, the dentist or patient then has to modify the shape and/or size to make it fit between the other teeth. This process is very time consuming. In fact, the inventors have discovered that there is a first group of dentists who spend a relatively long time (e.g. typically at least 20 minutes) searching in the digital database for a nice tooth, and subsequently spend typically at least another 20 minutes for adjusting the selected tooth to make it fit; and that there is a second group of dentists who always use the same four or five teeth from the entire database, and typically spend at least 30 minutes adjusting them, trying to make them fit, and trying to provide an overall aesthetic smile.

(ii) Another shortcoming that some existing CAD programs have, is that they do not show a photo-realistic picture of how the person will look like after dental treatment, but instead provide a rather robotic or cartoon-like picture. This is especially true for CAD programs based on 3D models. Many patients do not like such result, and do not proceed with the treatment, which is a pity, because the robotic pictures are not what they will really look like after treatment.

(iii) A particular insight that the inventors have learned over the years is that some existing CAD programs do provide a photo-realistic image of the patient after the envisioned treatment, but the image did not always correspond with reality.

Confronted with these technical shortcomings while being passionate about natural beauty, and desiring to help patients who are unhappy with their current dental situation, e.g. with their smile, the inventors came to the insights and ideas and solutions described below.

Before describing the proposed solution(s), one of the insights underlying embodiments herein will be explained with reference to FIGS. 2A, 2B, 3A, and 3B.

Figure 2A:
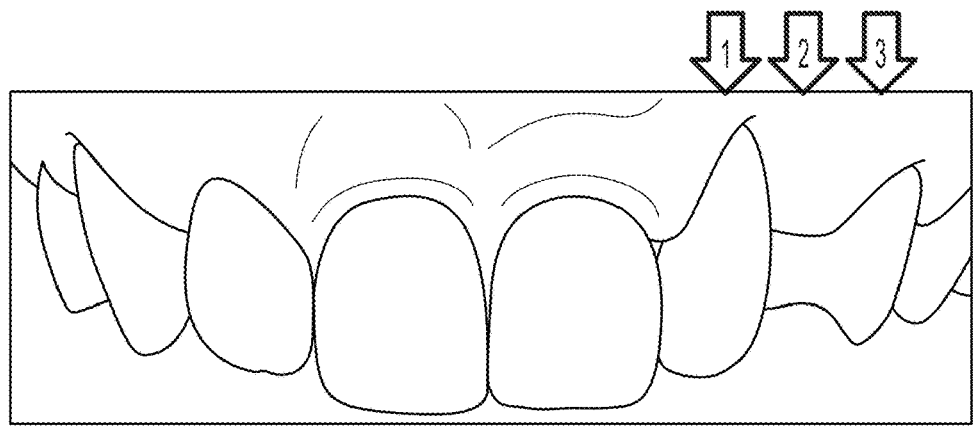
FIG. 2A shows an example of an upper jaw of a person (with a missing tooth) before dental restoration.
Figure 2B:
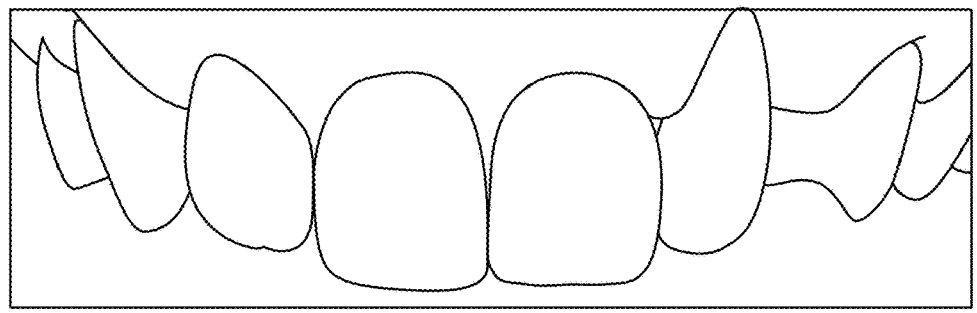
FIG. 2B shows another depiction of the same upper jaw of the person (with a missing tooth) before dental restoration. This smile is generally considered to be not beautiful.

FIGS. 2A and 2B show a grayscale image and a line drawing of an example of an upper jaw of a person having a missing tooth (indicated by arrow 2) and a recess in the gingiva above the left lateral incisor (indicated by arrow 1). Not surprisingly, this person was not happy with her current set of teeth.

Figure 3A:
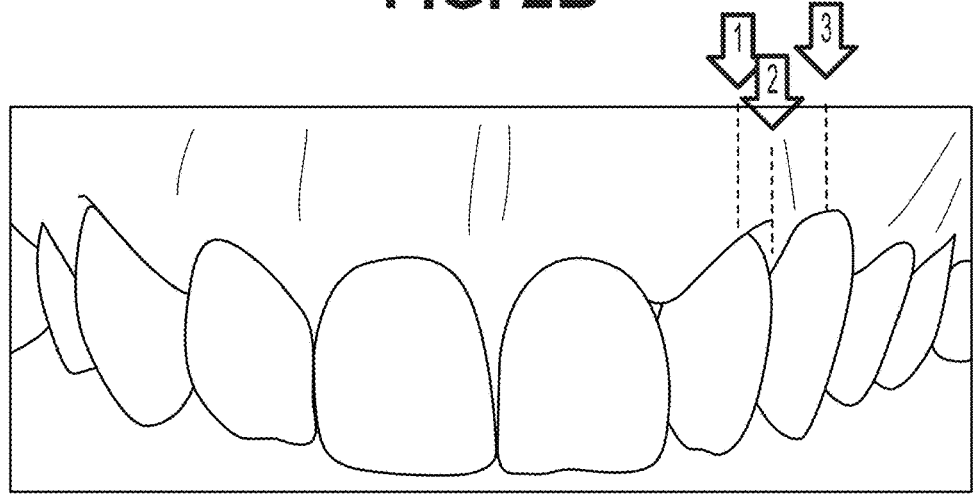
FIGS. 3A and 3B show the upper jaw of the same person of FIGS. 2A and 2B after dental restoration and after surgery. This smile is generally considered to be beautiful.
Figure 3B:
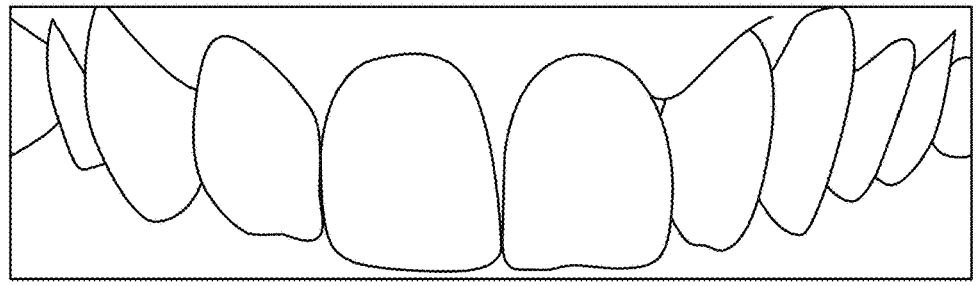

FIGS. 3A and 3B show a grayscale image and a line drawing of the upper jaw of the same person of FIG. 2A after surgery (wherein e.g. tissue was added at the location indicated by arrow 1) and after dental treatment (with e.g. a dental implant at the location of arrow 2, and a plurality of veneers bonded to the other teeth visible in FIG. 3A.

Two of the insights which the dentists had gained before this treatment was performed, and which was taken into account when "designing" the future teeth of this person, or rather when "defining" the future teeth of this person, (which difference will become clear further), are:

(i) that it is possible to add tissue (e.g. by transplantation) to the gingiva above a central line of a tooth (e.g. at arrow number 1), but it is not (normally) possible to add tissue to the papilla (e.g. at arrow number 2); and
(ii) that, in cases where the gingiva is cut (e.g. as shown in FIG. 6A), the papilla will slightly shrink.

As far as is known to the inventors, these insights are not known in the art, but experience has learned that these are very important when designing or defining new teeth of certain patients (where tissue is to be added or removed), e.g. because otherwise a gap or opening will occur between the new teeth, below the shrunk papilla.

It is pointed out that, even though these insights were mainly gained from treatments involving surgery, the solutions presented herein, in the form of computer-implemented methods or computer programs or a searchable database, do not involve surgery, and hence constitute patentable subject matter.

Likewise, even though an ultimate goal of the dentists is to create a beautiful smile for the patient, embodiments herein are not directed to an aesthetic creation per se, but provides technical solutions to technical problems, and thus constitutes patentable subject matter, even if the solution is also beautiful.

FIGS. 4A, 4B, 4C, 4D, 4E, 4F, 4G, and 4H collectively show several (preparatory) steps which can be used in embodiments of this disclosure, for obtaining an image (e.g. a normalized 2D image) of an intraoral space as digital input for further processing, e.g. for designing or defining or planning a dental restoration.

FIG. 4A shows an exemplary 2D image of a smiling person, for example a portrait image captured by a digital image camera.

FIG. 4B shows a subpicture of FIG. 4A after identifying a face midline, after cropping the picture and after rotating the face. This can be done for example using two reference points on the face, e.g. the philtrum and the *glabella*, or the eye centres, or in another suitable way.

FIG. 4C shows how the inner contours of the lips can be defined (e.g. by allowing a user to manually indicate a plurality of points by clicking a mouse), or automatically detected, for example using edge detection techniques, or a combination hereof. The lip contours define an area (e.g. the shaded area in FIG. 4C) which will be updated or partially updated with a visualisation of one or more future teeth (see e.g. FIG. 4G, 15B, 16B, or 17B).

FIG. 4D shows the picture of FIG. 4B, but wherein the intraoral area indicated in FIG. 4C is or can be partially overlaid with one or more future teeth, as will be explained next.

FIG. 4E is an enlarged view of the shaded area shown in FIG. 4C, showing a 2D image of the current clinical situation and an additional grid overlaid over the 2D-image. The grid comprises an upper curve 41 and a lower curve 42 and a plurality of vertical line segments. The upper curve 41 can be used to indicate a (current or future) transition between upper ends of at least some of the teeth and the (current or future) gingiva. The lower curve 42 can be used to indicate a lower end of at least some of the teeth (e.g. the incisal end of some of the upper teeth). The vertical line segments can be used to define substantially rectangular areas or rectangular areas (see e.g. FIGS. 5B and 17A) comprising individual teeth. The picture of FIG. 4E is also referred to herein as the "restorative space".

FIG. 4F shows an example of how the picture of FIG. 4E can be normalized or calibrated, for example based on a distance (in the example 17.3 mm) between incisal embrasures between canines and first premolars, but another distance may also be used. This distance can for example be measured in the mouth using a vernier gauge or a calliper, or can be measured on a gypsum model, or extracted from a 3D STL file, or determined in any other way.

FIGS. 4G and 4H are similar to FIG. 4D and FIG. 4E, but indicate that a user (e.g. a dentist or the patient) can change the position of the upper curve 41 and/or the lower curve 42, to thereby define (e.g. increase or decrease) the height (e.g. the desired height) of the future teeth, for example by dragging some reference points of the curves (e.g. as indicated with circles or squares).

In preferred embodiments of this disclosure, the database contains a plurality of photorealistic 2D pictures of teeth, each with a portion of gingival tissue (at the top) and a portion of papilla tissue (at the sides) and with some amount of shadow (at the bottom). Preferably the visualisation of the future dental situation of FIG. 4G may include overlaying a portion of the picture of FIG. 4B, e.g. a portion of the area indicated in FIG. 4C, using one or more pictures from the database, for example using semi-transparency for pixels comprising tissue information and/or shadow information, and non-transparency for pixels comprising dental information. When actually designing or defining the future smile, the picture of FIG. 4H may further include an overlay of one or more 2D contours of the one or more teeth selected from the library (e.g. as shown in FIG. 7E, 15B, or 17C).

In preferred embodiments of this disclosure, the pictures of FIGS. 4G and 4H are simultaneously shown on a display, and are synchronously updated for each modification made (as will be explained further), for example when replacing one of the existing teeth by a larger tooth from the library. The picture of FIG. 4H may display the original tooth and a contour of the new tooth, while the picture of FIG. 4G may display a photo-realistic 2D image of the new tooth from the library combined with the original picture, for example using semi-transparency.

In embodiments of this disclosure, a user interface (e.g. a graphical user interface) may comprise an area like the one shown in FIG. 4H functioning as the "working area", and also an area like the one shown in FIG. 4G where a photo-realistic image is displayed which can be considered as the "result area". An example of such a user-interface is shown in FIGS. 17B and 17C.

As described above, existing CAD tools typically use 3D models of an entire set of teeth of a person, where an outer surface of a tooth is typically described or defined by a huge number of "finite elements". An advantage of such representation is that it allows (a computer) to accurately describe very complex 3D shapes, but a disadvantage (for human users) is that modifying such a model to meet future teeth requirements (e.g. an envisioned length), moreover in a manner in which the result remains beautiful (as a constraint), is very difficult and very time consuming, and may require training. That is probably why several dentists always use the same four or five model teeth over and over again.

The present inventors took a radically different approach, and asked themselves "what is the point of building or designing artificial 3D teeth models when nature already provides us with thousands of millions (e.g. about 6×10^9) samples of teeth, at least 30% of which are beautiful. The inventors wondered if it would be technically possible to make use of what nature has already "designed", to "digitize and store" a subset of that information in a database, and to "select" suitable teeth from that database when generating a dental design and/or planning a dental restoration. They envisioned that, if the database is sufficiently large, no modification whatsoever would be required, and "design could be replaced by selection". They realised that, while the database is not yet sufficiently large, or for other practical reasons (e.g. storage capacity), it would be good to allow some simple modifications or adjustments (such as scaling). The biggest problem of this idea is "how to find a good matching tooth from the database, in an efficient manner".

As far as is known to the inventors, current CAD-tools do not address this problem. In particular, they do not allow to search a database of digital teeth to find a good match for an existing tooth of a patient, at least not in a highly efficient manner, but instead present the user (e.g. the dentist or patient) with a catalogue of teeth, (typically comprising for example 50 to 100 sets of 10 to 12 types of teeth), from which the user can select one, for example one that subjectively looks beautiful, but then the user still needs to adjust the shape and/or size of the tooth, to make it match the clinical situation.

Confronted with these challenges, the inventors came to the idea of providing a computer implemented method of characterising a tooth by analysing at least one digital representation of said tooth in its clinical environment, the method comprising the steps of:

(a) determining a parameter indicative for a position of the tooth in a mouth, for example an FDI-number, or a number according to another system, e.g. according to the American tooth numbering system; and (b) determining a limited set of parameters (e.g. only about 8 to 12, e.g. about 10 parameters for central incisors and for lateral incisors; only about 5 to 9, e.g. about 7 parameters for canines; and only about 5 to 7, e.g. about 6 parameters for premolars) for describing the tooth in its clinical environment (e.g. with respect to the gingiva at the top of the tooth, and with respect to the papilla's on the left and the right of the tooth).

Figure 5A:
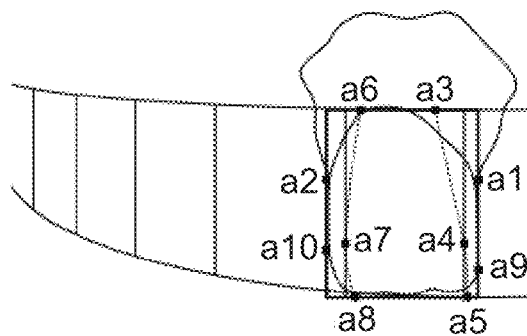
FIGS. 5A, 5B, 5C, 5D, 5E, and 5F collectively show a series of examples of how the shape and size of a central incisor in its environment (in the oral cavity) can be characterised or specified, using a limited number of parameters, e.g. a limited number of characteristic points, according to an aspect of this disclosure.

The limited set of parameters comprises at least two parameter for describing a size of said tooth, for example a height H and a width W (see e.g. FIG. 5B), or a height H and a proportion, or a width W and a proportion, where proportion is defined as width divided by height; and at least one parameter for describing a first papilla height (see for example point a1 in FIG. 5A), and at least one parameter for describing a second papilla height (see for example point a2 in FIG. 5A).

Experiments have shown that surprisingly good results (e.g. in terms of processing speed, and in terms of physically matching or resembling) can be obtained even when using only a very limited set of parameters (e.g. only a relatively small number of characteristic points, e.g. at most 20 points), as opposed to the huge number of points typically used in 3D models based on "finite elements".

It is explicitly pointed out that, preferably, not only characteristics of the tooth itself are taken into account, but also characteristics of tissue in direct contact with the tooth, in particular the papilla's on both sides of the tooth. As described above, it can be avoided that an opening will occur after dental treatment, which would not only negatively influence the beauty of the dental restoration, but would also create a cavity which may be a cause for increased tooth decay.

The limited set of parameters are the clue that enable a database of teeth to be searchable, and as will be described further, also allow a "matching score" to be determined, and also allow software tools to automatically provide a limited set of (candidate) matching teeth, thereby removing a huge burden from the users (e.g. dentists or patients). In addition, this concept also allows the user to adjust the shape and/or size of the future teeth in a very simple manner (e.g. by simply dragging or moving points in a picture). In addition, in case the database also contains 2D pictures, and because the searching in the database is so fast, the software can almost instantly show the results of the adjustments by means of a photo-realistic image. These are the main underlying ideas of this disclosure.

It is noted that this solution goes directly against the common believe that the selection of future teeth is purely subjective. Firstly because the characteristic points can be automatically determined, and secondly, because the "best matching tooth" from the database can be automatically found, according to a predefined matching criterion. This is unprecedented. In preferred embodiments of this disclosure, however, the user has some freedom of choice (e.g. when defining the future length of the teeth), as will be explained further, but once this choice is made, a computer can almost immediately search another best matching tooth (or a limited number of best matching teeth), and can almost immediately visualize how the person will look like after dental treatment. This will be described in more detail in FIG. 14.

In case the parameters are points or positions in a 2D image, each parameter may for example comprise two coordinates (e.g. an X and a Y-coordinate). In case the parameters are positions in a 3D space, each parameter may comprise three coordinates (e.g. an X, Y and Z-coordinate).

The at least two parameters for describing a size of the tooth may be a Height [e.g. in mm] and a Width [e.g. in mm]; or a Height [e.g. in mm] and a Proportion [as a %]; or a Width [in mm] and a Proportion [as a %], where proportion is defined as Width/Height.

The digital representation of the "tooth in its direct environment" may be any suitable digital representation in 2D or 3D, for example a 2D facial picture, or a 3D facial scan, or a 3D intraoral scan, or a frame of a digital 2D movie, or a frame of a digital 3D movie, or a stereoscopic picture, etc.

In embodiments of this disclosure, at least some of the parameters or points or positions are not expressed as absolute values [in mm], but as relative values [e.g. as percentages], for example relative to a rectangle substantially surrounding the currently existing tooth (before dental treatment) or the envisioned future tooth (after dental treatment). An example of such a rectangle is shown for example in FIG. 5B.

In preferred embodiments, the tooth may be characterised by two or four additional parameters for describing a first and a second embrasure, see e.g. points a8 and a5 of FIG. 5A, or points a8, a5, a9 and a10 of FIG. 5A.

The inventors also surprisingly found that the overall shape of the tooth can be described in a highly efficient manner by means of only a few well chosen parameters. In some embodiments based mainly on 2D pictures, the 3D-shape of the tooth can be efficiently described by means of "transition lines" or "transition curves", also referred to herein as "reflection lines" or "reflection curves". Moreover, as will be described further, such lines or curves can be efficiently described by means of only four or only 6 parameters with surprisingly good results. As far as is known to the inventors, this technique is not known in the art. In contrast, what is known, is the use of a single central line (known as "tooth axis"), but experiments have shown that using two lines or curves, especially for the central incisors and the lateral incisors, moreover coded by means of only four or only six points, leads to amazingly good results, while keeping computational efforts low. This is another underlying idea of at least some embodiments of this disclosure.

Embodiments will now be described in further detail, by way of examples, and with reference to FIGS. 5A to 18C.

FIGS. 5A, 5B, 5C, 5D, 5E, and 5F show three examples of how a central incisor can be characterised by means of 10 points a1 to a10. In the three examples, the height H and the width W (see FIG. 5B) of the central incisor is the same, but the papilla heights and the shape of the three exemplary teeth (of FIGS. 5A, 5C, 5D, and 5E) are different.

As shown, a rectangle is drawn, the edges of which are tangential to a contour of the tooth.

The point a1 located on a first vertical edge of the rectangle indicates a first papilla height.

The point a2 located on a second vertical edge of the rectangle indicates a second papilla height.

The points a3, a4 and a5 specify the location of a first transition curve. The point a3 is located on an upper side of the rectangle. The point a5 is located on a lower side of the rectangle. The point a4 is located inside the rectangular area, and its preferably chosen such that the shape of a curve, e.g. a spline or a polynomial or another parametric curve through the points a3, a4 and a5 corresponds relatively well with the actual transition line of the existing tooth as can be seen in the 2D facial picture. In the examples shown in FIGS. 5A, 5B, 5C, 5D, 5E, and 5F, the point a4 is chosen at a predefined distance (d) equal to about 30% of the height H of the tooth, measured from the bottom side of the rectangle, or 70% of the height H of the tooth measured from the top, but of course this disclosure is not limited thereto, and another distance "d" can also be used.

Likewise, the points a6, a7 and a8 specify or indicate the location of a second transition line of the tooth.

Points a6 and a3 indicate the intersection of the transition curves and the upper edge of the rectangle.

Likewise the points a8 and a5 indicate the intersection of the transition curves and the lower edge of the rectangle.

The points a9 and a10, located on the vertical edges of the rectangle, determine the embrasures of the tooth.

Experiments have shown that by using this limited set of only ten points, the shape and size of the central incisor can actually be very well defined. It should come as a surprise to the reader that the tooth actually being a 3D object can be very well characterised by these ten points in a 2D-picture. It is further noted that these points are not merely "abstract points" in a picture, but correspond to real physical locations on a real tooth of a real person, and these points are strategically chosen (except maybe for the points a4 and a7 which could also be chosen slightly higher or lower).

In alternative embodiments, the points a9 and a10 could be omitted from the set, and predefined values for the embrasures could be used instead.

As already suggested above, the position of the points a1 to a11) can be uniquely defined by means of ten numerical values, for example percentages or floating point values or integer values. For example, a value of 20% may be assigned to the parameter a6, meaning that the point a6 is located at a distance x=20% of W from the left edge of the rectangle. Likewise, the other points can also be represented by percentage values relative to the edges of the surrounding rectangle. The position of the tooth in the mouth can be represented for example by an FDI-number, e.g. number in the range from 11 to 48, or a number in the range from 11 to 85 (if baby teeth are also considered). Finally, if two additional numbers, for example H (height) and W (width) are added, or W (width) and P (proportion=W/H), it can be seen that the central incisors can be represented by a limited set of only 13 numerical values.

In fact, for the central incisors, one additional parameter may be added, to indicate whether the tooth is rather "square", or "triangular" or "circular", resulting in a limited set of only 14 parameters.

These 14 parameters may be determined fully automatically using image processing techniques. It is pointed out that a computer implemented method for automatic detection of these characteristic points is not a "mere automation", but has to be recognized as a technical solution to a technical problem of how to efficiently describe the shape and size of a tooth in its clinical environment, because the technique described above is not known in the art.

In an alternative embodiment, the surrounding rectangle is replaced by a virtual beam shaped object having planes tangential to the tooth (except for the upper plane which can for example be chosen as the highest visible point of the tooth, at an edge of the gingiva), and the points a1 to a10 may be defined with reference to the edges and/or corners and/or planes of this beam shape. Other alternatives are of course also possible.

Figure 5B:
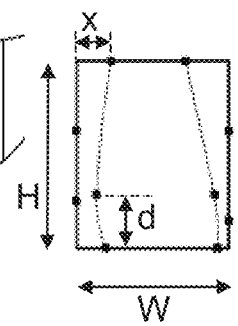
Figure 5C:
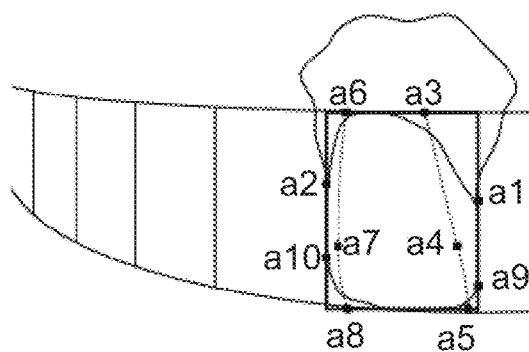
Figure 5D:
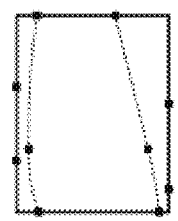

FIGS. 5C and 5D show a second exemplary tooth and its characteristic points on a 2D image.

Figure 5E:
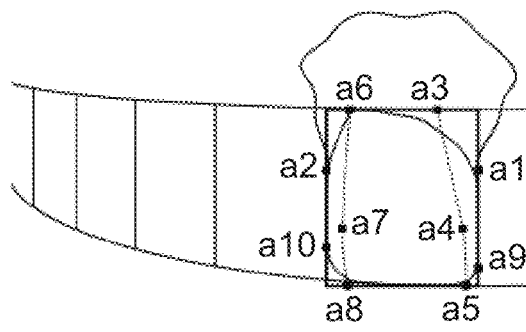
Figure 5F:
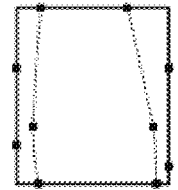

FIGS. 5E and 5F show a third exemplary tooth and its characteristic points on a 2D image.

FIGS. 5A, 5B, 5C, 5D, 5E, and 5F show how central incisors can be characterised by means of a limited set of parameters, e.g. a limited set of less than 20 numerical values, or less than 15 numerical values, for example by means of only 14 numerical values. In a similar manner, also other teeth can be represented by a limited set of less than 15 numerical values. For example,

- the shape of lateral incisors may be characterised by 10 points (or parameters): including 2 points for papilla's, 3+2=5 points for defining one transition curve and one transition line, and 4 points for embrasures, but preferably one point is commonly used for a transition line and for an embrasure, hence 11−1=10 points in total;
- and the shape of canines may be characterised by 7 points (or parameters), because only one transition line is visible from the front, hence 2 points for one transition line, 2 points for papilla's, and 3 points for embrasures (only 1 point for incisal edge), hence 2+2+3=7 points in total;
- and the shape of premolars may be characterised by 6 points (or parameters), because only one transition line is visible from the front, hence 2 points for one transition line, 2 points for papilla's, and 3 points for embrasures, but preferably one point is commonly used for a transition line and the mesial embrasure point (the one towards the canine), hence 2+2+3−1=6 points in total.

But of course, this disclosure is not limited to these specific points or parameters, and other points or parameters may also be used.

It may seem that these numerical values are insufficient to actually produce a 3D physical object (e.g. implant) of a central incisor, but that is not required, because in preferred embodiments of this disclosure, the database not only comprises a 2D image of the teeth, but also a corresponding 3D-model, and once a matching tooth is found based on a matching 2D-image, or rather, based on the limited set of characterizing points of that 2D-image, then the 3D-model can be used for actual production.

In other words, the limited set of parameters described above are sufficient to define a matching tooth for the specific (current or future) clinical environment, and thereby result in a good looking new smile of a patient. It is noted in this respect that the smile of a patient is primarily determined by the "frontal appearance" of the upper teeth.

Thus, in preferred embodiments of this disclosure, not only a 2D-image or 2D-scan is made of healthy teeth stored in the database, but preferably also a 3D scan is made of healthy teeth, (each tooth may be separated from the 3D scan, and prepared by filling the interdental part), and stored in the digital database, along with a 2D image and along with the limited set of parameters, to give the best of both worlds:

- the 2D image and the limited set of parameters allow to search the database in a very efficient way, and allows to show the patient a photo-realistic image of how the dental restoration will look like after dental treatment. Thanks to this efficient search, the process of generating a dental design by moving the position of the characteristic points and/or moving the position of the upper or lower curve, thereby modifying the search parameters for a plurality of teeth, yields almost instantaneous results; and
- the 3D scan allows to actually produce a 3D object of the virtual tooth found in the library once the user (e.g. patient and/or dentist) has made a final selection.

Or stated in other words, the 2D image and the limited set of parameters can be used when defining the future teeth, while the 3D representation can be used thereafter to actually produce physical objects, e.g. veneers.

For completeness, it is noted that an intraoral 3D scan, and separated teeth from an intraoral 3D scan, and production of 3D objects based on such 3D scans are known in the art, and they can advantageously be used in combination with the techniques described above.

FIGS. 6A and 6B illustrate how a user (e.g. a dentist) can (and should) take into account papilla shrinkage when defining the characteristics of the future teeth, as part of a medical treatment which also involves cutting the gingiva. Reasons for cutting the gingiva are not relevant to the present embodiments, but if the gingiva will be cut, the papilla will shrink, and this should be taken into account in the design of the future teeth.

FIG. 6A shows the restorative space (as in FIG. 4H), where the user can shift the upper curve 41 to indicate how far the gingiva will be cut. The points b1 and b2 indicate the current papilla heights, but when planning to cut the gingiva, the points b1 and b2 need to be shifted upwards towards the positions b1' and b2'. This shift may be performed manually or automatically when shifting the upper curve 41. In order to provide a clinically realistic picture of how the patient will look like after the treatment, this papilla shrinkage has to be taken into account, and the future teeth should be defined already taking into account this shrinkage even before it has happened.

FIGS. 6C, 6D, and 6E show examples of other modifications that may be defined by a user (e.g. the dentist or the patient), by merely shifting one or more of the characteristic points in the restorative space image. In the example of FIG. 6D, the size of one of the embrasures is reduced (by shifting the point b9 downwards). In the example of FIG. 6E, the shape of the lateral incisor is adjusted by shifting the point b7 outwardly, thereby actually bending the distal transition curve.

FIGS. 7A, 7B, 7C, 7D, 7E, 7F, and 7G illustrate how, based upon a limited set of parameters, one or more or a limited number of matching teeth can automatically be found in a digital library of teeth.

FIG. 7A shows an example of a limited set of parameters that specify a shape and size of an envisioned or future tooth (in the example a central incisor). As explained above, the limited set of parameters may for example comprise (6 to 10)+3=9 to 13 numerical values (e.g. 6 to 10 percentage values corresponding to positions of characteristic points on a normalized rectangle or beam shape+an FDI number+a width W [e.g. in mm]+a proportion value (e.g. proportion=W/H=75%). For ease of the description, in most drawings, only a rectangle with the 10 points is shown.

The limited set of parameters or the points of FIG. 7A can be seen as "input" for a computer program that has to find a limited number of "matching teeth" in a digital database. In fact, for cases where the user (e.g. dentist) does not want or does not need to change the points, but only wants to find and/or produce a "new tooth" or a "new veneer" having the same size and shape as the existing tooth (e.g. because the existing tooth is broken), the picture or subpicture or scan could be submitted to the computer program as well, and the computer program could determine the position of the points automatically.

The computer program would then search in the digital database for a limited number (e.g. only one, or only 2, or at most 3, or at most 5, or at most 7) matching teeth, based on the limited set of parameters (e.g. the characteristic values). In the example of FIGS. 7A through 7G, the computer program finds three matching teeth, the characteristic points of which are shown in FIGS. 7B, 7C, and 7D. The computer program may present these candidate matching teeth (or a contour thereof) to the user, together with a matching score. FIGS. 15A through 15D show a possible user-interface for presenting the limited set of candidate matching teeth, but of course, embodiments herein are not limited to this particular user interface. Normally, the computer program would automatically preselect the tooth with the highest matching score, but in embodiments of this disclosure the computer program may allow the user to select one of the other candidate teeth (see e.g. optional steps 1405 and 1407 of the method of FIG. 14).

It can be appreciated from FIGS. 7B, 7C, and 7D that it is difficult for a human user to decide which of the candidate teeth looks best on the particular person solely based on the position of the points and transition lines or transition curves. Thereto, the computer program preferably shows a contour of the preselected or selected future tooth over the restorative space representation (e.g. as shown in FIG. 4E or 4H), optionally also with the target or envisioned characteristic points, and optionally also with the characteristic points of the selected candidate tooth, and preferably also with the matching score.

FIG. 7E shows a portion of the restorative space in case the candidate future tooth of FIG. 7B is selected. FIG. 7F shows a portion of the restorative space in case the candidate future tooth of FIG. 7C is selected, and FIG. 7G shows a portion of the restorative space in case the candidate future tooth of FIG. 7D is selected. Typically only one of FIG. 7E, 7F, or 7G would be shown to the user at any moment in time, for example in the manner as shown in FIGS. 15A, 15B, 15C, and 15D, depending on which candidate tooth is selected.

It is noted that in practice a matching score of 74% is not a good match, but these candidate teeth are shown to illustrate how the characteristics of the envisioned (e.g. desired) future tooth may deviate from the characteristics of the candidate matching tooth selected from the database.

While not explicitly shown in FIGS. 7A through 7G, the computer program may be implemented in such a way that the user is allowed to modify the envisioned characteristic points (see e.g. step 1403 and step 1408 of FIG. 14), and in response, the computer program will search the database (see step 1404 of FIG. 14) and present another limited set of best matching teeth from the database. In a prototype of the program, this occurs almost instantaneously (e.g. in less than 0.5 s), thanks to the highly efficient manner of characterizing the tooth, and the ability to search the database for a matching tooth based on these characteristics.

Also, while not shown in FIGS. 7A through 7G, but see for example FIGS. 4G and 4H, or FIGS. 17B and 17C, the computer program may also show a photo-realistic image of the patient with the newly envisioned teeth. In this way, the patient gets an impression of what he or she will look like after dental treatment with this or with these selected and/or modified (e.g. scaled) teeth from the database.

Figure 15A:
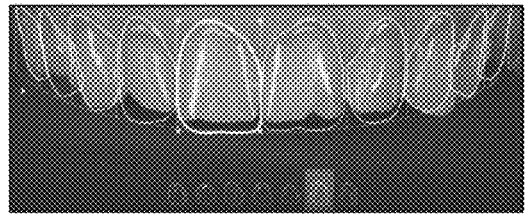
FIGS. 15A, 15B, 15C, 15D, 15E, 15F, 15G, and 15H collectively show exemplary screenshots of a computer program product adapted for performing one or more steps of the computer implemented method shown in FIG. 14, inter alia allowing a user to specify target parameters (of envisioned teeth), for automatically searching the database for matching teeth, for presenting the user with a limited set of candidate matching teeth, and for allowing the user to select another tooth from the limited set of candidate matching teeth.
Figure 15B:
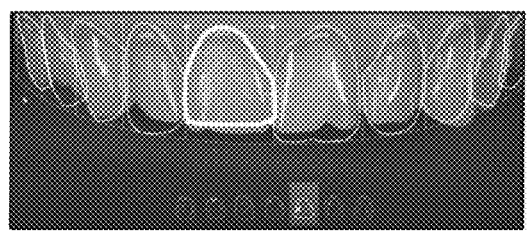
Figure 15C:
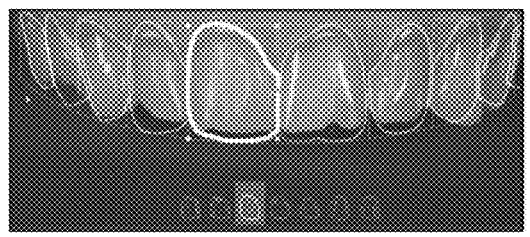
Figure 15D:
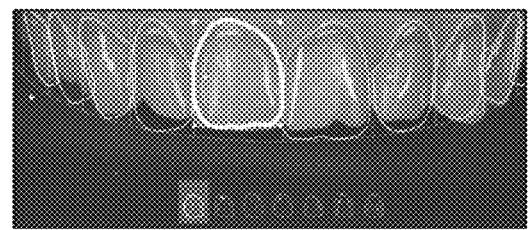
Figure 15E:
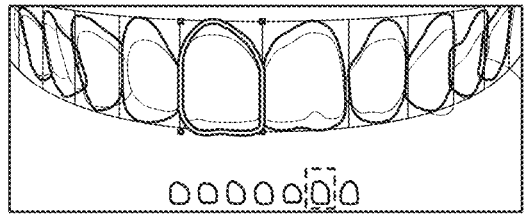
Figure 15F:
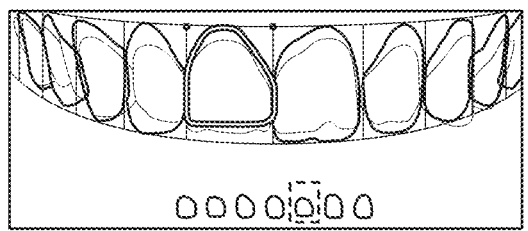
Figure 15G:
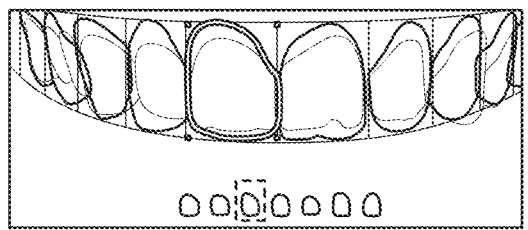
Figure 15H:
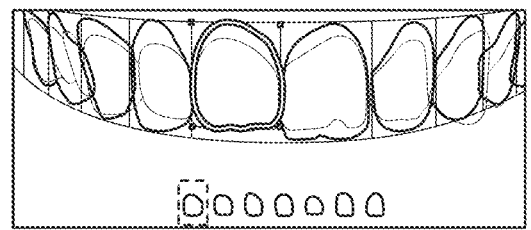

To appreciate the power or the benefit of such a rendering, reference is made to the example of FIGS. 15A and 15B, where the patient can clearly see the current clinical situation before dental treatment (in FIG. 15A) and the future look after dental treatment (in FIG. 15B). If the patient is not happy with the result, he or she can further modify the characteristics of the future teeth, or can cancel the treatment. It is a major advantage of embodiments of this disclosure that the patient can see a clinically realistic picture of how he or she will look like after dental treatment, especially in case the gingiva is cut.

FIGS. 7A through 7G illustrate the situation for a central incisor, but of course, the same principles can also be used for other teeth, in particular the lateral incisors, and the canines, and even the first and second premolars. The smile of a person is primarily determined by these teeth, in that order of importance.

FIGS. 8A, 8B, 8C, 8D, 8E, 8F, 8G, 8H, and 8I illustrate another example similar to FIGS. 7A through 7G. In this example, the future teeth should be longer than the existing teeth, but the "shape" of the teeth should remain unchanged.

This can simply be done by shifting the lower curve 42 slightly downwards in FIG. 8A, where it can be seen that the curve 42 is at a distance from the bottom of the teeth.

As mentioned above, the computer program automatically determines the FDI-number (based on the location on the grid) and the characteristic points shown in FIG. 8C by analysing a digital representation of the oral space (e.g. based on a frontal 2D picture), for example using edge detection techniques.

Based on this input, the computer program can then search the database, and will provide a limited set of candidate matching teeth. (in the example: only three candidates). The candidate tooth which the highest matching score is automatically preselected, in this example: proposal 3 of FIG. 8F. FIG. 8I shows a portion of the restorative space, and optionally the positions of the characteristic points of the existing tooth, and preferably also a contour and also the positions of the characteristic points of the candidate future tooth, along with the matching score (in this case 96%).

While not shown in FIGS. 8A through 8I, a photo-realistic picture of the patient with the future tooth is preferably also shown, e.g. as in FIG. 16B or 17B.

Figure 9A:
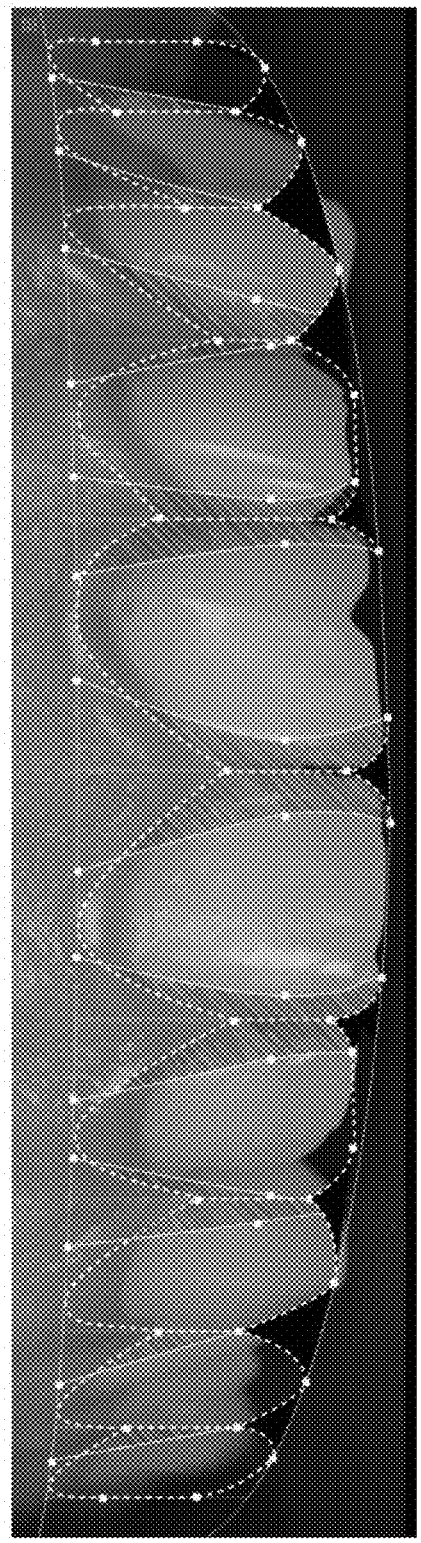
FIGS. 9A and 9B illustrate that a dental restoration based on a limited set of characteristic points can be defined not only for the frontal incisors but also for other teeth, e.g. the lateral incisors and/or the canines and/or the first premolars and/or the second premolars.
Figure 9B:
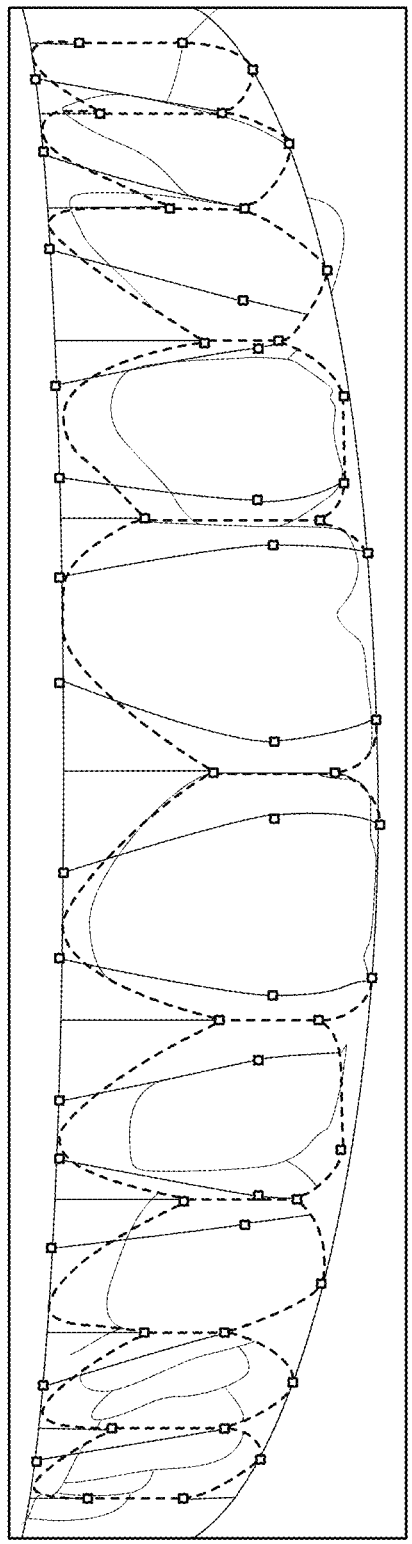

FIGS. 9A and 9B illustrate that a limited set of characteristic points can be defined not only for the frontal incisors but also for other teeth, e.g. for the lateral incisors and/or for the canines and/or for the first premolars and/or for the second premolars. FIG. 9A shows a grayscale image, FIG. 9B shows a line drawing, for illustrative purposes.

It is noted in this respect that this disclosure is mainly concerned with dental restorations related to a beautiful smile, and hence the physical dimensions (e.g. the width), and the shape of the external surface of the teeth are of prime importance. It is noted in this respect that for example veneers typically need to be grinded or polished before they can be adhered to existing teeth.

While not worked out in detail, the principles of this disclosure could also be extended to characterise the 3D shape of teeth, including the position and size and shape of protrusions and cavities in the premolars or molars. This can be accomplished by adding more characteristic points to the teeth to quantify said positions and sizes and shapes. And these characteristic points or values can then be added to a 3D-database to make the database searchable, etc.

Figure 10:
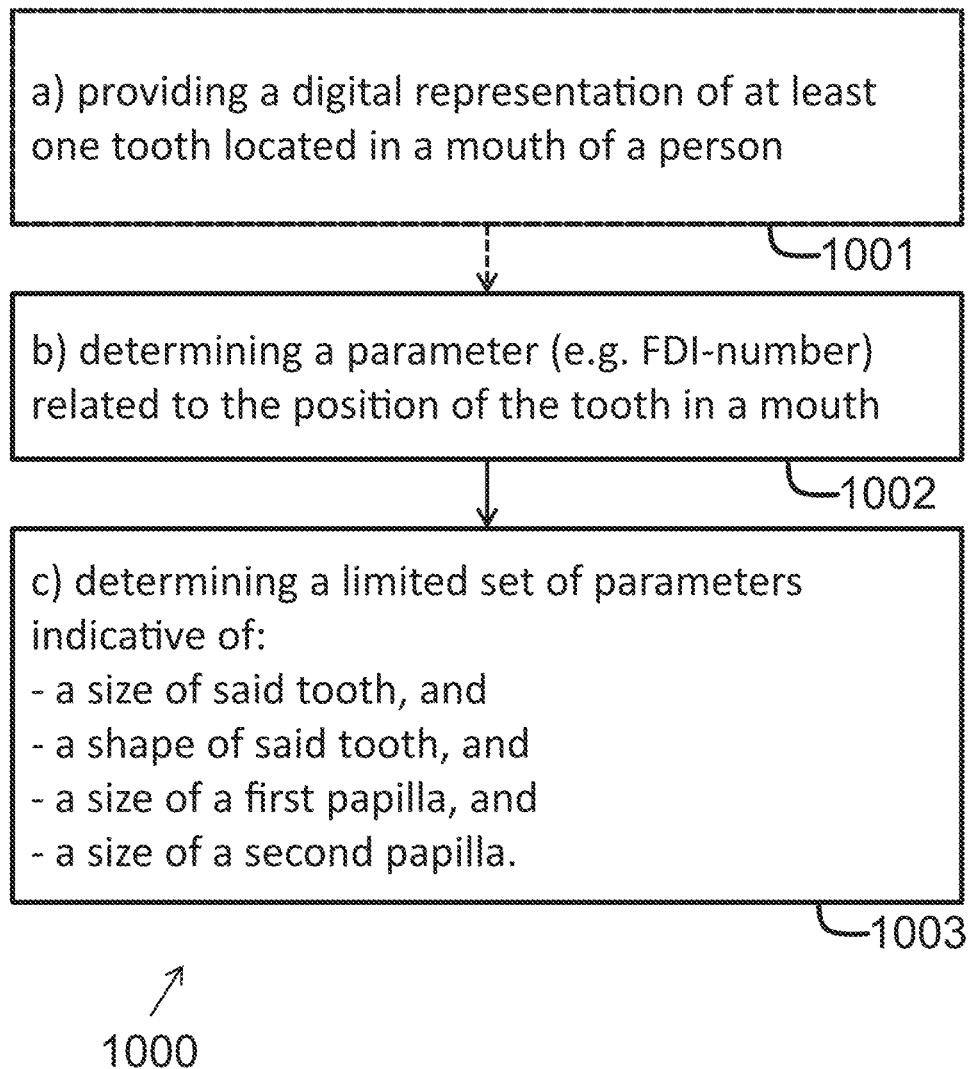
FIG. 10 is a flow chart of an exemplary computer implemented method of characterizing a tooth in an intraoral space, according to an embodiment of this disclosure.

FIG. 10 is a flow chart of an exemplary computer implemented method 1000 of characterizing a tooth in an intraoral space. The method 1000 comprises at least the following steps:

(b) determining 1002 a parameter, e.g. an FDI-number to uniquely define the position of the tooth in the mouth;

(c) determining 1003 a limited set of parameters, for example less than 20 or less than 15 parameters, indicative of: a size of the tooth; and a shape of said tooth; and a size of a first papilla (e.g. the papilla located on the left of the tooth), and a size of a second papilla (e.g. the papilla located on the right of the tooth).

The parameters may comprise for example numerical values, and/or coordinates in a 2D picture, and/or coordinates in a 3D scan, and/or normalized values or percentages (with reference to a normalized rectangle or beam), etc.

Optionally, the method 1000 may also comprise step a) of providing 1001 a digital representation (e.g. a 2D picture and/or a 2D scan or a 3D scan) of at least one tooth located in a mouth of a person. This step may comprise for example: capturing a picture of a person using a digital camera, or using a web-cam, or using a facial scan, or using a 3D intraoral scan, or using a movie-camera; or receiving or retrieving such a picture or image or scan from a network or from an external device, or loading such a picture or image or scan from a storage medium (e.g. a memory stick or a hard disk) or from a network drive, or from the cloud.

As can be understood from the above, these parameters are strategically chosen so as to be able to represent (or at least approach) the size and shape of the tooth and the adjacent papilla's in a highly compact manner.

Step (b) may further comprise: determining at least one parameter (e.g. a9 in FIG. 5A) for describing a first embrasure (e.g. adjacent a left side of the tooth); and determining at least one parameter (e.g. a11) in FIG. 5B) for describing a second embrasure (e.g. adjacent a right side of the tooth).

It was found that by taking the papilla heights into account, a more beautiful result was obtained, or expressed in technical terms: that a gap or opening under the papilla can be avoided.

The at least one parameter for describing a shape of the tooth may comprise exactly two parameters (e.g. a3 and a4, or a3 and a5, see FIGS. 5A through 5F) for describing a first transition line, and exactly two parameters (e.g. a6 and a7, or a6 and a8) for describing a second transition line. Experiments have shown that two pairs of only two parameters are sufficient to describe (or at least approach) the 3D shape of some of the teeth, in particular the canines, the first premolars and the second premolars, or at least a visible surface thereof.

Alternatively, the at least one parameter for describing a shape of the tooth may comprise exactly three parameters (e.g. a3, a4, a5) for describing a first transition curve, and exactly three parameters (e.g. a6, a7, a8) for describing a second transition curve. Experiments have shown that two pairs of only three parameters are sufficient to describe the 3D shape of some of the teeth, in particular the central and lateral incisors.

It is rather surprising that the 3D shape and the corresponding visual appearance of the teeth, can be described by only four or only six parameters, but these parameters allow to search in the database for digital teeth that "look the same or very similar" in a smile.

Figure 11:
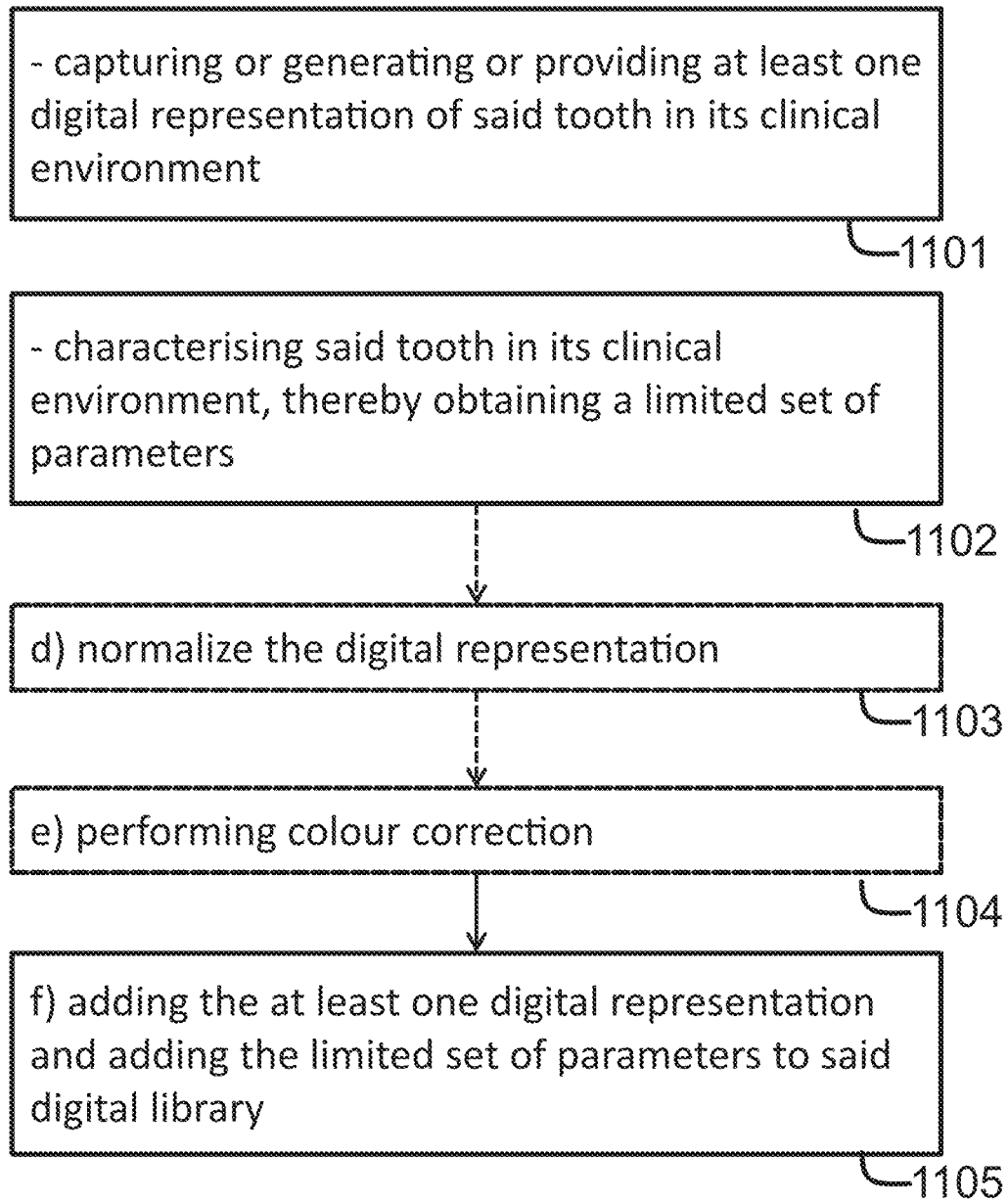
FIG. 11 is a flow chart of an exemplary computer implemented method for building a digital database or digital library of teeth, according to an embodiment of this disclosure.

FIG. 11 is a flow chart of an exemplary computer implemented method 1100 for building a digital database or a digital library of teeth, in particular a library of natural teeth. The inventors realized that by including only healthy, beautiful natural teeth in the library, it is much easier to create a beautiful smile.

The computer implemented method 1100 of building a digital library may comprise the following steps:

capturing or generating or providing 1101 at least one digital representation of said tooth in its clinical environment;

characterising 1102 said tooth in its clinical environment, for example using the steps b) and c) of FIG. 10, thereby obtaining a limited set of parameters;

optionally normalizing 1103 the digital representation, for example by rotating, and/or cropping, and/or scaling;

optionally performing colour correction 1104; It is noted that colour correction may also be performed when extracting the tooth from the database.

(f) adding 1105 the at least one digital representation, and adding the limited set of parameters to said digital library, in a manner wherein the at least one digital representation is linked to the set of parameters.

In some embodiments of this disclosure, at least a 3D scan is captured and stored in the database, and the characteristic points may be derived from the 3D representation itself, or from a 2D projection of said 3D scan.

In preferred embodiments of the present disclosure, both a 2D-picture or 2D scan is captured, as well as a 3D scan, which are both stored in the database, and the characteristic points can be derived from the 2D-picture or 2D-scan.

Figure 12:
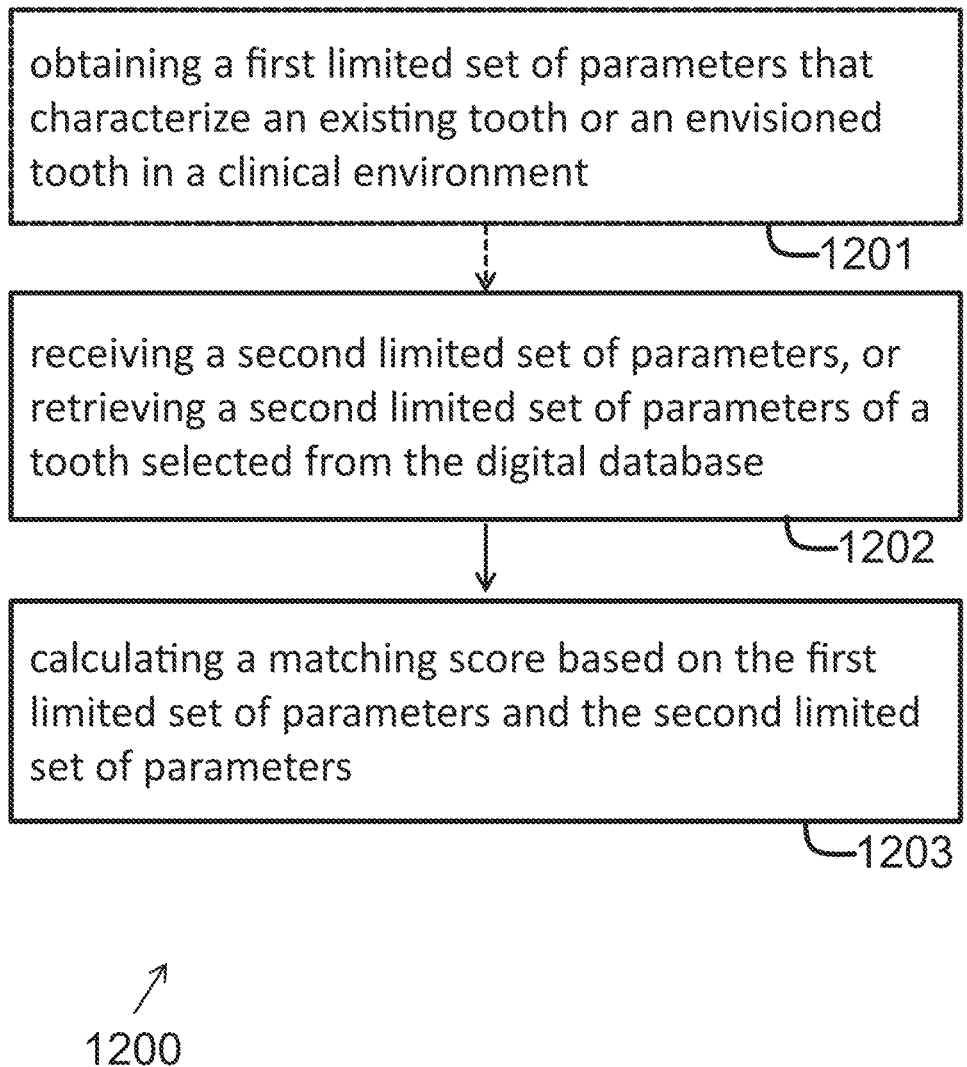
FIG. 12 shows a flow chart of a computer implemented method of determining or calculating a matching score between an existing tooth of a patient, and a virtual tooth from a digital database, according to an embodiment of this disclosure.

FIG. 12 shows a flow chart of a computer implemented method 1200 of determining or calculating a matching score between an existing tooth in an intraoral space of a patient or of an envisioned tooth in said intraoral space of said patient (on the one hand), and a tooth selected from a digital database, e.g. a database as can be generated by the method shown in FIG. 11.

The method 1200 comprises the steps of:

obtaining 1201 a first limited set of parameters that characterize the existing tooth or the envisioned tooth, e.g. using the method of FIG. 10;

receiving a second set of parameters, or retrieving 1202 a second limited set of parameters of the tooth selected from the digital database;

calculating 1203 a matching score based on the first limited set of parameters and the second limited set of parameters.

It is an advantage of this method that the matching score is based on values related to visual aspects, rather than for example merely on volume of objects. While a volume is also a technical term, it is hardly related to aspects of visual appearance or beauty.

In an embodiment, the matching score may be calculated based on a sum or weighted sum of absolute values of differences between corresponding parameters related to size (e.g. Height or Width or proportion) and/or papilla height and/or shape. The matching score may for example be calculated as 100% minus said sum. Preferably the matching score is set to zero ("no match") if the "tooth number" (e.g. FDI number) is different.

In an embodiment, the matching score may be calculated based on a sum or weighted sum of square values of differences between corresponding parameters related to size (e.g. Height or Width or proportion) and/or papilla height and/or shape. The matching score may for example be calculated as 100% minus said sum. Preferably the matching score is set to zero ("no match") if the "tooth number" (e.g. FDI number) is different.

It is an advantage of using such matching score that it is computationally very simple, yet achieves excellent results.

The weight factors may be predefined constants, for example chosen such that:
  (i) the weight factor of the term related to difference in size (e.g. height and/or width and/or proportion) may be larger than or smaller than or equal to the weight factor of the term related to difference of papilla heights; and/or
  (ii) the weight factor of the term related to difference of embrasures may be smaller than the weight factors related to difference in shape; and/or
  (iii) the weight factor of the term related to difference in shape may be smaller then both the weight factor related to size and the weight factor related to difference of papilla height,
  and preferably all of the above.

In a specific embodiment, the weight factor related to difference in size or proportion is equal to about 40%, and the weight factor related to difference of papilla height is equal to about 30%, and the weight factor related to difference in shape (e.g. transition curves) is equal to about 20%, and the weight related to difference of embrasures is equal to about 10%.

In another specific embodiment, the weight factor related to difference in size or proportion is equal to about 30%, and the weight factor related to difference of papilla height is equal to about 40%, and the weight factor related to difference in shape (e.g. transition curves) is equal to about 20%, and the weight related to difference of embrasures is equal to about 10%.

But of course this disclosure is not limited to these particular examples.

Figure 13:
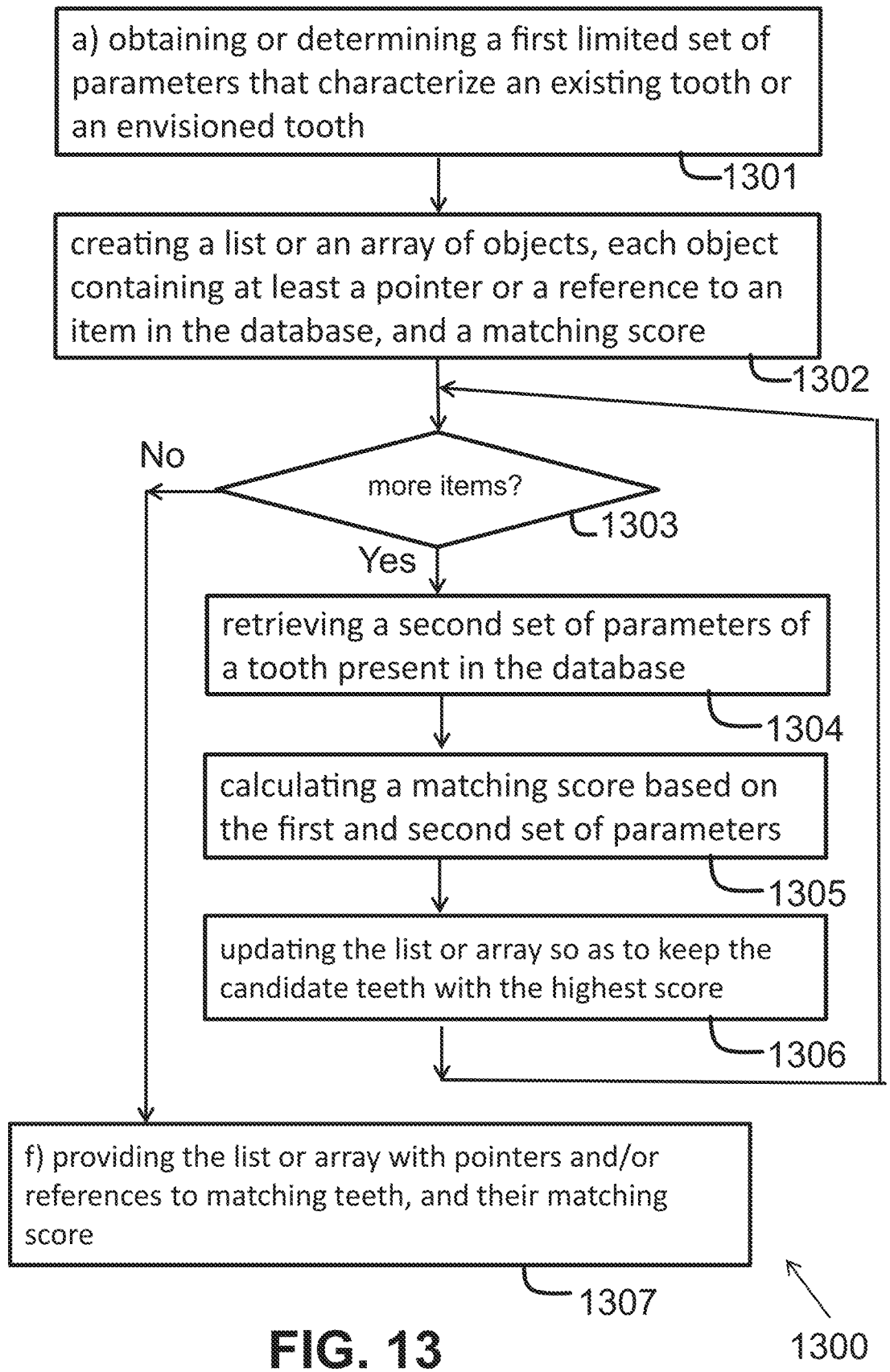
FIG. 13 shows a flow chart of a computer implemented method of searching in a digital database of teeth and selecting a limited set of candidate teeth with the best matching scores, according to an embodiment of this disclosure.

FIG. 13 shows a flow chart of a computer implemented method 1300 of searching in a digital database of teeth for a limited number (e.g. at most ten, or at most seven, or at most five, or at most three, or only two, or only one) matching teeth. The method comprises the steps of:
  (a) obtaining or determining 1301 a first limited set of parameters that characterize the existing tooth or the envisioned tooth, e.g. using the method of FIG. 10;
  (b) creating 1302 a list or an array of objects, each object containing at least a pointer or a reference to items of the database, and a matching score; (and e.g. initialising the list or array);
  For at least a subset of the digital teeth stored in the digital library, performing the steps:
  (c) retrieving 1304 a second limited set of parameters of a tooth present in the digital database;
  (d) calculating 1305 a matching score based on the first limited set of parameters and the second limited set of parameters;
  (e) updating 1306 said list or array so as to keep pointers to the candidate teeth having the highest score;
  (f) providing 1307 the list or array with pointers and/or references to matching teeth, and their matching scores.

It is a major advantage of the limited set of parameters that the database can be searched, and that matching teeth can be found, moreover in a fast and highly efficient manner. This dramatically reduces the time required for planning a dental treatment, e.g. for what is known in the art as "designing a new smile".

Figure 14:
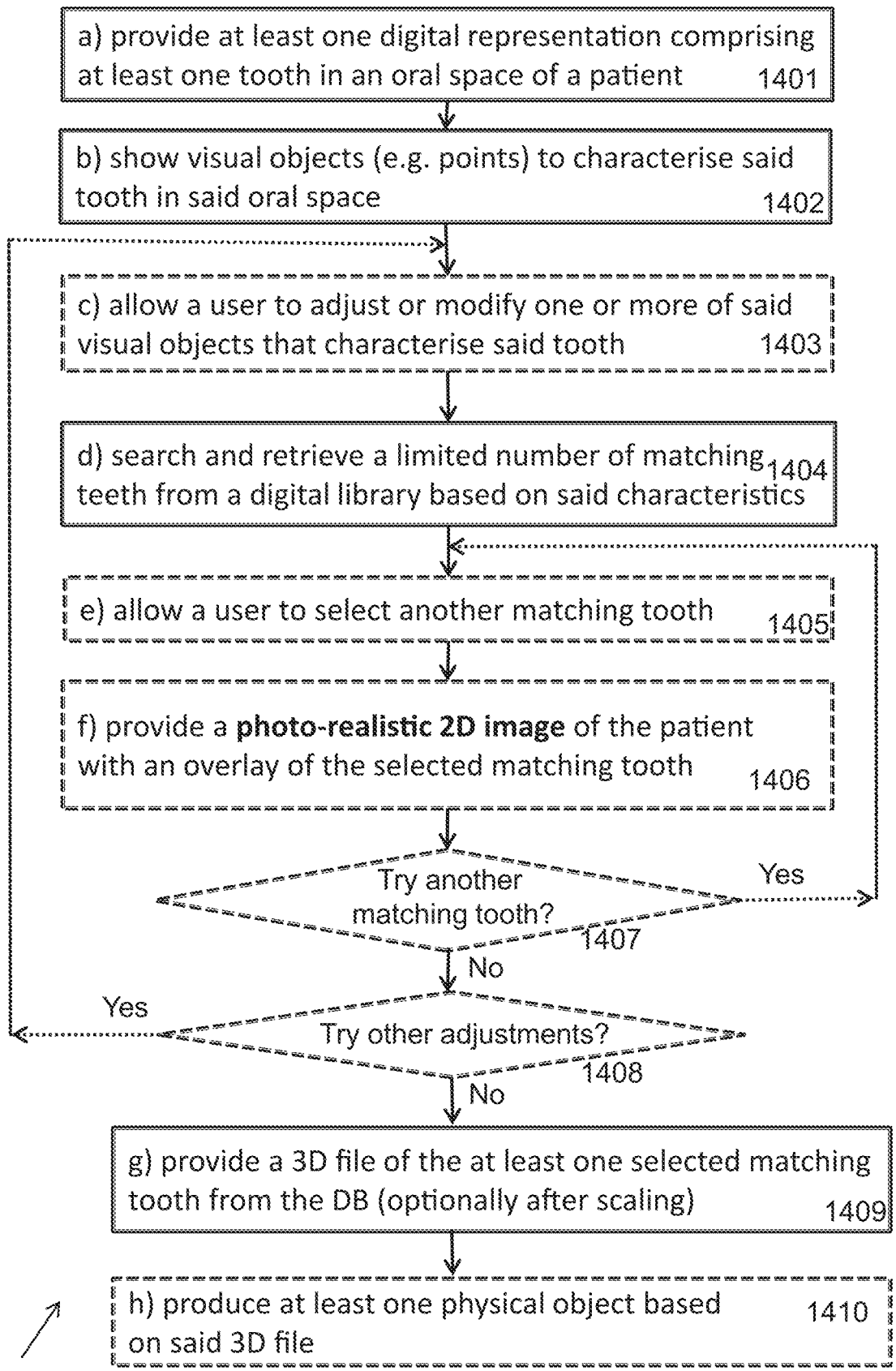
FIG. 14 is a flow chart of a computer implemented method for providing a 3D file for producing a dental restoration automatically or semi-automatically, according to an embodiment of this disclosure. Or stated in other words, a computer implemented method for allowing a user to design or define or plan a dental restoration.

FIG. 14 shows a flow chart of a computer implemented method 1400 for providing a 3D file for producing a dental restoration automatically or semi-automatically. Or stated in other words, a computer implemented method for allowing a user to design or define or plan a dental restoration. The method comprises the steps of:
  (a) providing 1401 at least one digital representation of at least one tooth in an oral space of a patient, for example providing one or more picture(s) and/or scan(s), for example a 2D frontal picture, and/or a 3D facial scan, and/or a 3D intraoral scan, etc.;
  (b) showing 1402 a plurality of visual objects (e.g. a grid and/or points) to characterise said at least one tooth in said oral space;
  (c) optionally allowing 1403 a user to repeatedly 1408 adjust and/or modify one or more of said visual objects that characterise said tooth;
  (d) searching and retrieving 1404 a limited number of candidate matching teeth from a digital library of teeth, based on said characteristics, for example using the method illustrated in FIG. 13;
  (e) optionally allowing 1405, 1407 a user to repeatedly select another matching tooth from the limited set of candidate matching teeth;
  (f) optionally providing 1406 a photo-realistic 2D image of the patient with an overlay of the selected matching tooth, optionally after scaling;
  (g) providing 1409 a 3D-file of the at least one selected matching tooth, optionally after scaling.

This method is directed to a computer implemented method that for example starts from a 2D-picture (e.g. as in FIG. 4A), shows a grid and/or characteristic points (e.g. as shown in FIGS. 5A through 8I), allows a user to modify the characteristic points to thereby specify how the future teeth should look like, provides the user with a limited number of (good) matching results from the database as the user modifies some characteristic points (e.g. as shown in FIGS. 8A through 8I), and finally provides a 3D-file allowing the envisioned tooth to be manufactured.

The method may further comprise step h) of producing at least one physical object based on said 3D file, for example by rapid manufacturing techniques, such as e.g. by 3D-printing.

The end result of this method is a physical object.

FIGS. 15A, 15B, 15C, and 15D show screenshots of an exemplary user interface of a computer implemented method adapted for performing one or more steps of the method shown in FIG. 14, in particular steps b), c), d) and e). In this example, the computer program searches the database, and retrieves the seven best matching candidates, and shows a miniature picture or a miniaturized contour of the candidate matching teeth, preferably each with a matching score, from which the user (e.g. the dentist) can select one, a contour of which is subsequently rendered in the picture representing the restoratory space.

FIGS. 15E, 15F, 15G, and 15H are line drawings of FIGS. 15A, 15B, 15C, and 15D for illustrative purposes.

While not explicitly shown in FIGS. 15A through 15H, preferably also a photorealistic image of the patient is provided with a color picture of the one or more tooth selected from the database (not only the contour), an example of which is shown in FIG. 16B. This photorealistic 2D-picture is preferably provided on the same screen or on the same display as the picture showing the restoratory space, for example side by side as shown for example in FIGS. 17B and 17C.

FIG. 16A shows a 2D picture or a 3D facial scan of a patient before dental treatment, and FIG. 16B shows a clinical realistic and photo-realistic 2D picture of how that patient will look like after dental treatment, for example after the selected teeth or veneers or the like are produced, and bonded to the existing teeth.

FIGS. 16C and 16D are line drawings for FIGS. 16A and 16B, respectively, for illustrative purposes.

Figure 17A:
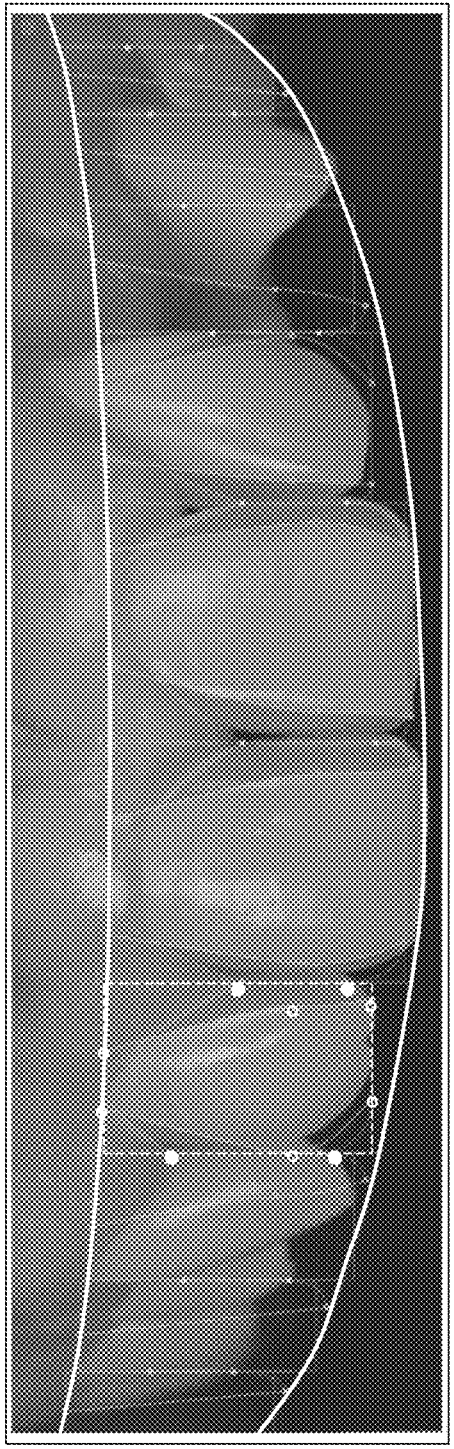
FIG. 17A shows a 2D picture of the teeth shown in FIG. 2A, overlaid with a grid, as can be used in embodiments of this disclosure.
Figure 17B:
FIG. 17B shows a photo-realistic picture of how the patient will look like after dental treatment.
Figure 17C:
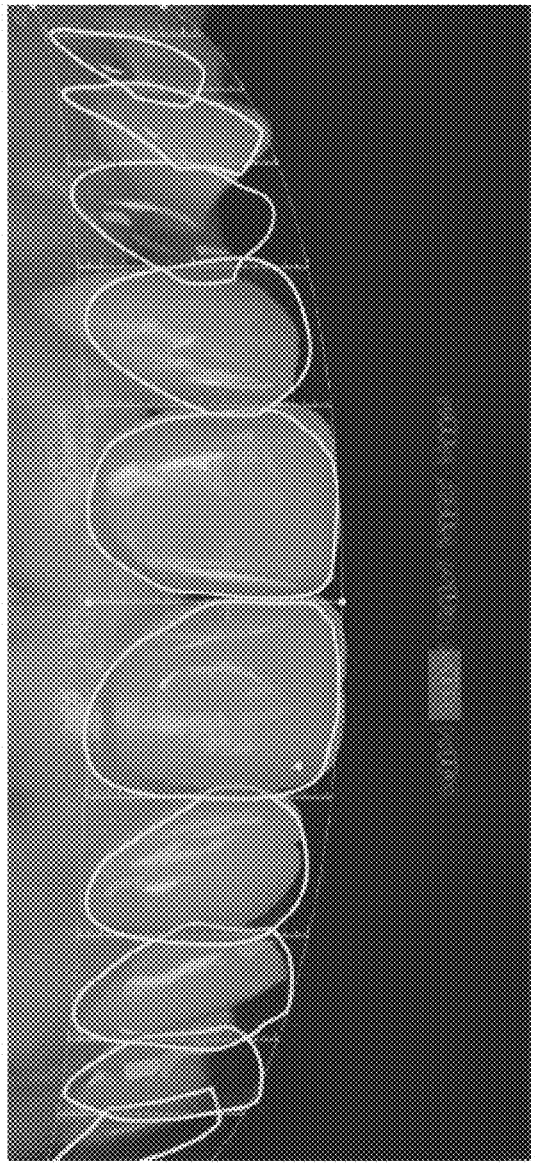
FIG. 17C shows another 2D picture of the teeth shown in FIG. 2A, overlaid with a grid, as can be used in embodiments of this disclosure.

FIGS. 17A and 17C show a 2D picture of the teeth shown in FIG. 2A, overlaid with a grid, as described above.

FIG. 17A shows the restoratory space based on a frontal 2D picture of the patient, with the addition of a grid (as described in FIGS. 4A through 4H). Characteristic points for each tooth are automatically determined by the computer program, and shown to the user. The user can optionally modify the position of one or more of these points.

FIG. 17C shows the restoratory picture with multiple contours of best matching teeth for each particular location. The best matching teeth retrieved from the library may come from different people. What is shown is the automatic proposal (or preselection of teeth) made by the computer program product for each of the ten teeth. The user can simply accept this proposal, or can select a different matching tooth for one or more of the teeth individually, as described above.

FIG. 17B shows a photo-realistic picture of how the patient will look like after dental treatment. As can be appreciated, using methods according to this disclosure, the poor clinical situation illustrated in FIGS. 2A and 2B, can be converted into the beautiful smile shown in FIGS. 3A, 3B, and 17B.

Figure 18A:
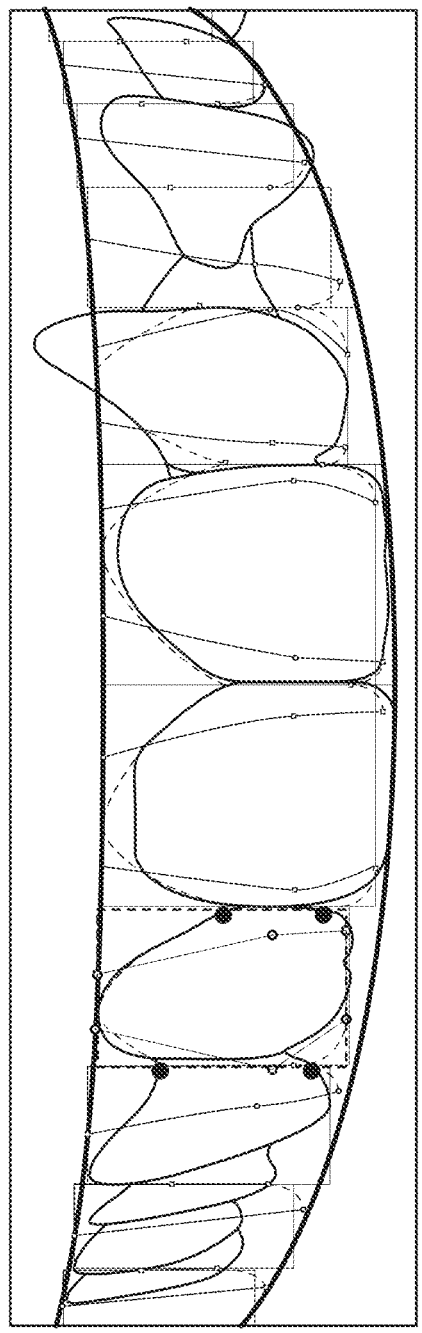
FIG. 18A is a line drawing for FIG. 17A.
Figure 18C:
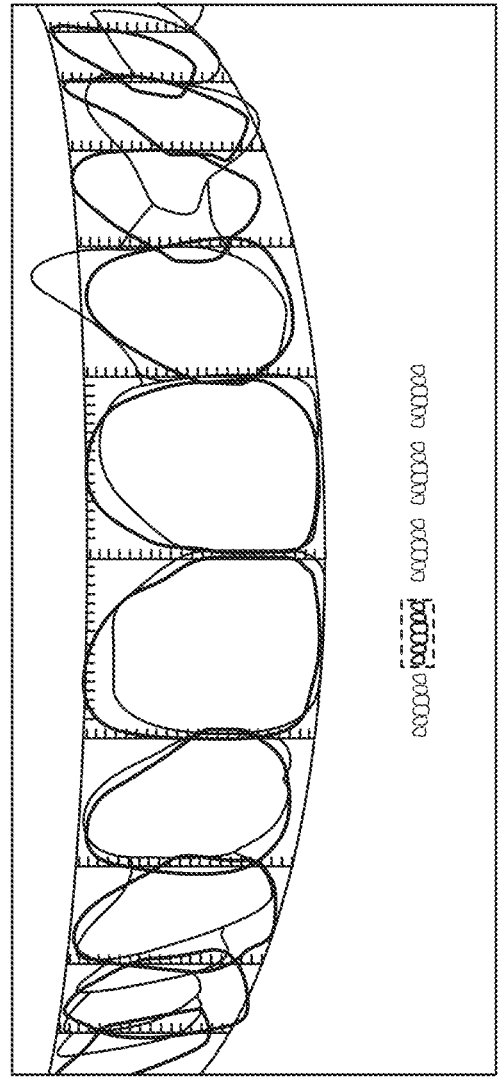
FIG. 18C is a line drawing for FIG. 17C.
Figure 18B:
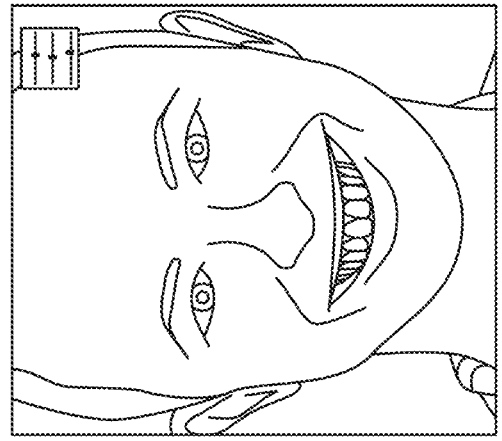
FIG. 18B is a line drawing for FIG. 17B.

FIGS. 18A, 18B, and 18C are line drawings for FIGS. 17A, 17B and 17C, respectively, provided for illustrative purposes.

FIGS. 19A, 19B, 19C, 19D, 19E, 19F and 20 illustrate another aspect of this disclosure, mainly related to movement of the "lower curve" 1902. The "lower curve" was already described above, for example in FIG. 4H. The lower curve may be used as a "drawing reference" when modifying the length of individual teeth, e.g. to make sure that the lengths of the individual teeth are more or less consistent.

The inventors came to a further insight that the generation of the dental design can be further improved. Indeed, rather than using the lower curve 42 merely as a comparative reference when manually increasing or decreasing the height of individual teeth, they realized that the time required to generate a dental design can be further reduced by adjusting the height of at least two teeth or all teeth of the upper jaw simultaneously. When taking into account that in this disclosure individual teeth are individually optimized, such functionality is far from trivial. It is largely thanks to the very fast search algorithm, which is based on the characterisation of teeth as described above, and indexing the database based on that characterisation, e.g. by using an index based on the limited set of parameters, that such improvement is feasible.

To get an idea of the order of magnitude of the speed, tests were performed using a digital library containing more than 1100 digital teeth, and the time required to find five best matching teeth for all twelve teeth of the upper jaw was a value in the order of about 5-25 msec. For completeness it is noted that the measurement did not take into account the time for retrieving the actual digital representation (e.g. pictures) of these teeth from the database, and overlaying these pictures over the smile of the patient, but the reader will appreciate that the search is so incredibly fast that it allows an almost instant update of the picture in response to a modification of the lower curve.

In an embodiment, the smile of the patient is dynamically updated when changing the lower curve, for example by dragging a visual object or marker located on the lower curve 1902 using a pointer device, e.g. using a mouse device.

Figure 19A:
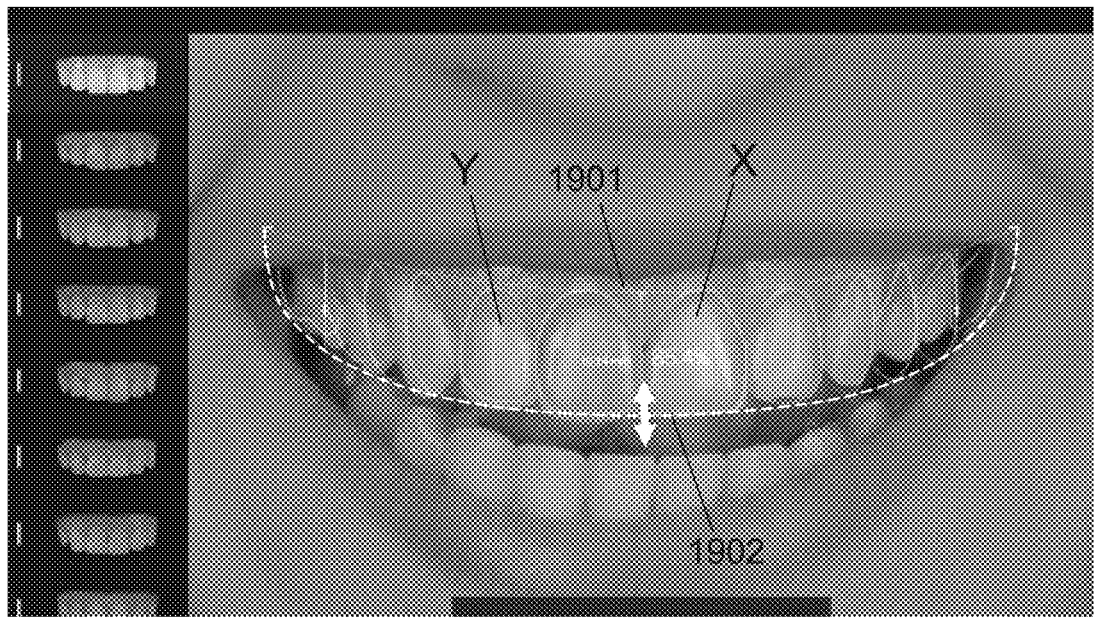
FIGS. 19A, 19B, 19C, 19D, 19E, and 19F collectively illustrate how adjustment of a position and/or shape of the "lower curve" can be used to define and/or adjust the length of multiple teeth in a highly efficient manner.
Figure 19B:
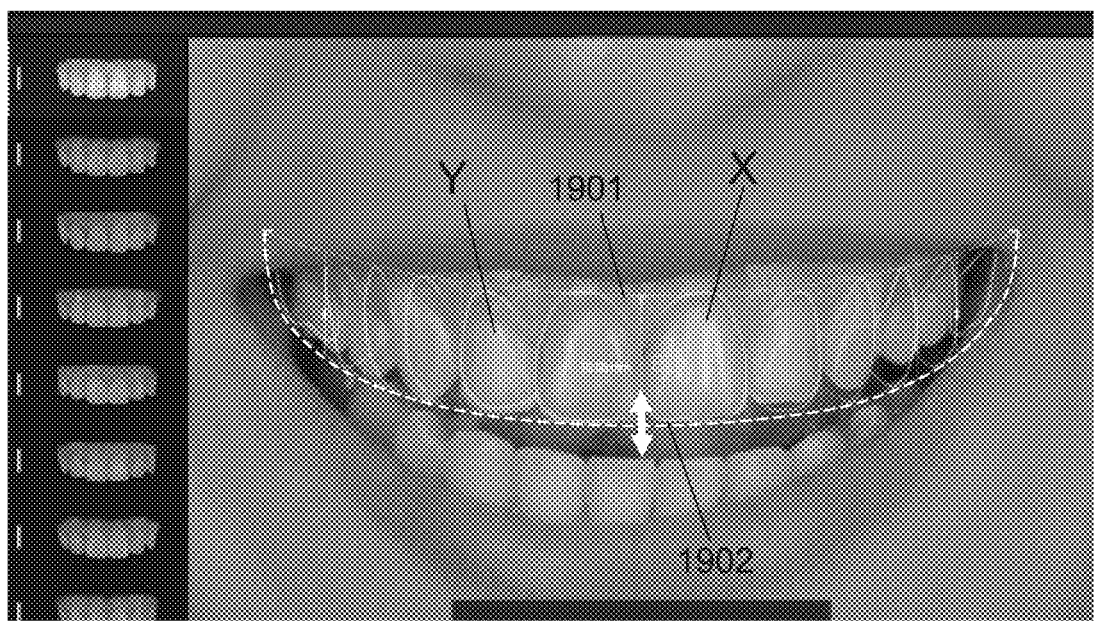

FIGS. 19A and 19B illustrate what happens in embodiments of this disclosure in which this functionality is implemented. While it would be much easier to demonstrate in a short video-clip how "dragging of the lower curve works", unfortunately patent applications are limited to still pictures. FIG. 19A shows a screenshot of the video-clip taken at a first moment in time, and FIG. 19B shows a screenshot of the video-clip taken at a second moment in time. The time interval between the two pictures was chosen relatively long for illustrative purposes, namely to illustrate two effects that typically occur when "dragging the lower curve".

Consider tooth X in FIG. 19A, where a best match was found in the database having a matching score of 85.4%. When the "lower curve" 1902 is moved downwards, the parameters of the tooth X are adjusted accordingly, but this did not result in another best matching tooth for tooth X. The same tooth from the library was still considered to be the best match for tooth X, despite the fact that the matching score decreased to 82%. This is still true in FIG. 19B. It was only later, when the lower curve 1902 was moved further, that another best matching tooth was presented for the patient tooth X.

Consider tooth Y in FIG. 19A, where a first best matching tooth was found in the database for this position of the lower curve 1920, but where another best matching tooth was found when the lower curve 1902 was moved to the position of FIG. 19B, as can be appreciated from the different contours of the best matching tooth for tooth Y in FIGS. 19A and 19B.

In practice, when slowly dragging the lower curve 1902, these two effects occur for all the teeth, resulting in the various teeth remaining unchanged for a certain period, and then suddenly change shape, seemingly in a pseudo-random manner.

Of course, the technical description in this document is different from a real user experience, who will "see" combinations of relatively short teeth as the lower curve 1902 is moved upwards, and various combinations of relatively long teeth as the lower curve 1902 is moved downwards, and various combinations in between, allowing the user to select an appropriate length.

While dragging the lower curve, the algorithm will typically automatically select the best matching tooth, and show this tooth in overlay. After dragging the lower curve 1902, the user may further adjust one or more teeth individually, e.g. by moving some of its characterising points, or by selecting another candidate tooth from the limited list of teeth for the tooth concerned.

FIGS. 19A and 19B are grayscale pictures, showing photo-realistic images.

Figure 19C:
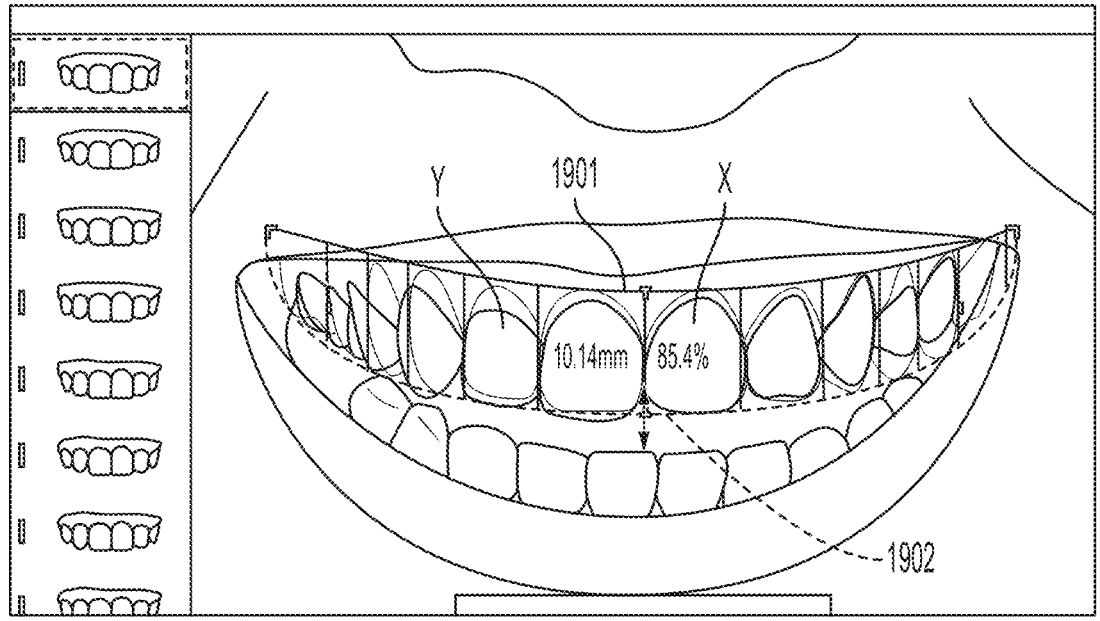
Figure 19D:
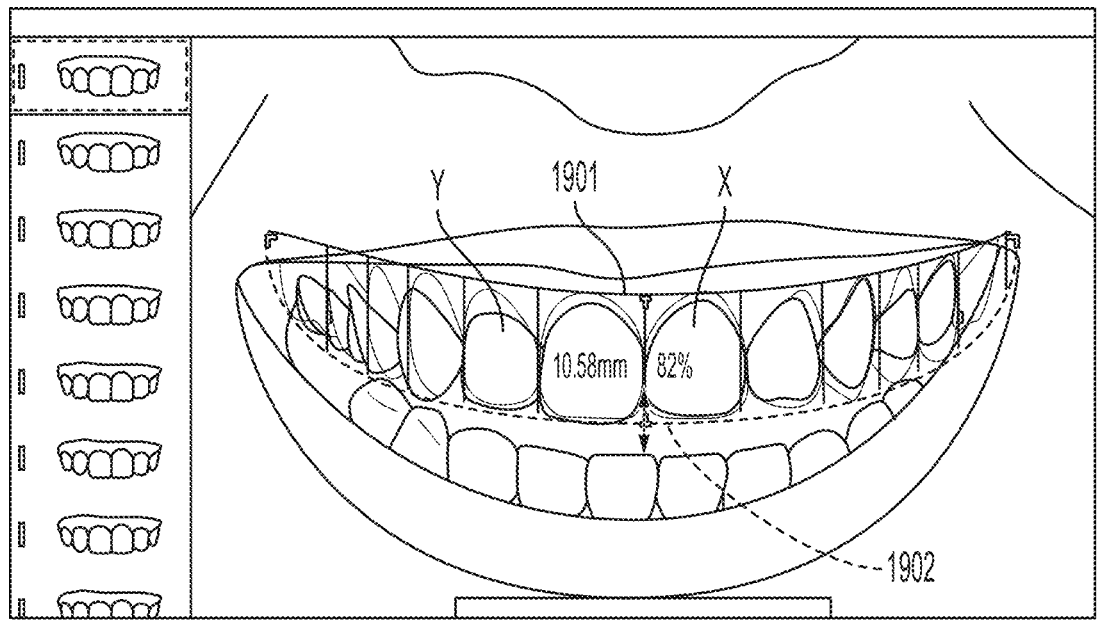

FIGS. 19C and 19D show a sketch of the grayscale pictures of FIGS. 19A and 19B, better illustrating the contours of the teeth.

Figure 19E:
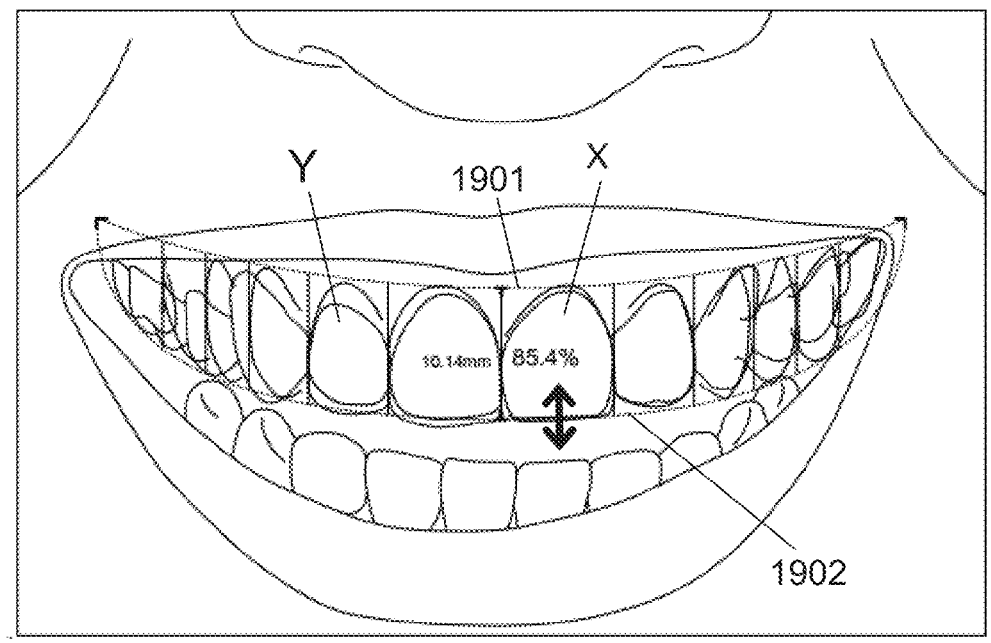
Figure 19F:
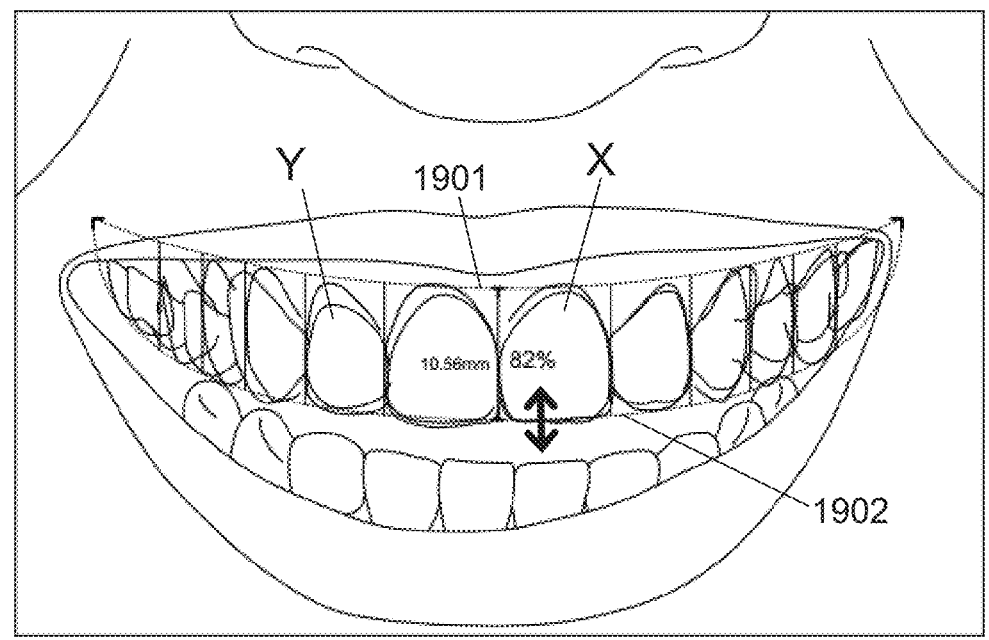

FIGS. 19E and 19F are "line drawings" of FIGS. 19C and 19D. FIGS. 19C, 19D, 19E, and 19F are provided for illustrative purposes.

In the examples of FIGS. 19A, 19B, 19C, and 19D, more than five combinations of "matching candidates" are shown on the left part of the picture, but of course this disclosure is not limited hereto, and the methods herein will also work if less than five matching candidates are searched or shown, for example only four, or only three, or only two.

It is also noted that the candidate matching teeth (for a particular tooth position) may be presented to the user in a different way, for example in a manner similar to FIGS. 16A, 16B, 16C, and 16D, or in another suitable manner.

Figure 20:
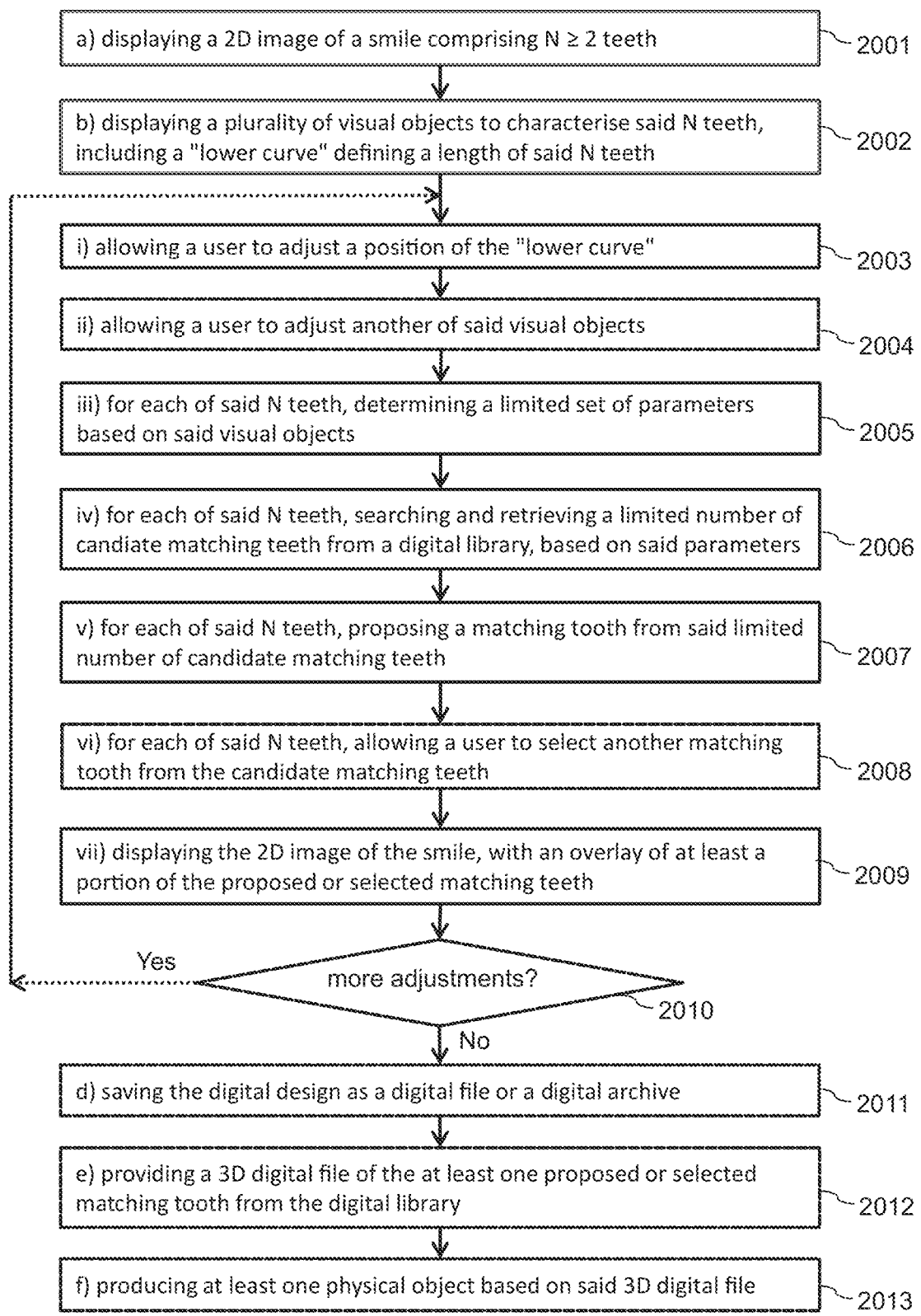
FIG. 20 shows a flowchart of a method of generating a dental design, as proposed by this disclosure.

FIG. 20 shows a flowchart of a method of generating a dental design, as an embodiment of this disclosure. The method 2000 comprises the following steps:

(a) displaying 2001 a 2D image of a smile comprising a plurality of at least two or at least four or at least six teeth, e.g. on a display device such as an LCD display. The image may be captured by a digital camera. The at least two teeth may be two frontal incisors of the upper jaw.

(b) displaying 2002 a plurality of visual objects (e.g. one or more lines, markers, a grid comprising an upper curve and a lower curve of the upper teeth and a plurality of vertical line segments, etc.) to characterise said plurality of at least two teeth in said smile. The plurality of visual objects includes a "lower curve" 1902 defining a length of said plurality of at least two teeth. The "lower curve" is preferably situated at or near an incisal edge of the upper teeth. The visual objects may characterize for example an overall size and/or shape and/or curvature of the at least two teeth. The visual objects may be the set or a subset of the visual objects described in FIGS. 5A through 8I, but the present embodiment is not limited thereto, and other visual objects may also be used (c) performing at least once the following steps:

(i) allowing 2003 a user (e.g. a dentist) to adjust a position of the lower curve 1902, e.g. in order to increase or decrease the length of said plurality of at least two teeth;

(ii) optionally allowing 2004 a user to adjust one or more other of said visual objects, e.g. in order to increase or decrease a width, or to change a lateral position, or to change the shape of one or more of said teeth;

(iii) for each of said at least two teeth, determining 2005 a limited set of parameters based on said visual objects;

(iv) for each of said at least two teeth, searching and retrieving 2006 a limited number of candidate matching teeth from a digital library of individual teeth, using the limited sets of parameters of each tooth, and using a matching score for each tooth individually, e.g. in the same way or in a similar way as described in FIG. 5A or 8I. The digital library is preferably indexed for allowing a fast search. The index file is preferably stored locally, e.g. on a local storage device or a local memory device, e.g. on a memory stick, or on a hard disk of a computer on which the algorithm is being executed. The digital images of the digital library may be stored on a local storage device, or on a network drive, or in the cloud;

(v) for each of said at least two teeth, proposing 2007 a matching tooth from said limited number of candidate matching teeth, e.g. proposing the best matching tooth from said candidate matching teeth. The limited set of candidate teeth may for example be presented as shown on the left side of FIG. 19C, where the upper subpicture 1911 shows a downscaled version of the smile of the patient with twelve best matching teeth shown in overlay in their respective positions, the second subpicture 1912 shows a downscaled version of the smile of the patient with twelve second best matching teeth shown in overlay in their respective positions, etc.

(vi) optionally, for each of said at least two teeth, allowing 2008 a user to select another matching tooth from the candidate matching teeth, e.g. by clicking on one of the teeth in one of the subpictures on the left of FIG. 19C;

(vii) displaying 2009 the 2D image of the smile, with an overlay of at least a portion of the (automatically) proposed or (manually) selected matching teeth, preferably as a relatively large picture. In some embodiments, the proposed or selected matching teeth are not scaled. In other embodiments, the proposed or selected matching teeth are scaled in only one direction (e.g. only vertical), or are scaled in two directions (e.g. vertically and horizontally) to further improve the matching score. The scaling factor may be a value in the range from 90% to 110%.

(d) optionally 2011 saving the digital design as a digital file or a digital archive, e.g. by saving at least the position of the lower curve 1902, and preferably also the positions of the plurality of visual objects and preferably also a reference in the digital library to the proposed or selected matching teeth, and/or by a copy thereof (e) optionally providing 2012 a 3D digital file of the at least one proposed or selected matching tooth from the digital library, with or without scaling;

(f) optionally producing 2013 at least one physical object based on said 3D digital file, e.g. by 3D-printing.

FIGS. 21 through 30 illustrate another aspect of this disclosure. This aspect will be mainly explained and illustrated to generate a design for upper teeth, but this disclosure is not limited thereto, and the same principles can also work for the lower teeth, mutatis mutandis. This aspect uses a digital intraoral scan (to digitize a space inside the mouth of a patient) and a facial image (to digitize a portion of the face and a portion of the smile). The facial image may simply be a 2D digital image (e.g. a JPEG picture) captured by a digital camera, or may be a digital representation (e.g. a projection) derived from a facial scan. In order to keep the description simple, the intraoral scan will be referred to as "3D digital scan" or "3D image" or the like, while the "facial image" will be referred to as "2D image", but as explained, this disclosure is not limited to 2D images obtained from a 2D digital camera.

Figure 21:
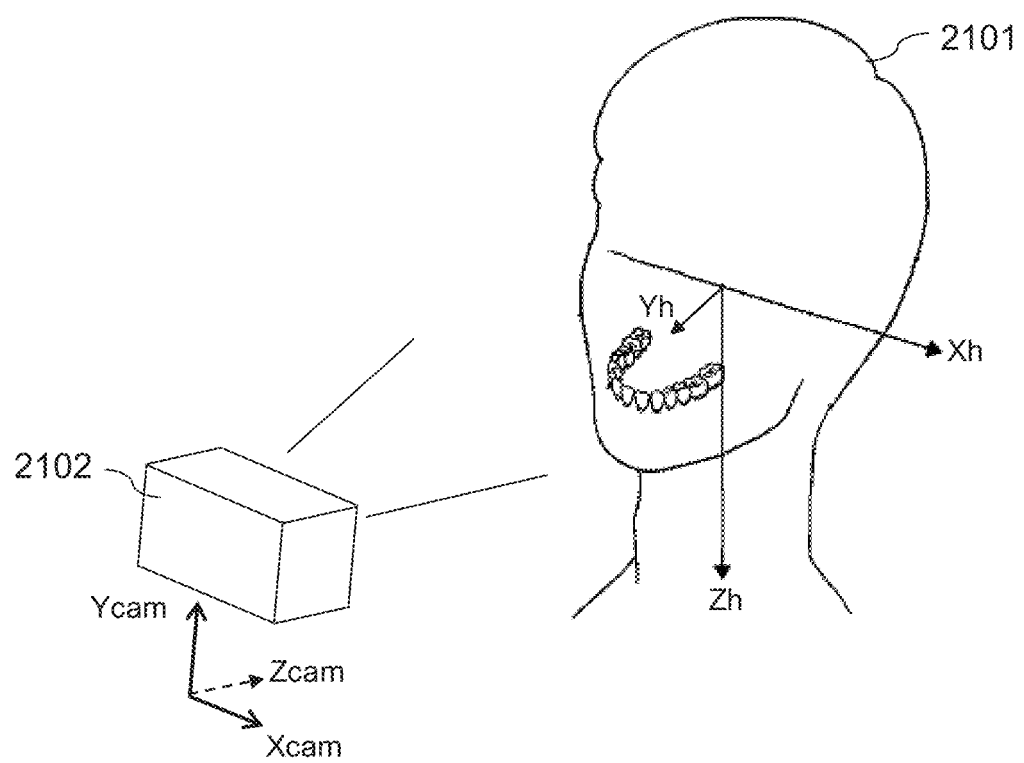
FIG. 21 is a schematic representation of a head of a patient and a digital camera arranged for capturing a 2D picture, e.g. a frontal picture or a lateral picture or a portrait picture.

FIG. 21 is a schematic representation a digital camera 2102 arranged relative to a head 2101 o a patient, and configured for capturing a 2D digital picture, e.g. a frontal picture or a lateral picture or a portrait picture. The head 2101 has a first reference frame with three orthogonal axes Xh, Yh, Zh, and the digital camera 2102 has another reference frame with 3 orthogonal axes Xcam, Ycam, Zcam, which are usually not exactly aligned. When taking a picture with the camera 2102, a projection of the head 2101 on the plane Xcam, Ycam of the digital camera 2102 is captured, and made available in the form of a 2D digital image. This digital image can be transferred to a computer (e.g. via a cable or wireless) and may be displayed on a computer display. Ideally, the vertical axis Ycam of the 2D image should be aligned with the vertical axis Zh of the head, but in practice, there is almost always a small angular difference. This kind of misalignment between the axes Ycam and Zh is well known in the art, and is typically solved by rotating the digital picture, e.g. in the manner as will be described in FIG. 23.

Figure 22A:
FIG. 22A shows a grayscale picture of a smile of a patient, as can be obtained using a camera arrangement as shown in FIG. 21.

FIG. 22A shows a grayscale picture of a smile of a particular patient, as can be obtained using a digital camera 2102, e.g. using an arrangement as shown in FIG. 21. This patient wanted longer teeth, but the dentists were confronted with an additional problem, namely that the upper jaw of this patient was canted by approximately 9° relative to the head.

Figure 22B:
FIG. 22B shows a picture of the same patient, with an envisioned (intended, future) smile to be obtained after dental restoration. It is a challenge, however, to generate a dental design and physical objects that realize a dental restoration which corresponds to this picture.

FIG. 22B shows a photo-realistic picture of the same patient, with an envisioned future smile. This picture was created using the techniques and principles described above (in FIGS. 1A through 18C), but it turned out to be a major challenge to realize such a smile.

In a first attempt, the dentists used the techniques described above.

Figure 23:
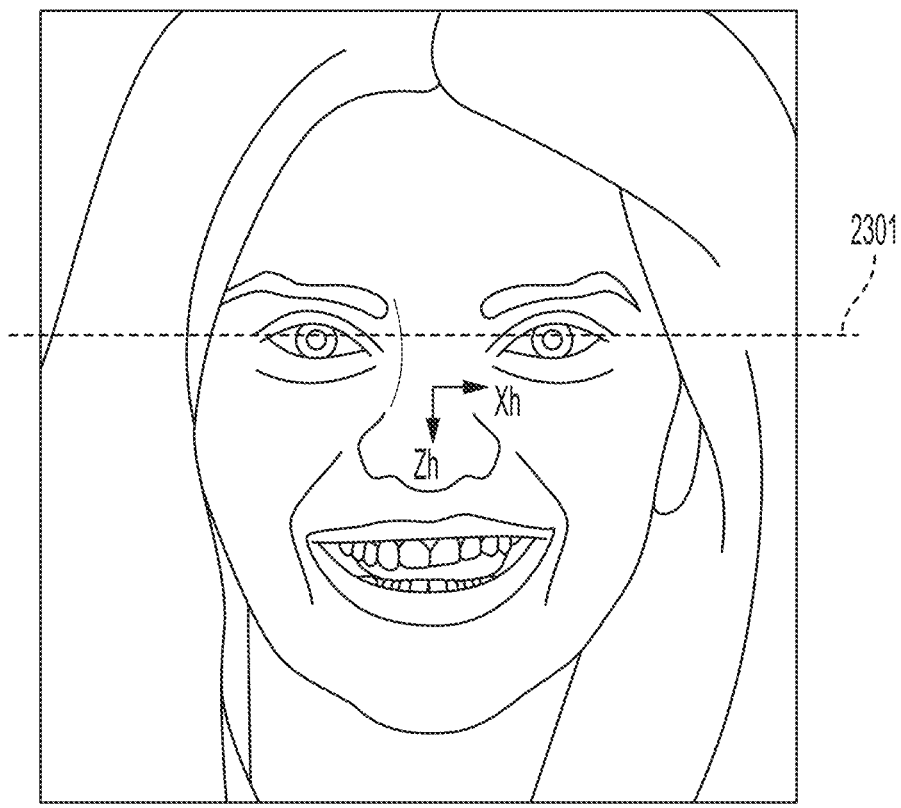
FIG. 23 shows how the picture of FIG. 22A can be rotated such that the head is oriented vertically.

First, the vertical axis Ycam of the 2D digital image was aligned with the vertical axis Zh of the head. This can be done in known manners, for example by adding a line that passes through the eyes of the 2D image, and by rotating the picture such that this line becomes oriented horizontally, as illustrated in FIG. 23. The picture may also be scaled, cropped, etc. in manners known in the art.

Next, a grid comprising an "upper curve" 2401 and a "lower curve" 2402 and a plurality of vertical line segments between the teeth was overlaid over the 2D picture, in analogy with FIG. 4E.

Figure 24A:
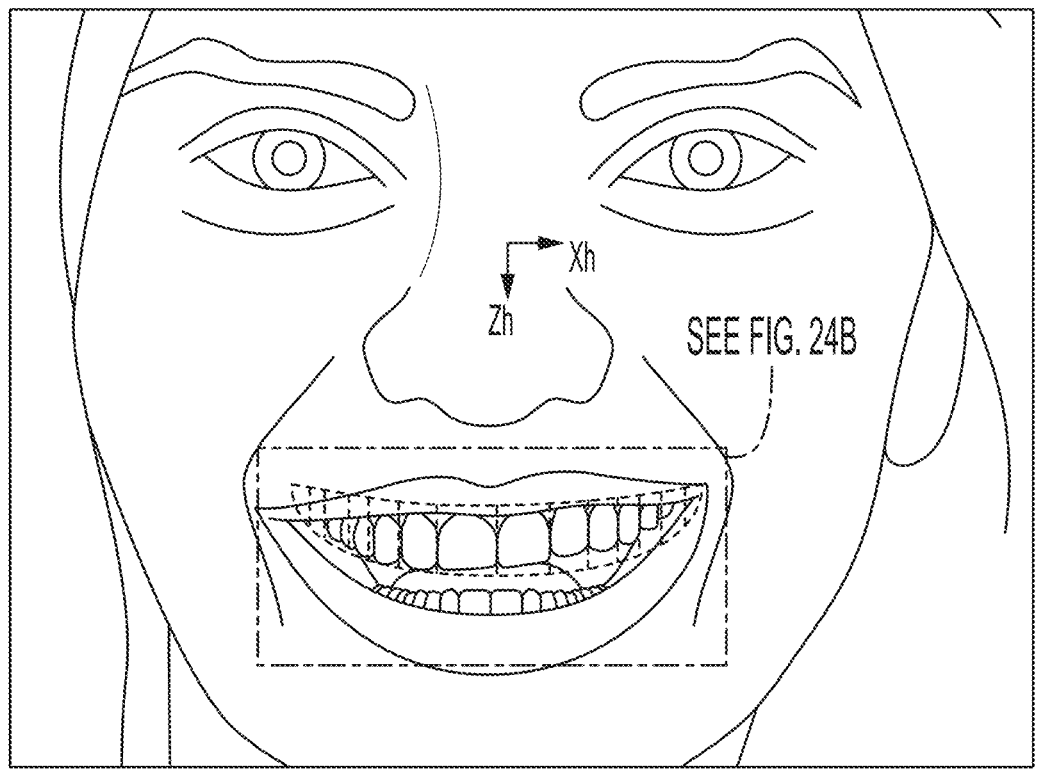
FIG. 24A is an enlarged view of a portion of FIG. 23, with the addition of a grid comprising an "upper curve" and a "lower curve" and a plurality of vertical line segments, similar to the upper van lower curve of FIG. 4E.

FIG. 24A is an enlarged view of a portion of FIG. 23, with the addition of such a grid.

Figure 24B:
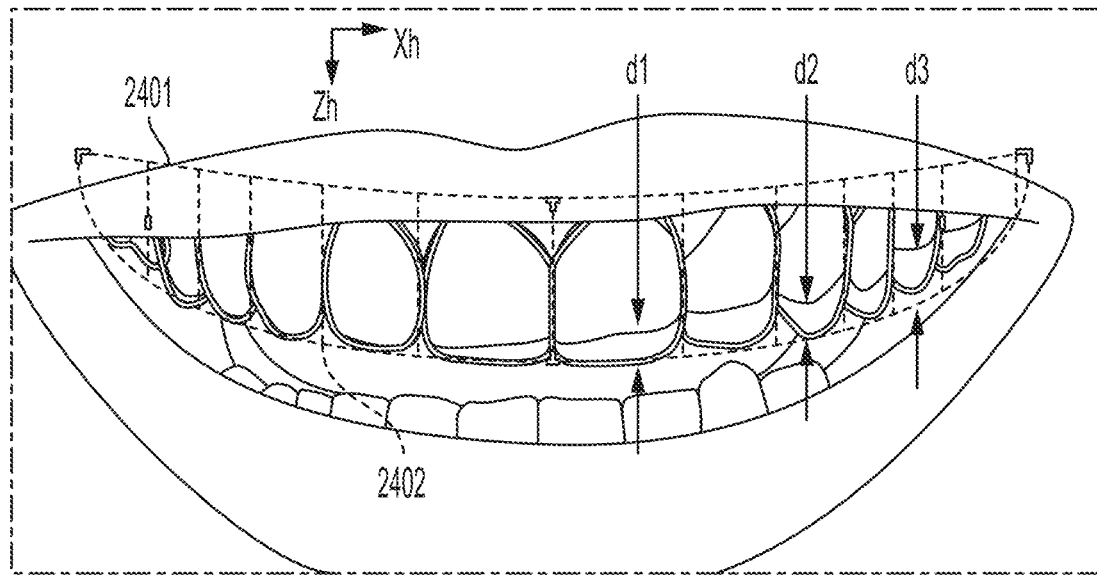
FIG. 24B shows the smile and the grid of FIG. 24A in enlarged view.

FIG. 24B shows the smile and the grid of FIG. 24A in enlarged view. As can be seen, the incisal edges of the teeth on the left side of the picture seem to be located on the lower curve 2402, but the incisal edges of the teeth on the right side of the picture are not. In order to compensate for the canting of the upper jaw, the inventors came to the idea of making the teeth located on the right side of the picture increasingly longer, as indicated by the distances d1, d2, d3 between the existing teeth, and the lower curve 2402. While this works well for veneers and for teeth near the front, it does not work very well for the teeth in the back, in particular the molars, and another solution was required.

The inventors came to the idea of using an intraoral scanner.

Figure 25A:
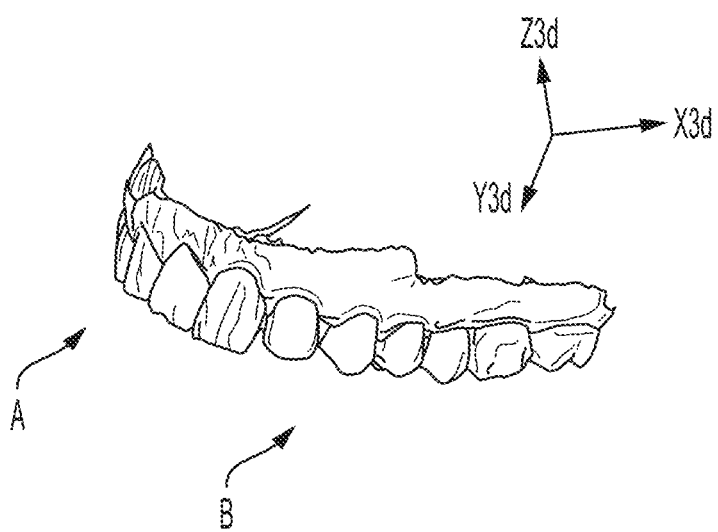
FIG. 25A shows the 3D scan and the reference frame of FIG. 24B from a certain viewing position.

FIG. 25A shows an illustrative example of an intraoral scan of a patient, as can be obtained by an intraoral scanner. Intraoral scanners are commercially available from multiple vendors at the time of writing this application (August 2021), and hence need not be described in detail here. Suffice it to say that an intra-oral scanner can be used by a dentist to generate a 3D digital model, e.g. consisting of a relatively large number of polygons. The 3D digital model may be stored in the form of an STL-file. It was found that the 3D digital model has its own reference frame, schematically represented by three orthogonal axes X3d, Y3d, Z3d, which may have any orientation, unrelated to the head. After capturing an intraoral scan, the 3D digital model can be displayed on a computer screen by viewing software, and can be rotated in any direction, or stated in other words, can be viewed from any viewing angle.

Figure 25B:
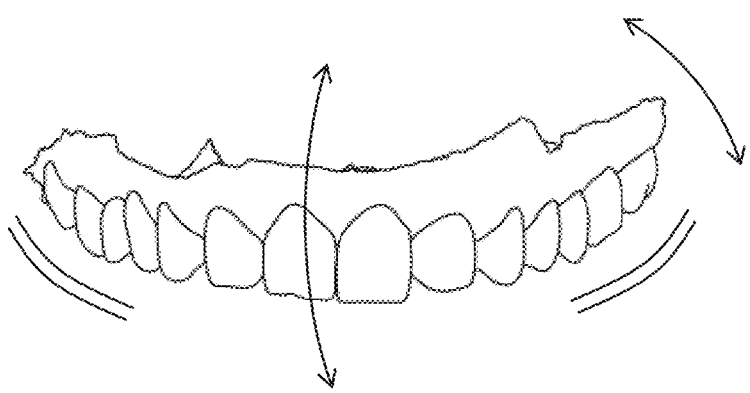
FIG. 25B illustrates how a user can look at the 3D scanned image from an approximate frontal viewing position A, by manually rotating the 3D model.

FIG. 25B shows how the 3D digital model looks from a viewing position A, situated in front of the teeth. This image resembles a "frontal picture", but is actually a projection of the 3D model onto a virtual plane perpendicular to the viewing direction and passing through point A of FIG. 25A. This image can be further adjusted by rotating the 3D model, as suggested by the arrows in FIG. 25B.

Figure 25C:
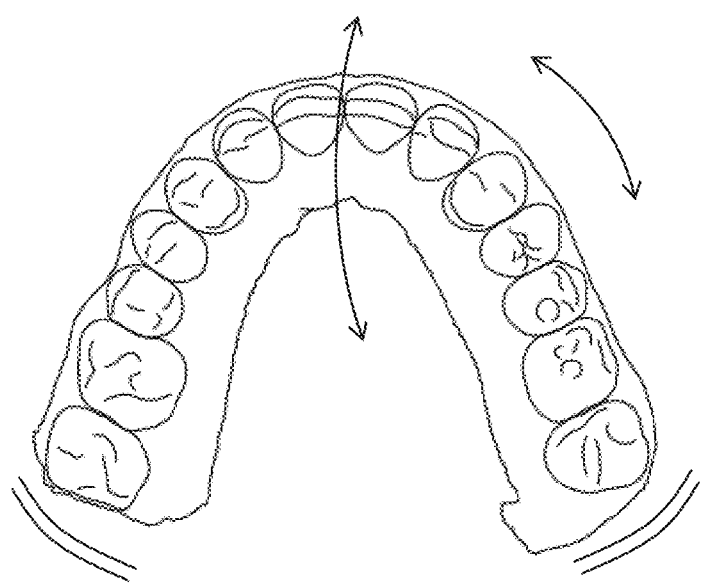
FIG. 25C illustrates how a user can look at the 3D scanned image from an approximate bottom viewing position B, by manually rotating the 3D model.

FIG. 25C shows how the 3D digital model looks from a viewing position B, situated below the teeth. This image resembles a "bottom view", but is actually a projection of the 3D model onto a virtual plane perpendicular to the viewing direction and passing through point B of FIG. 25A. This image can be further adjusted by rotating the 3D model, as suggested by the arrows in FIG. 25C.

The inventors tried to manually orient the projection of FIG. 25B such that it resembled the 2D image of FIG. 24B, but the viewing software does not allow to overlay this picture with a grid, and does not allow to replace a particular tooth by a digital teeth from the library, or to modify characteristics of the tooth, etc. In brief, the inventors contemplated to use similar techniques as described above in FIGS. 1A through 18C, with the intent of making the teeth on the right side of FIG. 25B "somewhat longer". Experiments have shown, however, that such approach is very time-consuming, highly error-prone, and does not provide the desired result. The inventors found that even a slightly different rotation of the views will yield a completely different result (e.g. completely different physical object). In summary, the experiments showed that the mere use of an intraoral scan is interesting, but not sufficient, let alone a practical and efficient tool to create a dental design and/or a dental restoration, using physical objects derived from the design. It was a particular challenge to create a dental design for a patient having an upper jaw that is significantly canted relative to the head.

After many experiments, the inventors found a good solution of creating a dental design, which addresses all or most of the above mentioned problems and challenges. This disclosure proposes a computer implemented method 3000 of creating a dental design having the steps shown in the solid boxes of FIG. 30. The steps in the dotted or dashed boxes (e.g. step 3010, and steps 3012 to 3015) are optional. First, the method will be described, then certain steps will be explained or illustrated in more detail, referring to FIGS. 26A through 29. The method 3000 comprises the following steps:

(a) capturing or obtaining 3001 (e.g. receiving or retrieving) a facial digital image (e.g. a 2D digital picture) of a patient, the facial digital image comprising a head 2101 of the patient and a smile, the smile comprising a plurality of upper teeth.

The facial digital image may be a frontal image, a lateral image or a portrait image. The facial digital image may be captured using a 2D digital camera, and may be transferred to a computer device via a cable (e.g. a USB-cable) or wirelessly (e.g. using Bluetooth or Wi-Fi). Alternatively, the facial image may be a 2D frame selected from a video-clip of the patient. Alternatively, the facial picture may be a 2D view or projection of a facial scan obtained from a facial scanner.

(b) showing 3002 the facialD image or an image derived therefrom (e.g. after rotation) on a display 3104 as a first image 3110;

Preferably the captured image is "rotation-corrected", such that the eyes of the patient are located on a horizontal line, and the vertical axis Zh of the head is oriented vertically on the display.

(c) capturing or obtaining 3003 (e.g. receiving or retrieving) a 3D intraoral scan comprising said plurality of upper teeth;

The "3D intraoral scan" typically comprises a single object composed of a plurality of polygons, but does not have the notion of individual teeth.

(d) aligning 3004 the 3D intraoral scan to the head of the patient using the facial image;

This is an important step, and is illustrated in FIGS. 26A and 26B. The alignment may be performed by indicating the position of a plurality of specific points, both in the 2D image (thereby indicating its lateral and height position on the screen), and also in a view or projection or representation of the 3D digital model, e.g. on the "bottom view", thereby indicating its lateral and depth (or inward) position. By doing this for multiple points, a relationship between the reference frame of the 2D image and the reference frame of the 3D model can be established. Once this relationship is established, it is possible to define objects in the 3D model (e.g. bounding boxes 2703), and to show a projection of these bounding boxes not only on the projected image of the 3D model (e.g. as a bottom view), but also on the 2D image with the smile of the patient, using a transformation.

It is noted that, instead of bottom view, a portrait view on the 3D model, e.g. from the left side of the patient, or the right side of the patient, may also be very handy. In such a view the lateral position is masked, but the height position and the position in the Yh direction (see FIG. 21) are very clearly visible.

Figure 27A:
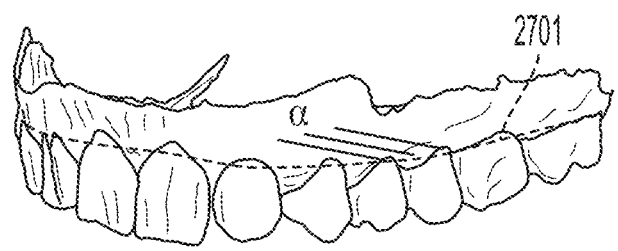
FIG. 27A shows the location of a U-shape curve tangential to an outer surface of the teeth, and situated near the zeniths of the existing teeth of the patient, in the 3D space of the 3D model. This U-shape curve is also referred to herein as the "original upper curve".
Figure 27B:
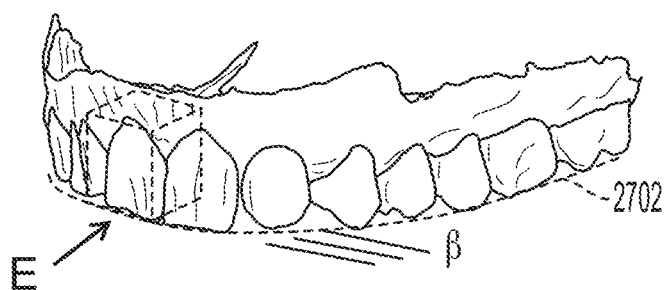
FIG. 27B shows the location of a U-shape curve tangential to an outer surface of the teeth, and situated near the incisal edges of the existing teeth of the patient, in the 3D space of the 3D model. This U-shape curve is also referred to herein as the "original lower curve".
Figure 27C:
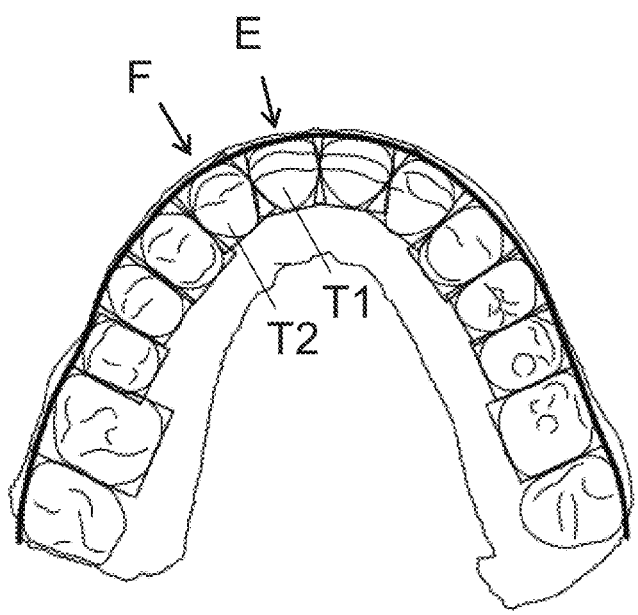
FIG. 27C shows the location of the "original upper U-shape curve" and the "original lower U-shape curve" in the 3D space of the 3D model, viewed from underneath, where they substantially coincide. A plurality of "bounding boxes" are added, each bounding box surrounding a single tooth.
Figure 27D:
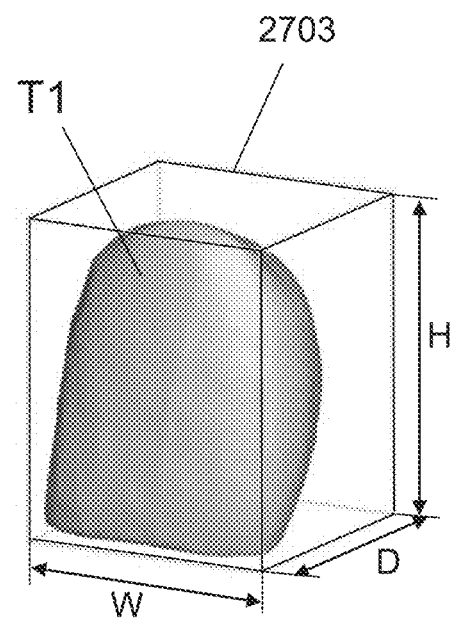
FIGS. 27D and 27E collectively show an example of a bounding box (seen in perspective view, and seen from above) comprising a "frontal incisor", in a preferred way of encapsulation.

(e) determining 3005 a plurality of bounding boxes 2703 in the 3D digital scan, each bounding box comprising a single digital tooth;

The bounding boxes may have a beam shape or a cuboid shape or a prism shape or a rectangular parallelepiped shape, e.g. as illustrated in FIG. 27D. In this way, the "3D scan" is converted into a "3D digital model", e.g. by "image segmentation". The purpose of this segmentation is to detect individual teeth, and to separate them. The separation may use virtual planes oriented perpendicular to the U-shaped curve. Such virtual planes may start from a notch or indentation of the 3D scanned surface.

The 3D digital model may comprise multiple objects, e.g. one object for each tooth of the upper jaw. It may also comprise one or more U-shaped curves, as will be explained further.

(f) showing 3006 a view (or a projection or an outline) of said 3D digital model and the 3D bounding boxes as a second image 3120 on said display;

The first image is ideal for changing the length of the bounding boxes and thus the length of the future teeth, and to get an impression on how this would look on the particular patient. The second image 3120 preferably shows the 3D model from a different viewing angle. Preferably the software allows the user (e.g. the dentist) to freely rotate the second image to view the 3D model in any desired orientation. A very practical orientation for viewing or adjusting the width W and the depth D (see e.g. FIG. 27E) of the teeth is a "bottom view".

(g) showing 3007 a representation (e.g. a projection, or an outline or the ribs) of the bounding boxes as a graphical overlay on the first image 3110 on said display;

This will typically look like a plurality of rectangles, but in contrast to the rectangles of FIG. 18A, where the vertical lines were intentionally positioned between the teeth, the ribs of the 3D bounding boxes will typically not be situated exactly between the teeth.

It is important to realize that the "real data of the digital design" (the master data) of this embodiment is at least partially codified in the 3D model, inter alia by the size (W,D,H), the position and orientation (rotation about vertical axis) of the bounding boxes of the 3D model, which may be changed by the user.

The user may wonder why the 2D image is still relevant or not. The 2D image is important initially for aligning the 3D model to the head of the patient. As will be explained further, the alignment preferably involves the location of at least one U-shaped curve, and 3D bounding boxes tangential to the U-shaped curve, but after the alignment, the 3D model is "master". Showing the 2D image is still extremely useful, however, e.g. to change the height of the bounding boxes (although the height of the bounding boxes can also be changed in the second image, when choosing an appropriate view), and/or to give an impression (e.g. by means of contours) of how the future teeth will look like on the real face of the patient, but for example, it is better to change the width W of the teeth in the second image, rather than by moving the vertical lines of the grid overlaid on the first image. This is further explained in FIG. 31.

(h) performing at least once:
        (i) allowing 3008 a user to modify at least one dimension (e.g. Depth, Width or Height) of at least one bounding box in the first image 3110 or second image 3120, and detecting said modification;

As mentioned above, after "the alignment", the grid shown in the 2D image is actually a projection of the 3D model, comprising e.g. at least one U-shaped curve and a plurality of 3D bounding boxes. The 2D grid itself no longer exists as a separate thing which can be modified separately. For example, after the alignment, increasing the height of a rectangle in the first image actually means: increasing the height of a 3D bounding box of the 3D digital model. It is an advantage that the user can change the position of the U-shaped curves, and the height of the bounding boxes not only in the second image, but also in the first image, because it gives the user a better impression of how the modification (s) will look like in reality, on that particular patient.

(ii) for each modified bounding box, defining 3009a a limited set of parameters to characterize the tooth inside the bounding box, and searching and retrieving 3009b a limited number of candidate matching teeth from a digital library comprising a plurality of 3D digital teeth based on said limited set of parameters, and proposing 3009c a candidate matching tooth from said limited number of candidate matching teeth;

With "modified bounding box" is meant any of: a modified spatial position, a modified rotation about its upright axis, a modified width W, a modified height H, a modified depth D. The tooth inside the bounding box can be characterised by a limited set of parameters, e.g. by at least 4 and at most 50 parameters, or at least 4 parameters and at most 10 parameters. The at least 4 parameters may include: a unique position number of the tooth (e.g. an FDI number), and three dimensions: W, H, D. Optional further characteristics may include: a left and a right papilla height value; a left and a right embrasure value. It is an advantage that the intraoral scan allows to accurate measure the papilla height, also for teeth in the back (molars). Other parameters may be added, e.g. one or more numbers to describe a curvature or flatness of the tooth; one or more numbers to describe the position of lateral contacts with neighbouring teeth, etc. The limited set of parameters can be used as an index for searching. The limited set of parameters can also be used to determine a "matching score" between a particular "future tooth" (or rather "future bounding box" in which the future tooth has to fit) and a candidate tooth from the 3D digital library.

It is explicitly pointed out that this embodiment of this disclosure (illustrated in FIGS. 21 to 31) does not require a 2D digital library of teeth, but only requires a 3D digital library of teeth. New teeth can be added to this 3D digital library, each time a 3D intra-oral scan is taken of a new patient, and processed in order to detect individual teeth (e.g. by segmentation), and by characterizing the teeth, e.g. using 3D bounding boxes as illustrated in FIGS. 27A through 27F.

The search algorithm will typically find a number of candidate matching teeth, and will typically propose the one with the highest matching score.

In certain embodiments, a bitmap of a top view of the tooth may be quantized with 1 bit-values, e.g. in an N×M raster, where N and M are values in the range from 4 to 32, each bit-value indicating whether the raster is part of the tooth or not. For example if N=10, the cross-sectional shape of the tooth can be codified in 10×10=100 bits or about 13 bytes. This bitmap information may be added to the limited set of parameters. But of course, values smaller or larger than 10 can also be used, e.g. an 8×8 raster requires only 8 additional bytes, while a 16×16 raster requires 32 additional bytes, which is still very well manageable, yet allows to find a tooth with approximately the same cross-sectional "shape". Using an N×M bitmap offers the advantage that it is extremely easy to detect similarity between two shapes by simple bitwise operations (e.g. using one or more of the "xor", "and", "not", "or" operands).

Additionally or alternatively, the contour of a bottom view of the tooth may be encoded in an efficient manner, and added to the limited set of parameters.

Figure 28A:
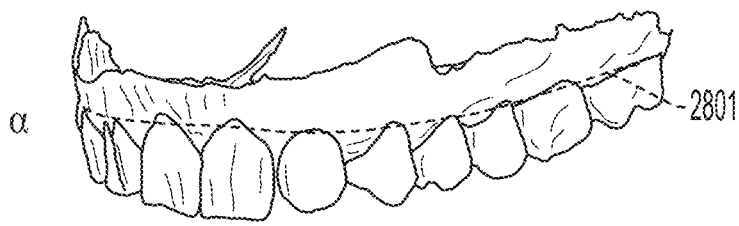
FIGS. 28A, 28B, 28C, 28D, and 28E collectively illustrate how the "original upper curve" or the "original lower curve" and the "future lower curve" can help to define the positions, orientations and dimensions of the bounding boxes of the future teeth, and that a matching tooth can be searched in the 3D digital library based on the (modified) dimensions of the bounding boxes.

(iii) overlaying 3011 the first image with a digital representation (e.g. a projection of a contour) of the proposed candidate matching tooth or teeth from the digital library, for example as illustrated in FIG. 26C or 28A.

Many implementations and variants of this method are possible.

The method 3000 may further comprise a step of: allowing 3010 a user to select another candidate matching tooth from the limited number of candidate matching teeth.

The method 3000 may further comprise a step of: saving 3013 the digital design as a digital file on a non-volatile memory (e.g. a USB stick or a flash card) or on a storage device (e.g. on a hard disk drive, a CD-ROM, a DVD-disk, a Blue-Ray disk, a network drive). The digital file may comprise one or more of: the first set of limited parameters, a position e.g. in the form of screen coordinates of the plurality of visual objects, a reference to said at least two teeth in the digital library.

The method 3000 may further comprise a step of: providing 3014 a 3D-file of at least one candidate matching tooth from the digital library, optionally after scaling, rotation or digital grinding.

The 3D file may be suitable for printing by a 3D printer. The 3D file may be extracted from, or derived from a library of 3D digital teeth corresponding to the 2D images of teeth. It is an advantage of this embodiment that it generates a 3D-file which can be used to create a physical realisation of the one or more dental restoration. This 3D file may for example be used to build a wax-model.

The method 3000 may further comprise a step of: producing 3015 at least one physical object based on said 3D file, e.g. in the form of a crown, a bridge, an abutment, an implant, a veneer.

In a practical implementation, of course other functionality may be offered as well, such as allowing a user to add or remove or modify certain characteristics, and adjusting or rearranging the limited list of candidate matching accordingly.

Figure 28B:
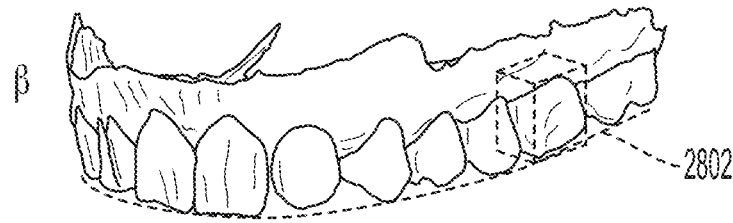
Figure 28C:
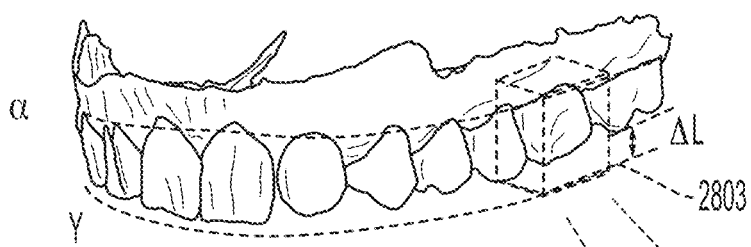

The method 3000 can also be extended with the functionality of allowing a user to modify the position of the "lower curve", e.g. from the position in FIG. 28B to the position in FIG. 28C, and automatically adjusting the heights of at least two of the 3D bounding boxes to the position of the lower curve, and automatically searching in the 3D digital database for new candidate matching teeth, e.g. when dragging the position of the lower U-shaped curve. This is somewhat similar to the functionality described in FIGS. 19A through 20, but now implemented using the first and second image, and using the 3D digital database.

In an embodiment, the limited set of parameters to characterize a tooth (or a bounding box containing that tooth) contains only parameters related to that particular tooth, not about its environment (e.g. left neighbouring tooth, right neighbouring tooth, antagonist on the opposite jaw).

In another embodiment the limited set of parameters to characterize a tooth (or a bounding box containing that tooth) not only contains parameters related to that particular tooth itself, but also parameters related to its environment (e.g. left neighbouring tooth, right neighbouring tooth, embrasure, papilla height) on the same jaw, but not on the opposite jaw.

In yet another embodiment the limited set of parameters to characterize a tooth (or a bounding box containing that tooth) not only contains parameters related to that particular tooth itself, but also parameters related to its environment on the same jaw, and also information about one or more teeth on the opposite jaw, e.g. level of contact or spatial intersection with one or more antagonist teeth of the opposite jaw.

The method may further comprise: displaying a U-shaped lower curve defining the length of existing teeth, and/or for defining the length of future teeth.

The methods may also further comprise the step of: allowing a user to adjust a position of the lower curve. A similar mechanism as described above in FIGS. 19A and 20, and adjustment of the position of the lower curve may trigger the adjustment of multiple bounding boxes, and an automatic search may be performed for these bounding boxes.

The method may also further comprise the step of: determining an amount of contact or an amount of interference of a particular candidate matching tooth with the existing antagonist of the opposite jaw, and selecting a candidate matching tooth with the optimal contact or the least interference.

As indicated above, some of the steps will now be described and illustrated in some more detail.

FIGS. 26A, 26B, and 26C show one way of how the reference frame of the 3D model can be aligned to the reference frame of the head, albeit indirectly, by indicating screen positions of a plurality of particular points, both on the first image 2610 (i.e. on the rotation-corrected 2D picture of FIG. 23) and on the second image 2620 (i.e. on a projection of the 3D model). In the example of FIG. 26B, the projection of the second image shows a lateral view on the left upper teeth, but another view would also work.

In the examples of FIGS. 26A and 26B, the alignment is done by indicating the on-screen positions of a plurality of specific points both in the first image 2610 and the second image 2620. In the example, a first specific point 2601 (indicated by a black circle) is chosen at the zenith of the left frontal incisor, a second specific point 2602 (indicated by black triangle) is chosen at the incisal edge of the left frontal incisor, and a third specific point 2603 (indicated by a plus character) is chosen at the incisal edge of the left canine. But of course more than three points can be used for the alignment. The selection and indication of the specific points may be automatic or semi-automatic or manual. Based on the screen coordinates of these points, a relationship can be established between the reference frame of the 2D picture and the reference frame of the 3D model. Once this relationship is established, it is possible to define a transformation which translates the position of any position in the first image (read: in the rotation-corrected 2D picture) into a position in the second image (read: in a projection of the 3D digital model), or vice versa.

After alignment, FIG. 26C shows an interesting arrangement of the first image 2610 showing the smile of the patient comprising a plurality of upper teeth, and the second image 2620 showing a bottom view of the existing upper teeth, for modifying the dental design. As can be seen, the locations of the points 2601, 2602 and 2604 in the first image 2610 are clearly different. The first image is therefore very well suited for showing and/or adjusting the length of the teeth. And as can also be seen, the locations of the points 2601, 2602 and 2604 in the second image 2620 substantially coincide, but the widths W of the teeth and the depths D of the teeth is very well visible in the second picture. Hence, by simultaneously displaying the first image 2610 and the second image 2620 (not necessarily a bottom view) on a single display (e.g. as in FIG. 31) offers the advantage of being able to easily and accurately adjust any of the Height, Width and Depth of particular teeth.

FIGS. 27A, 27B, 27C, 27D, 27E, and 27F illustrate how the 3D scan can be converted to a 3D-model comprising (inter alia) a plurality of individual teeth, and how these individual teeth can be characterised in a compact an efficient manner using a limited number of parameters, which parameters can also be used as an index, or as part of an index to allow fast and efficient searching in a database of digital teeth, and which parameters may also be used to calculate a matching score between an envisioned tooth and a tooth from the database. Desiring to design a smile as shown in FIG. 22B, but confronted with the problem of the canted upper jaw shown in FIG. 22A, the inventors came to the idea of using at least one U-shaped curve or "U-shaped arch" in 3D space.

FIG. 27A shows the location of a U-shaped curve 2701, tangential to the outer surface of the teeth, and situated near the zeniths of the existing teeth of the patient, in the 3D space of the 3D model. This curve is also referred to herein as the "original upper curve". Rather than interconnecting the existing zenith points by a chain of piecewise-linear line segments, it is preferable to use a relatively smooth U-shape. In certain embodiments, this U-shape is described mathematically by means of a polynomial expression, or using a spline, or in any other suitable way. In certain embodiments, the U-shape may be planar, i.e. situated in a plane α. This can greatly simplify the implementation.

FIG. 27B shows the location of another U-shaped curve 2702, also tangential to an outer surface of the teeth, but situated near the incisal edges of the existing teeth of the patient, in the 3D space of the 3D model, also referred to herein as the "original lower curve". This U-shape may also be planar in a plane (3, and described by means of a polynomial or spline.

FIG. 27C shows the location of the "original upper U-shaped curve" 2701 and of the "original lower U-shaped curve" 2702 in the 3D space of the 3D model, viewed from underneath. As can be seen, a projection of the upper U-shaped curve 2701 and the lower U-shaped 2702 substantially coincide. The inventors also came to the idea of using "image segmentation" to separate the (single) 3D-object into a plurality of objects, each comprising a single tooth. The segmentation may be performed automatically (e.g. using computer vision), or semi-automatically, or manually. The inventors also came to the idea of using "bounding boxes" 2703, each bounding box surrounding a single tooth. The bounding boxes are preferably beam shaped or cuboid. The height of a particular bounding box is defined by the distance between the upper curve 2701 and the lower curve 2702 at a particular location. If the two planes α, β are parallel, which is usually the case, all bounding boxes of a particular patient have the same height H.

FIG. 27D illustrates that, in preferred embodiments, the bounding boxes are chosen such that one of the side surfaces of the bounding box is tangential or at least parallel to the U-shaped curve. This is not an arbitrary choice, but takes into account for example that, in order to fill the opening of a missing tooth having a given width W, it is best to select a tooth from the database having that particular width W, even if the depth may be slightly different than that of the original tooth. This is an important difference with existing tools, where the level of matching is related to "volume".

By orienting one of the rectangular surfaces of the bounding box substantially tangential to the U-shaped curve, two other rectangular surfaces are oriented substantially orthogonal to the U-shaped curve. The location of these side planes may also be used or re-used in the segmentation process. By orienting the bounding boxes in this way, the dimensions of the bounding box are not only relevant for the dimensions of the tooth itself, but also for the tooth in its environment, in particular the "width" W is an indication for the available space between neighbouring teeth. A tooth from the library having a larger value of W will typically not fit in the available space. In contrast, a variation of the parameters D and H typically causes less problems. Orienting the boundary boxes in this way also offers the advantage that, when replacing a particular tooth by a tooth from the digital library, the latter usually does not need to be rotated, but its orientation is typically very well suited. Thus using a consistent orientation of the bounding boxes relative to the entire arch may help in searching suitable teeth. The parameters of the bounding boxes correspond with dimensions of real physical objects. The parameters can be used to index the digital library in an efficient manner.

Figure 27E:
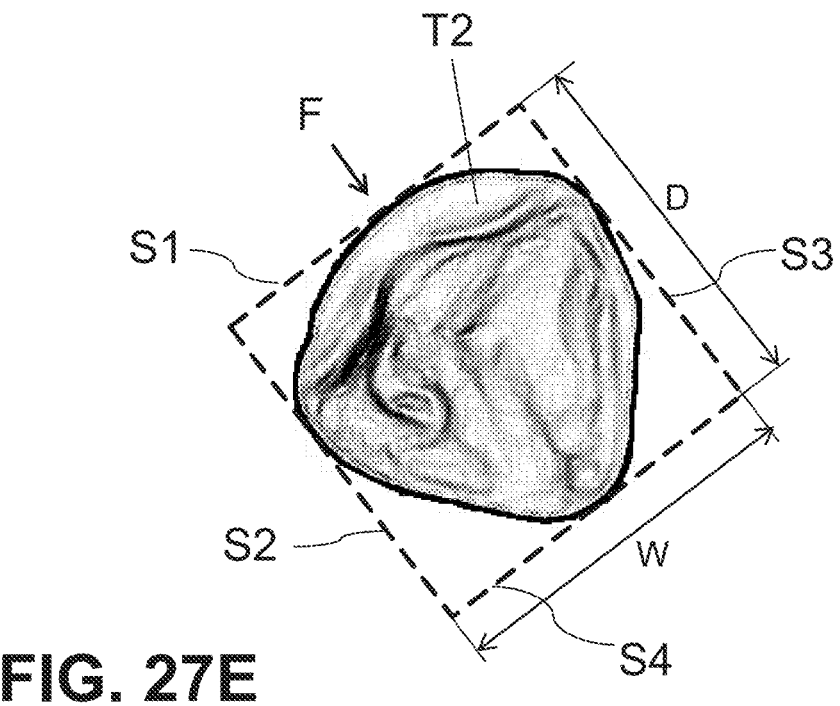
Figure 27F:
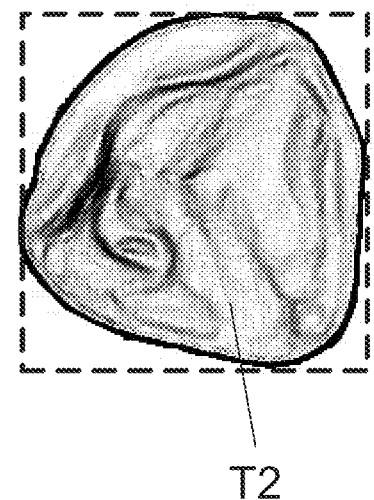
FIG. 27F shows an example of a "minimum bounding box" surrounding the same dental incisor.

FIGS. 27E and 27F illustrate that the preferred way of encapsulating individual teeth, by using beam-shaped or cuboid boxes having four rectangular side surfaces S1-S4, one of which (S1) is substantially parallel or tangential to the upper and/or lower U-shaped curve, and two others of which (S2 and S3) are oriented substantially perpendicular to the U-shaped curve, is different from a so called "minimum bounding box" for most shapes. FIG. 27E shows the tooth T2 of FIG. 27C using a bounding box as described above, with one side S1 tangential or substantially parallel to the U-shaped curve, where the "width" and "depth" and "orientation" information is encoded in the dimensions of the boundary box itself, thus having an undeniable correspondence to the real world. FIG. 27F shows the same tooth T2 in a "minimum bounding box" as a mere encapsulation.

It is noted that the shape of the U-shaped upper curve 2701 and lower curve 2702 may slightly vary depending on the smoothness of the curves, which means that the bounding boxes surrounding the teeth may be slightly rotated about an axis oriented in the height direction of the teeth. But it will be appreciated from FIG. 27E that this only has a minimal impact on the width W and depth D of the bounding box and the tooth, and has no impact on the height, in other words, it will have only a minimal impact on the results of a search.

It is noted in this respect that the orientation of the bounding boxes is not uniquely defined, because one could rotate the bounding box for example with its left side perpendicular to the U-shaped curve, or with its right side perpendicular to the U-shaped curve, or with a central plane halfway between its left side and its right side perpendicular to the U-shape curve. This will result in the bounding box being slightly rotated about the tooth, or the tooth being slightly rotated inside the bounding box, but the search algorithm is robust for these variations, because the width W and the depth D do not substantially change.

Of course, the ribs of the bounding boxes surrounding, encapsulating or delimiting the teeth do not actually need to be stored in the database, because they are implicit. Apart from the index, described above, the actual database of 3D digital teeth needs to the surface of the tooth. This can be done in known manners, for example by storing a subset of the original polygons, optionally with additional polygons describing the side surface of the tooth.

Having built a 3D digital library of teeth obtained from multiple patients, the database can then be used for generating a dental design, for example for the patient of FIG. 22A, having a canted upper jaw.

FIGS. 28A and 28B illustrate how one or both of the upper U-shaped curve 2801 and the "future" U-shaped curve 2803 can be determined in the 3D virtual space, in the manner described above. As explained above, after the U-shaped curves are determined, the 3D scan can be segmented into individual teeth, each surrounded or encapsulated by a virtual bounding box, one of which is shown in FIG. 28B. The initial height of this bounding box may be set equal to the distance between the U-shaped curves, which, in case the U-shaped curves are located in two planes α, β is equal to the distance between these planes at the respective position.

FIG. 28C shows how the lower U-shaped curve 2803 of the envisioned teeth for this particular patient should look like in 3D virtual space, where the lengths of the teeth on the right side of the picture are longer than the lengths of the teeth on the left side of the picture in order to compensate for the canted upper jaw. This may be better understood from FIG. 28D showing a plane α comprising the original upper U-shape 2801, with a plane β comprising the original lower U-shape 2802, and a plane γ comprising the future U-shape 2803.

The software may be configured to display the future U-shaped curve 2803 in the first and second image 3110, 3120 (see FIG. 31), in which case the user (e.g. the dentist) should manually modify the heights of the bounding boxes, or the software may be configured to automatically and dynamically adjust the heights of the bounding boxes as the U-shaped curve is being dragged (e.g. in a manner similar explained in FIGS. 18A to 20).

Figure 28D:
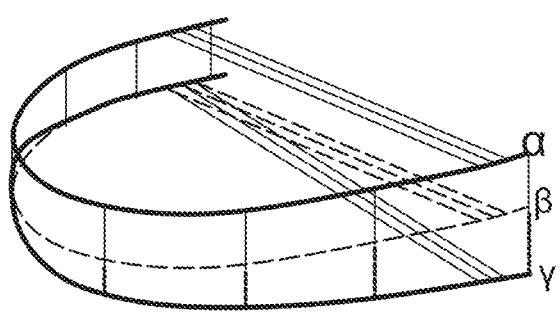
Figure 28E:
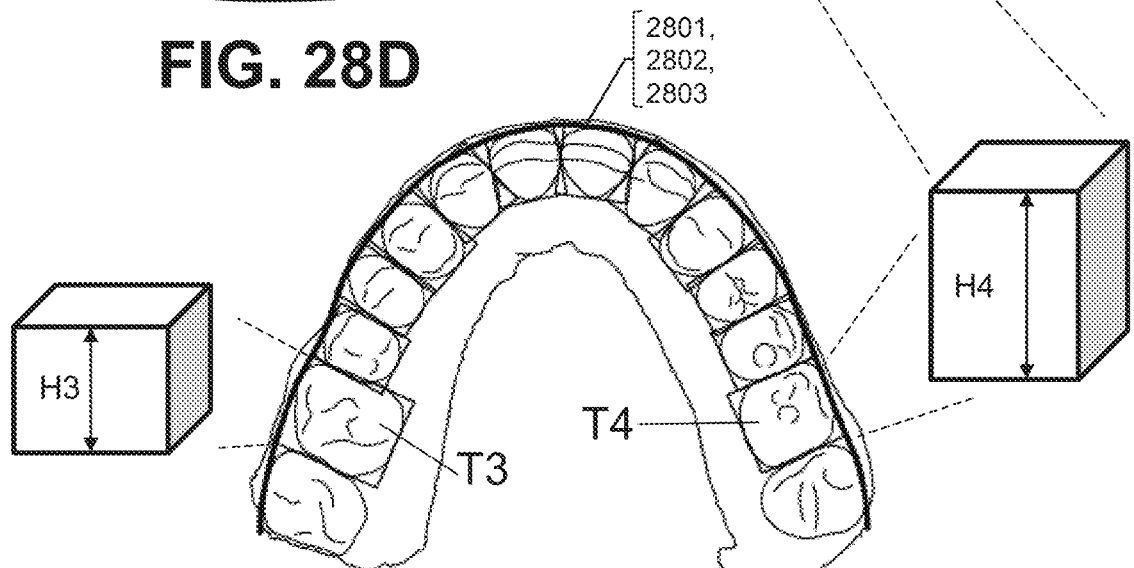

FIG. 28E illustrates that, even though the three U-shaped curves seem to coincide in the bottom-view, they are three different curves in the 3D digital model, as shown in FIG. 28D, and the heights of the various bounding boxes are different, depending on the position of the teeth, for example a relatively small value H3 for tooth T3, and a relatively large value H4 for tooth T4.

By using the techniques described above, in particular by making use of the (preferably planar) U-shaped curve 2803, situated in 3D-virtual space, defining a plurality of bounding boxes, which are projected on the aligned, and rotation-corrected 2D image, a design very much similar to that of FIG. 22B, but using digital teeth obtained from the 3D digital library, can be obtained.

Three U-shapes are shown in FIGS. 28A through 28E for explanation purposes only, to make a clear distinction between the "bottom" of the bounding boxes, the height of the bounding boxes of the original teeth, and the envisioned height of the bounding boxes of the future teeth. But in a practical implementation, it may suffice to use and/or show only a single U-shaped curve.

Figure 29:
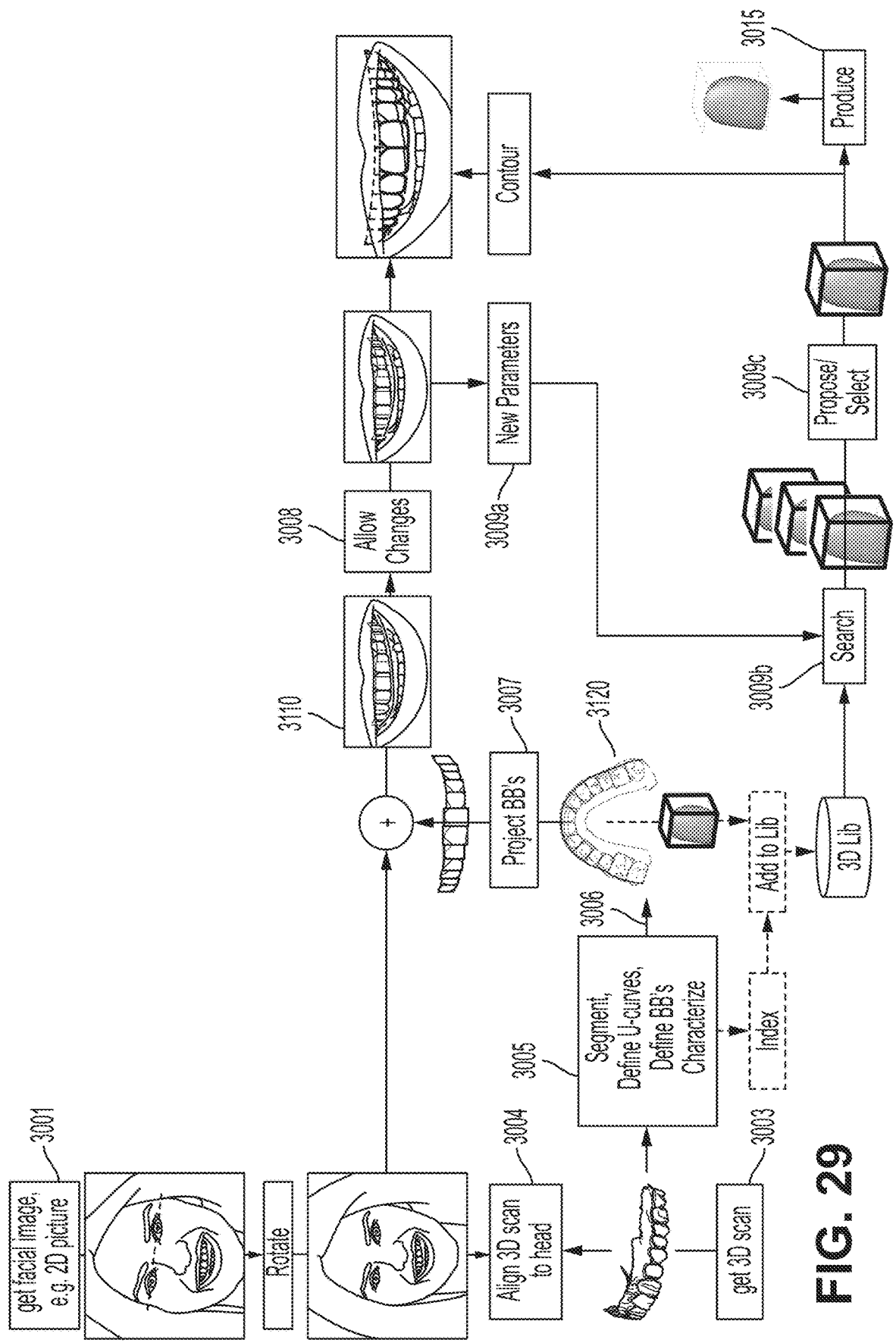
FIG. 29 shows an example of a possible data-flow, e.g. using the method of FIG. 30.

FIG. 29 illustrates the various steps of the process in a single picture. It is noted however that a user does not have to apply all the steps. For example, it is noted that not all the teeth of all the patients have to be indexed and have to be added to the digital library, although they may. But FIG. 29 illustrates how the 3D digital library can be built and can be indexed. In fact, once the library has a sufficiently large number of various teeth, many users will probably may never add teeth to the library, but only use teeth from an existing library.

Figure 30:
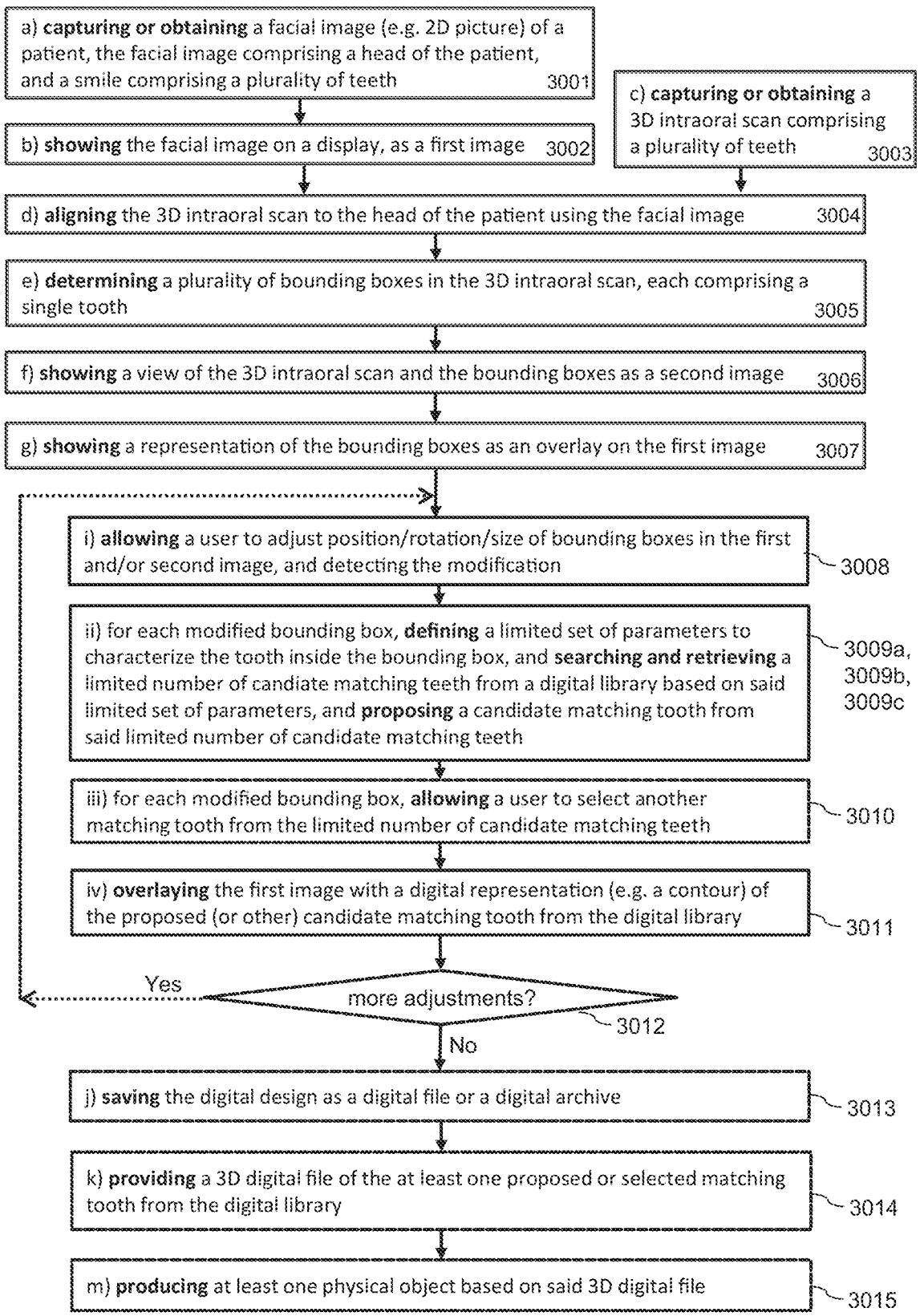
FIG. 30 shows a flowchart of a method of generating a dental design using a 3D digital library of individual teeth.

FIG. 30 shows a flowchart of the method of generating a digital design, as was already discussed above. Potential additional steps will be explained in FIG. 32A to FIG. 34C.

Figure 31:
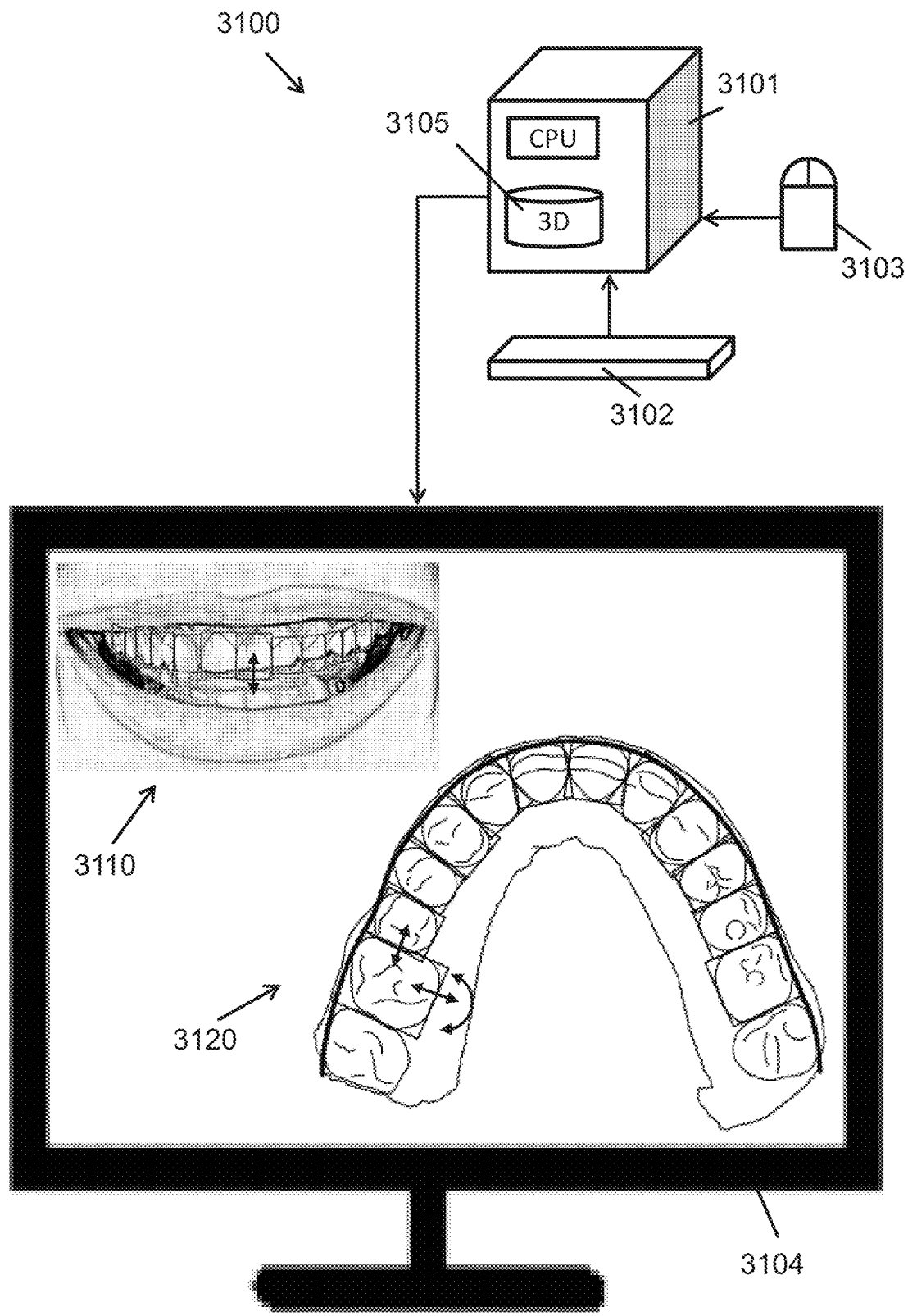
FIG. 31 shows an example of a computer system, proposed by this disclosure.

FIG. 31 is added for completeness, showing a computer system 3100 comprising a computer device 3101, and a keyboard 3102 connected to an input of the computer device, and a pointing device 3103, e.g. a mouse device connected to an input of the computer device, and a display 3104 connected to an output of the computer device. The computer device 3101 further comprises at least one processor, and memory, and a storage device or a non-volatile memory (not shown) containing an executable program for performing some or all of the steps of the method described in FIG. 30. The computer device may also contain the 3D digital database 3105, stored on a storage device. Alternatively, the 3D digital database may be stored on a network drive (not shown), communicatively connected to the computer device 3101, for example using an internet connection.

The display 3104 of FIG. 31 shows simultaneously a first image 3110 composed of the actual smile of the patient (e.g. a portion of the rotation-corrected image of FIG. 23), overlaid by a projection of the ribs of bounding boxes, and a second image 3120, showing a digital representation of the 3D digital model, including the bounding boxes. An arrow is added in the first image to illustrate that the height of the projected bounding boxes may be adjusted in the first image 3110. And two arrows are added in the second image to illustrate that the width and depth of the bounding boxes may be adjusted in the second image. A circular arrow may be added in the second image to illustrate that the bounding box may be rotated about its vertical axis (perpendicular to the bottom view).

The second image shown in FIG. 31 is a bottom view on the upper teeth, but as explained above, any other view on the 3D model may also be shown. When the ribs are moved in the first image, the 3D digital model is adjusted, and the position of the ribs in the second image is also automatically adjusted, and vice versa. The same applies for the lower U-shaped curve 2802. When the position or orientation of the U-shaped curve is changed in the second image (which is a view on the 3D model from any desired viewing angle), the position of the U-shaped curve in the 3D model is adjusted, and the position of the U-shaped curve in the first image is also updated.

The heights of the bounding boxes may be automatically determined as an initial height when determining or detecting the position of the lower U-shape curve. Depending on the implementation, the heights of the bounding boxes can be automatically updated when the position of the lower U-shaped curve is adjusted, or the sizes of the bounding boxes may need to be updated manually.

FIG. 31 also illustrates how the simultaneous display of both a 2D image of the patient, e.g. a frontal image, and a second image being a view on the 3D scan, which is aligned to the first image, such that objects in the 3D space are correctly displayed in the first image, allows users to actually design/modify/change/replace/rotated/move/ . . . the teeth in the 3D space, while being able to "see" how those changes will actually look like on the face of the patient. This is particularly important for patients of which the upper jaw is canted. It can now be better appreciated why a "trial-and-error" kind of design which is performed only in 3D space, without "a coupling" to a 2D facial picture, is more time-consuming, more error-prone, and will likely result in a design which is inconsistent and/or completely different from the intended design shown in FIG. 22B for example.

While not illustrated in the Figures, the method may further comprise:
taking a second intraoral scan, wherein the upper teeth are in contact with the lower teeth;
determining a position in 3D space of a U-shaped curve tangential to the incisal edges of the lower teeth;
determining a relative position between the U-shaped curve tangential to the incisal edges of the upper teeth and the U-shaped curve tangential to the incisal edges of the lower teeth;
in order to determine a relative position between teeth from the lower jaw and the upper jaw.

And the method may further comprise a step of determining one or more antagonist teeth for a particular tooth of the upper jaw.

And the method may further comprise a step of determining an amount of interference or penetration or spatial overlap between a particular tooth of the upper jaw and a tooth obtained from the library, when positioned at the location of to one or more antagonist tooth.

And the step of proposing a particular candidate matching tooth from the 3D digital library may take into account said amount of interference or penetration or spatial overlap.

FIG. 32A to FIG. 34C illustrate yet another aspect of this disclosure.

Figure 32A:
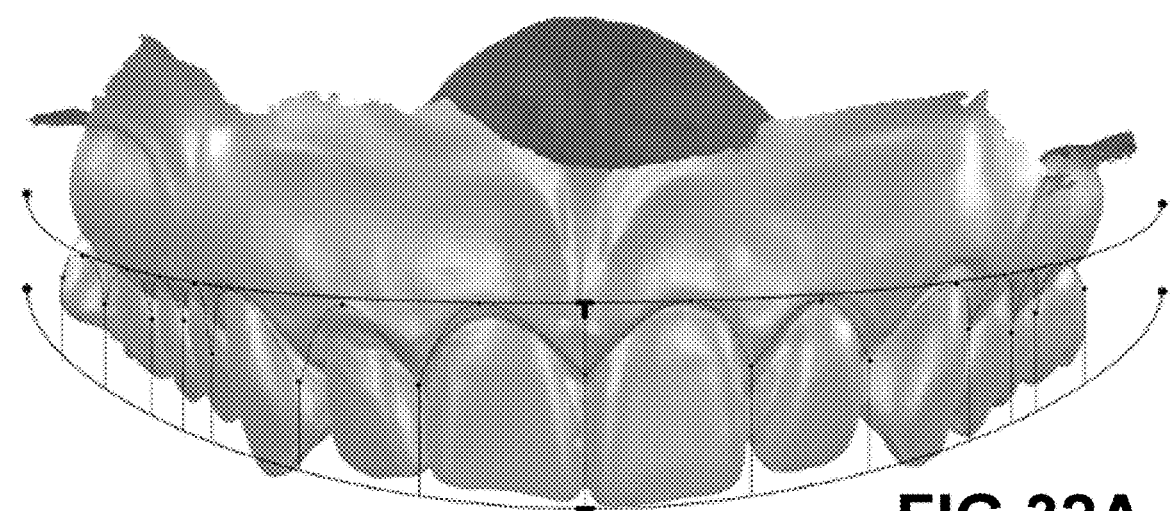
Figure 32B:
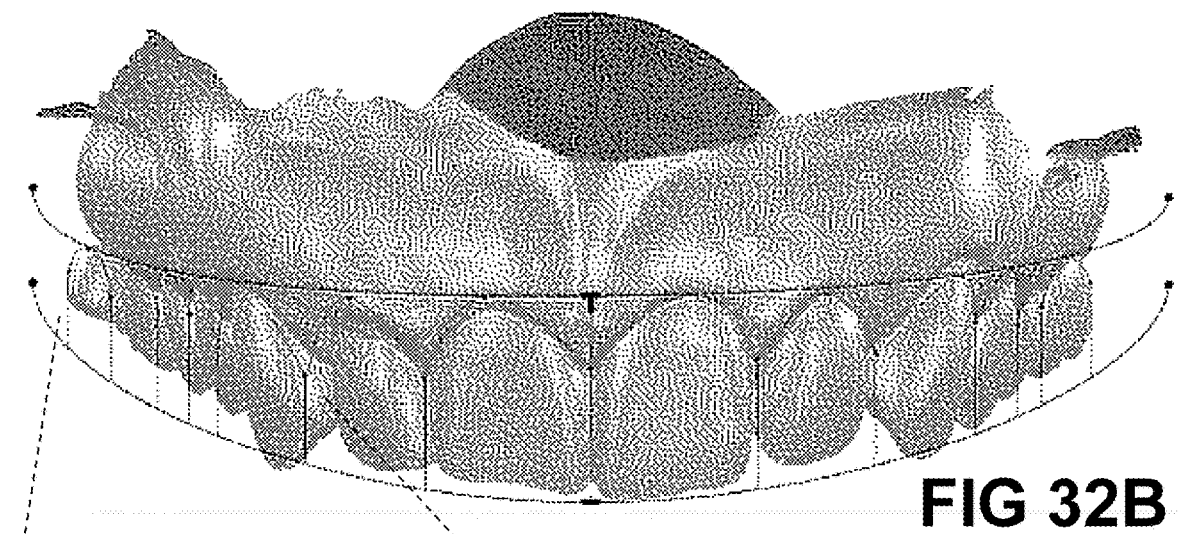
Figure 32C:
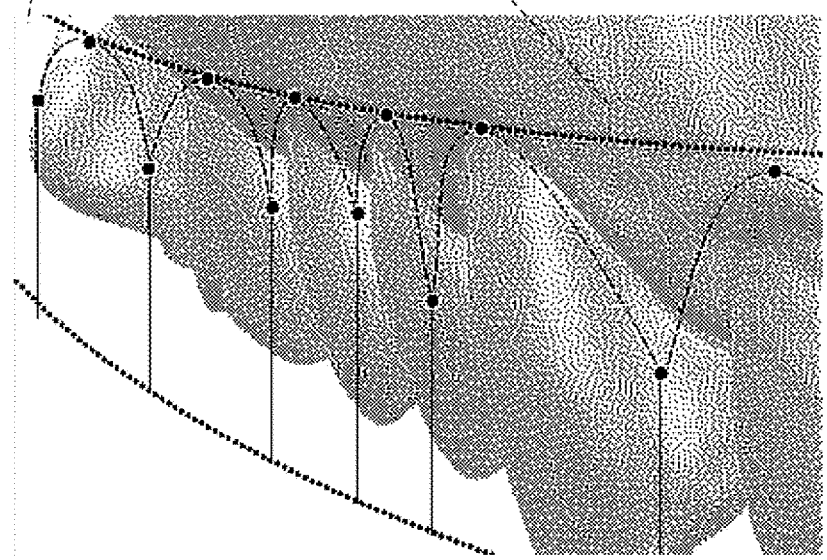

FIG. 32A to FIG. 32C shows a view of a surface obtained by a 3D intraoral scan. As can be seen, in this view the width, the papilla height, the gingival margin curve, etc. of frontal teeth is very well visible. Also, the position of the vertical ribs of the 3D bounding boxes of the frontal teeth to be seems correctly located between the frontal teeth, but that is not the case for teeth in the back. As explained above, a frontal view is very useful when modifying frontal teeth of a smile, but is not very handy when designing teeth in the back.

Figure 33A:
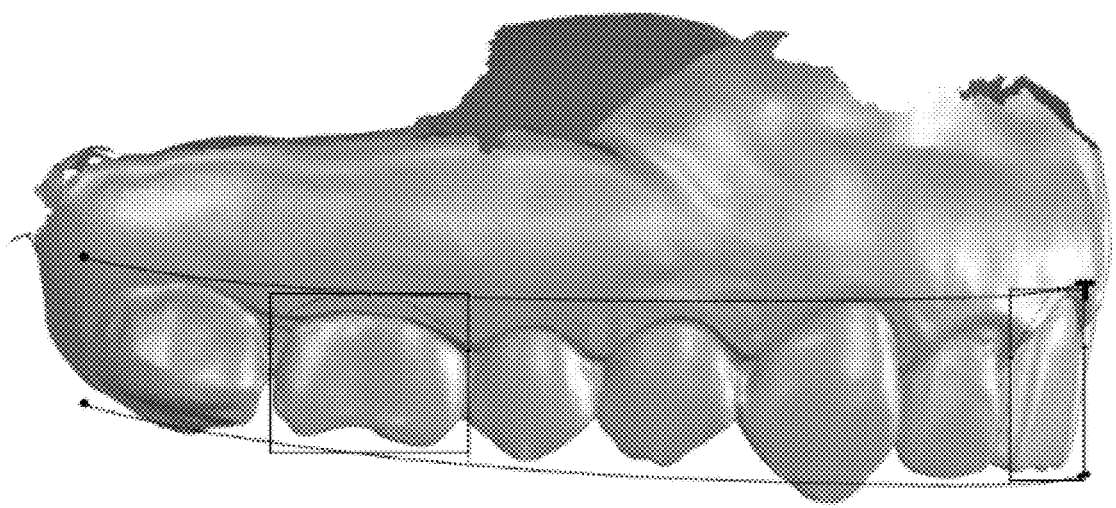
FIG. 33A to FIG. 33C shows a view where the width, the papilla height, the gingival margin curve, etc. of teeth in the back is very well visible, but not for frontal teeth.
Figure 33B:
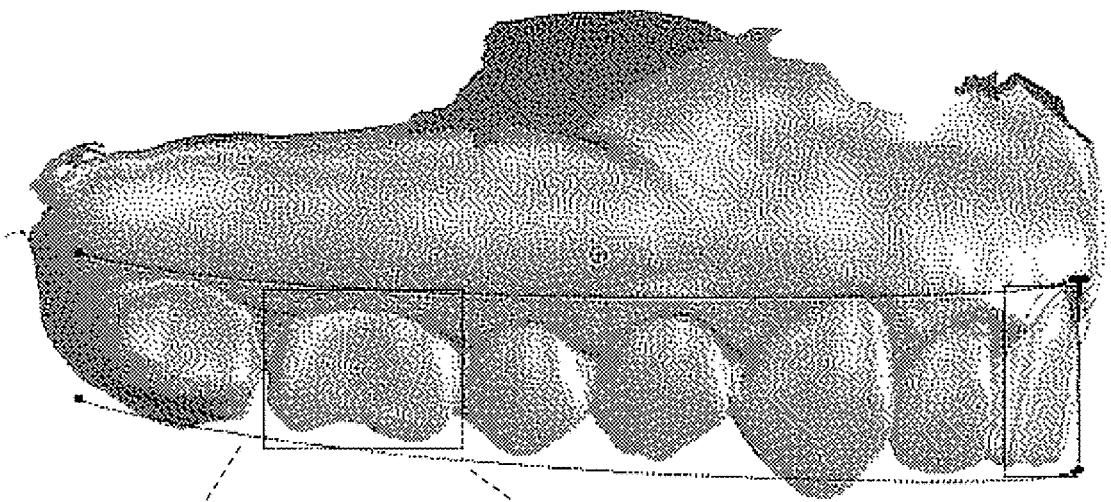
Figure 33C:
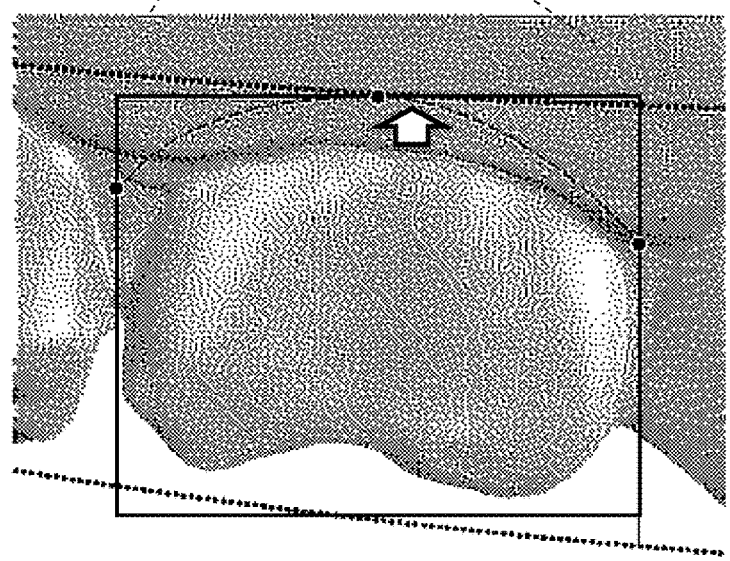

FIG. 33A to FIG. 33C shows another view of the teeth of a patient, where the width, the papilla height, the gingival margin curve, etc. of teeth in the back is very well visible. This view can also be obtained from the 3D intraoral scan. It was described above how 3D bounding boxes can be defined to model the teeth, such that matching teeth can be searched for in the digital library.

It turned out, however, that in a majority of the cases, the gingival margin curve of the patient needed to be slightly modified, e.g. as suggested in FIG. 33C. Choosing longer teeth from the 3D library was already possible by changing the size of the 3D bounding box as described above, but the algorithm described above offers the dentist a number of candidate matching teeth, from which the dentist has to manually select one, trying to envision (or simulating) how the selected tooth from the library will look like in this patients mouth, and moreover, after the gingival margin curve has slightly shifted.

They wanted to simplify this selection process, by automatically finding a better match that also takes into account the "future" gingival margin curve, but were faced with the problem that the gingival margin curve is a curve in 3D space, which is not easy to describe mathematically, and/or to modify easily, and most of all, they did not want to lose the benefits offered by their current way of indexing. They did not think it was possible to further automate this selection, until they came to a new insight, explained next, and illustrated in FIG. 34A to FIG. 34C.

Figure 34A:
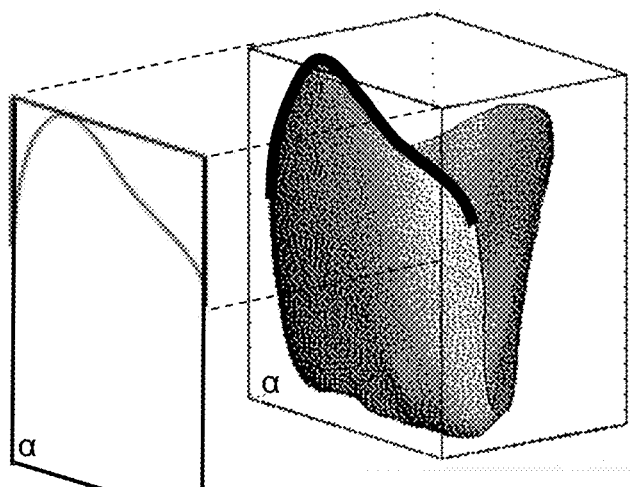
FIG. 34A shows a surface of a tooth extracted from a 3D intraoral scan. A thick black line is added to show a relevant portion of the gingival margin curve in 3D space. A projection of this portion is made to one of the planes of the 3D bounding box.

FIG. 34A shows a surface of a single tooth extracted from a 3D intraoral scan. A thick black line is added to this picture to show a relevant portion of the gingival margin curve in 3D space. The position of this curve in 3D space can be found using known software techniques. However, rather than trying to describe the position of individual points of this curve in 3D space, they came to the idea to make a 2D projection of this portion to one of the planes of the 3D bounding box, and to find teeth with a similar projected 2D portion. Furthermore, they realised that a matching tooth does not need to have the exact same projected portion, but a good approximation of the projected portion is sufficient. Based on these insights, they were able to codify the projected 2D portion in an efficient manner, such that it can be added to the index, and in a way that allows the digital library to be search in a highly efficient manner, not only taking into account the dimensions of the envisioned (i.e. future) 3D bounding box, but also the position of the envisioned (i.e. future) gingiva.

Figure 34B:
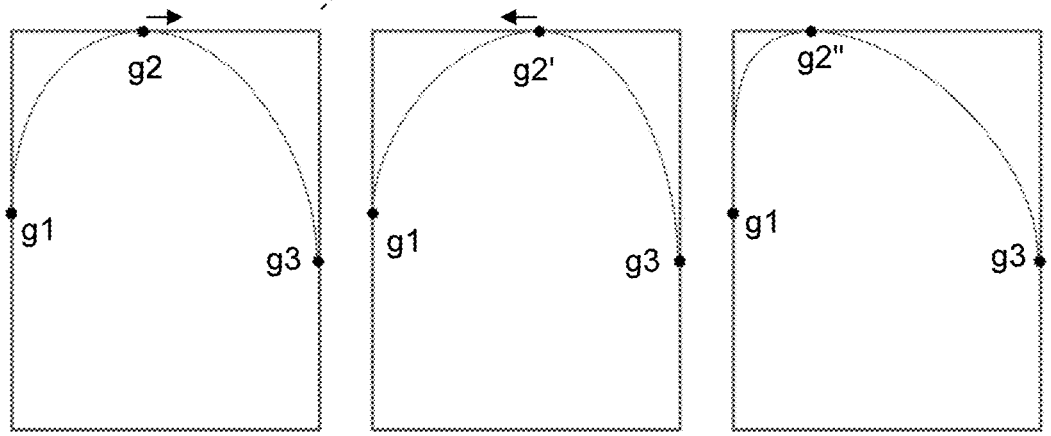
FIG. 34B shows how the projected portion of the gingival margin curve can be represented or approximated by a spline or a simple Bezier curve characterised by only a few points, and shows how this projected curve can easily and conveniently be modified to an envisioned (future) shape.

FIG. 34B shows a few examples of how the 2D projected portion of the gingival margin curve in the plane α can be represented or approximated by a spline or by a simple Bezier curve characterised by only a few points. In the examples of FIG. 34B, only three points are shown. In the left example, the points g1, g2 and g3 indicate the position of an initial 2D projected portion. The design software is preferably made such that the user can simply move these points, e.g. by dragging them. In the three examples of FIG. 34B, the points g1 and g3 are kept stationary, and the central Figure is obtained by moving the point g2 to the right, to the position shown by g2'; and the Figure on the right is obtained by moving the point g2 to the left, to the position shown by g2". While not shown in FIG. 34B, the software would preferably also allow a user to move the points g1 and g3 up or down, and the software would preferably find a candidate tooth from the indexed library matching these new positions.

Figure 34C:
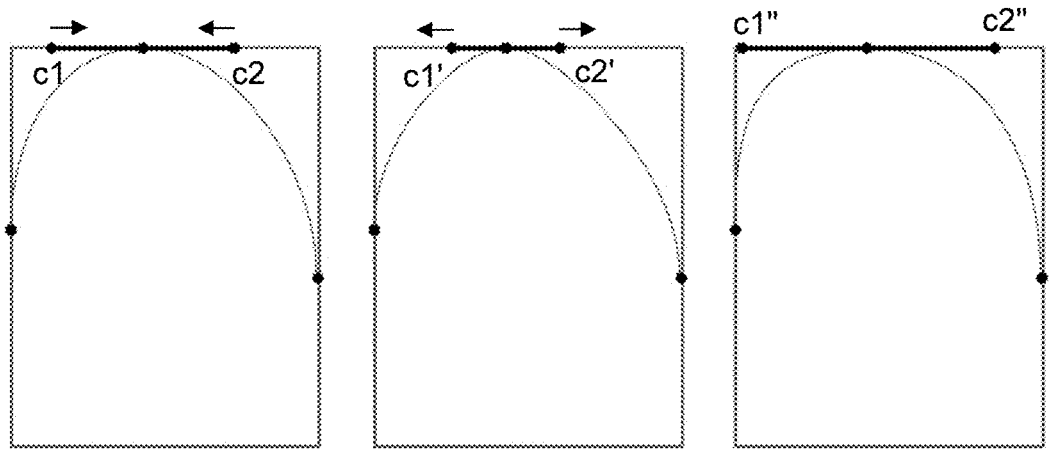

FIG. 34C shows a variant of FIG. 34B, where the user cannot only change the position of some characteristic points (e.g. g1, g2, g3), but where in this example, the user can also modify the curvature of the 2D projected curve, e.g. by moving some control points c1, c2. The three examples of FIG. 34C show how the 2D curve changes when the control points c1 and c2 are brought closer together, or spaced further apart. Of course, this disclosure is not limited to these examples, and other characteristic points, or control points may also be used.

While individual features are explained in different drawings and different embodiments of this disclosure, it is contemplated that features of different embodiments can be combined, as would be obvious to the skilled person, when reading this document.

What is claimed is:

1. A computer implemented method of generating a dental design, the computer implemented method comprising:
   (a) capturing or obtaining a facial image of a patient, the facial image comprising a head of the patient and a smile comprising a plurality of upper teeth;
   (b) showing the facial image or an image derived therefrom on a display as a first image;
   (c) capturing or obtaining a three-dimensional (3D) intraoral scan comprising the plurality of upper teeth;
   (d) aligning the 3D intraoral scan to the head of the patient;
   (e) determining a plurality of 3D bounding boxes in the 3D intraoral scan, each bounding box comprising a single tooth, and determining a gingival margin curve of the single tooth;
   (f) showing a view of the 3D intraoral scan and the plurality of 3D bounding boxes as a second image on the display, and showing a plurality of characteristic points related to the gingival margin curve;
   (g) showing a representation of the plurality of 3D bounding boxes and a representation of the gingival margin curve as a graphical overlay on the first image on the display; and
   (h) performing at least once:
      (i) allowing a user to modify at least one dimension of at least one 3D bounding box in the first image or the second image and allowing the user to modify one or more of the plurality of characteristic points related to the gingival margin curve, and detecting the modification;
      (ii) for each modification:
         defining a limited set of parameters to characterize a corresponding tooth inside the at least one 3D bounding box, including a parameter indicative for a unique position of the corresponding tooth in a mouth, and dimensions of the at least one 3D bounding box, and including positions of the plurality of characteristic points related to the gingival margin curve; and
         searching and retrieving a limited number of candidate matching teeth from an indexed digital library comprising a plurality of 3D digital teeth, the index being based on the limited set of parameters and being used to determine a matching score between a digital tooth from the indexed digital library and the at least one 3D bounding box and the representation of the gingival margin curve; and
         proposing a candidate matching tooth from the limited number of candidate matching teeth; and
      (iii) overlaying the first image with a digital representation of the proposed candidate matching tooth from the indexed digital library.

2. The computer implemented method according to claim 1, wherein:
   the plurality of characteristic points related to the gingival margin curve are projected on at least one surface of the at least one 3D bounding box; and
   the index comprises positions of the plurality of characteristic points on the at least one surface of the at least one 3D bounding box.

3. The computer implemented method according to claim 1, further comprising:
   saving the dental design as a digital file on a non-volatile memory or on a storage device.

4. The computer implemented method according to claim 1, further comprising:
   providing a 3D file of at least one candidate matching tooth from the indexed digital library, optionally after scaling, rotation, or digital grinding.

5. The computer implemented method according to claim 4, further comprising:
   producing at least one physical object based on the 3D file.

6. The computer implemented method according to claim 1, wherein (d) comprises aligning a reference frame of the 3D intraoral scan to a reference frame of the head of the patient using the facial image or the image derived therefrom.

7. The computer implemented method according to claim 1, wherein the plurality of 3D bounding boxes have a beam shape or a cuboid shape or a prism shape.

8. The computer implemented method according to claim 1, further comprising:
   displaying a U-shaped curve substantially tangential to an outside surface of the plurality of upper teeth of the patient, and situated near incisal edges of the plurality of upper teeth.

9. The computer implemented method according to claim 8, wherein the plurality of 3D bounding boxes have a plurality of rectangular surfaces including one surface being substantially tangential to the U-shaped curve.

10. The computer implemented method according to claim 1, wherein the plurality of 3D bounding boxes have a plurality of ribs which form an angle smaller than 15° with a vertical axis of the head of the patient.

11. The computer implemented method according to claim 1, wherein the gingival margin curve is represented as a spline or as a simple Bezier curve passing through at least three characteristic points.

12. The computer implemented method according to claim 1, wherein determining the limited set of parameters to characterize the corresponding tooth inside the at least one 3D bounding box further comprises:
   determining at least one parameter for describing a first embrasure; and
   determining at least one parameter for describing a second embrasure.

13. The computer implemented method according to claim 1, wherein (g) further comprises:
   allowing the user to select another matching tooth from the limited number of candidate matching teeth, and overlaying the first image with a digital representation of the selected candidate matching tooth.

14. A computer arrangement comprising:
   a computer device comprising at least one processor and a memory, the memory comprising an executable file;
   a display connectable to, or connected to, or embedded in the computer device, and configured for displaying a facial image;
   a pointing device connectable to, or connected to, or embedded in the computer device, and configured for receiving user input,
   wherein the executable file contains executable instructions that perform a method according to claim 1, when being executed by the at least one processor.

15. A computer implemented method of generating a dental design, the computer implemented method comprising:

(a) capturing or obtaining a facial image of a patient, the facial image comprising a head of the patient and a smile comprising a plurality of upper teeth;
(b) showing the facial image or an image derived therefrom on a display as a first image;
(c) capturing or obtaining a three-dimensional (3D) intraoral scan comprising the plurality of upper teeth;
(d) aligning the 3D intraoral scan to the head of the patient;
(e) determining a plurality of 3D bounding boxes in the 3D intraoral scan, each bounding box comprising a single tooth, and determining a gingival margin curve of the single tooth;
(f) showing a view of the 3D intraoral scan and the plurality of 3D bounding boxes as a second image on the display, and showing a plurality of characteristic points related to the gingival margin curve;
(g) showing a representation of the plurality of 3D bounding boxes and a representation of the gingival margin curve as a graphical overlay on the first image on the display; and
(h) performing at least once:
  (i) allowing the user to modify one or more of the plurality of characteristic points related to the gingival margin curve, and detecting the modification;
  (ii) for each modification:
    defining a limited set of parameters to characterize a corresponding tooth inside the at least one 3D bounding box, including a parameter indicative for a unique position of the corresponding tooth in a mouth, and dimensions of the at least one 3D bounding box, and including positions of the plurality of characteristic points related to the gingival margin curve; and
    searching and retrieving a limited number of candidate matching teeth from an indexed digital library comprising a plurality of 3D digital teeth, the index being based on the limited set of parameters and being used to determine a matching score between a digital tooth from the indexed digital library and the representation of the gingival margin curve; and
    proposing a candidate matching tooth from the limited number of candidate matching teeth; and
  (iii) overlaying the first image with a digital representation of the proposed candidate matching tooth from the indexed digital library.

* * * * *